(12) United States Patent
De Waard

(10) Patent No.: US 9,439,975 B2
(45) Date of Patent: Sep. 13, 2016

(54) SMALL EFFICIENT CELL PENETRATING PEPTIDES DERIVED FROM THE SCORPION TOXIN MAUROCALCINE

(75) Inventor: Michel De Waard, Saint-Christophe sur Guiers (FR)

(73) Assignees: **Commissariat A L'Energie At

(56) References Cited

OTHER PUBLICATIONS

Esteve, E., et al.; "*Transduction of the Scorpion Toxin Maurocalcine into Cells: Evidence That the Toxin Crosses the Plasma Membrane*;" The Journal of Biological Chemistry, vol. 280, No. 13; pp. 12833-12839; dated Jan. 2005; retrieved on Dec. 20, 2013 from <http://www.jbc.org/content/280/13/12833.full.pdf+html>.

Fajloun, Z., et al.; "*Chemical synthesis and characterization of maurocalcine, a scorpion toxin that activates Ca2+ release channel/ryanodine receptors*;" FEBS Letters, vol. 469, No. 2; pp. 179-185; dated Jan. 2000; retrieved on Dec. 20, 2013 from <http://www.sciencedirect.com/science/article/pii/S0014579300012394>.

Kim, D. H., et al.; "Kinetic studies of calcium release from sarcoplasmic reticulum in vitro;" The Journal of Biological Chemistry, vol. 258, No. 16; pp. 9662-9668; dated Aug. 1983; retrieved on Dec. 23, 2013 from <http://www.jbc.org/content/258/16/9662.full.pdf+html>.

Lukacs, B., et al.; "*Charged Surface Area of Maurocalcine Determines Its Interaction with the Skeletal Ryanodine Receptor*;" Biophysical Journal, vol. 95, No. 7; pp. 3497-3509; dated Oct. 2008; retrieved on Dec. 20, 2013 from <http://download.cell.com/biophysj/pdf/PIIS0006349508784923.pdf>.

Mabrouk, K., et al.; "*Critical amino acid residues of maurocalcine involved in pharmacology, lipid interaction and cell penetration*;" Biochimica et Biophysica Acta (BBA)—Biomembranes, vol. 1768, No. 10; pp. 2528-2540; dated Sep. 2007; retrieved on Dec. 23, 2013 from <http://www.sciencedirect.com/science/journal/00052736/1768/10>.

McKenzie, D. L., et al.; "*A Potent New Class of Reductively Activated Peptide Gene Delivery Agents*;" The Journal of Biological Chemistry, vol. 275, No. 14; dated Apr. 2000; retrieved on Dec. 23, 2013 from <http://www.jbc.org/content/275/14/9970.full.pdf+html>.

Merrifield, R. B.;"Solid-Phase Peptide Synthesis;" Advances in Enzymology and Related Areas of Molecular Biology, Vo. 32; pp. 221-296; abstract retrieved on Dec. 23, 2013 from <http://onlinelibrary.wiley.com/doi/10.1002/9780470122778.ch6/summary>.

Mosbah, A., et al.; "*A new fold in the scorpion toxin family, associated with an activity on a ryanodine-sensitive calcium channel*;" Proteins vol. 40, No. 3; pp. 436-442; dated Aug. 2000; abstract retrieved from <http://onlinelibrary.wiley.com/doi/10.1002/1097-0134(20000815)40:3%3C436::AID-PROT90%3E3.0.CO;2-9/abstract>.

Poillot, C., et al.; "*d-Maurocalcine, a Pharmacologically Inert Efficient Cell-penetrating Peptide Analogue*;" The Journal of Biological Chemistry, vol. 285, No. 44; pp. 34168-34180; dated Oct. 2010; retrieved on Dec. 23, 2013 from <http://www.jbc.org/content/285/44/34168.full.pdf+html>.

Pouvreau, S., et al.; "*Transient Loss of Voltage Control of Ca2+ Release in the Presence of Maurocalcine in Skeletal Muscle*;" Biophysical Journal, vol. 91, No. 6; pp. 2206-2215; dated Sep. 2006; retrieved on Dec. 20, 2013 from <http://download.cell.com/biophysj/pdf/PIIS000634950671935X.pdf>.

Ram, N., et al.;"Design of a Disulfide-less, Pharmacologically Inert, and Chemically Competent Analog of Maurocalcine for the Efficient Transport of Impermeant Compounds into Cells;" The Journal of Biological Chemistry, vol. 283, No. 40; pp. 27048-27056; dated Oct. 2008; retrieved on Dec. 23, 2013 from <http://www.jbc.org/content/283/40/27048.full.pdf+html?sid=1bcdd0fe-d007-480d-a7f8-a6fbfec3b602?>.

Ram, N., et al.; "*Direct Peptide Interaction with Surface Glycosaminoglycans Contributes into Cells*;" The Journal of Biological Chemistry, vol. 283, No. 40; pp. 27048-27056; dated Oct. 2008; retrieved on Dec. 23, 2013 from <http://www.jbc.org/content/283/40/27048.full.pdf+html>.

Szappanos, H., et al.; "*Differential effects of maurocalcine on Ca2+ release events and depolarization-induced Ca2+ release in rat skeletal muscle*;" The Journal of Physiology, Vo. 565, No. 3; pp. 843-853; dated 2005; retrieved on Dec. 20, 2013 from <http://jp.physoc.org/content/565/3/843.full.pdf+html>.

International Search Report and Written Opinion for Application No. PCT/IB2012/053120; dated Jan. 28, 2013.

\* cited by examiner

A

| | | Net charge (NC) | % |
|---|---|---|---|
| MCa$_{UF1-33}$-C | GDAbuLPHLKLAbuKENKDAbuAbuSKKAbuKRRGTNIEKRAbuR-C | +7 | 33 |
| MCa$_{UF1-20}$-C | GDAbuLPHLKLAbuKENKDAbuAbuSKK-C | +2 | 25 |
| MCa$_{UF1-15}$-C | GDAbuLPHLKLAbuKENKD-C | 0 | 20 |
| MCa$_{UF1-9}$-C | GDAbuLPHLKL-C | 0 | 11 |
| MCa$_{UF8-33}$-C | KLAbuKENKDAbuAbuSKKAbuKRRGTNIEKRAbuR-C | +8 | 42 |
| MCa$_{UF11-33}$-C | KENKDAbuAbuSKKAbuKRRGTNIEKRAbuR-C | +7 | 43 |
| MCa$_{UF14-33}$-C | KDAbuAbuSKKAbuKRRGTNIEKRAbuR-C | +7 | 45 |
| MCa$_{UF18-33}$-C | SKKAbuKRRGTNIEKRAbuR-C | +7 | 50 |
| MCa$_{UF20-33}$-C | KAbuKRRGTNIEKRAbuR-C | +6 | 50 |
| MCa$_{UF22-33}$-C | KRRGTNIEKRAbuR-C | +5 | 50 |
| MCa$_{UF25-33}$-C | GTNIEKRAbuR-C | +2 | 33 |
| MCa$_{UF6-25}$-C | HLKLAbuKENKDAbuAbuSKKAbuKRRG-C | +6 | 40 |
| MCa$_{UF14-25}$-C | KDAbuAbuSKKAbuKRRG-C | +5 | 50 |

B

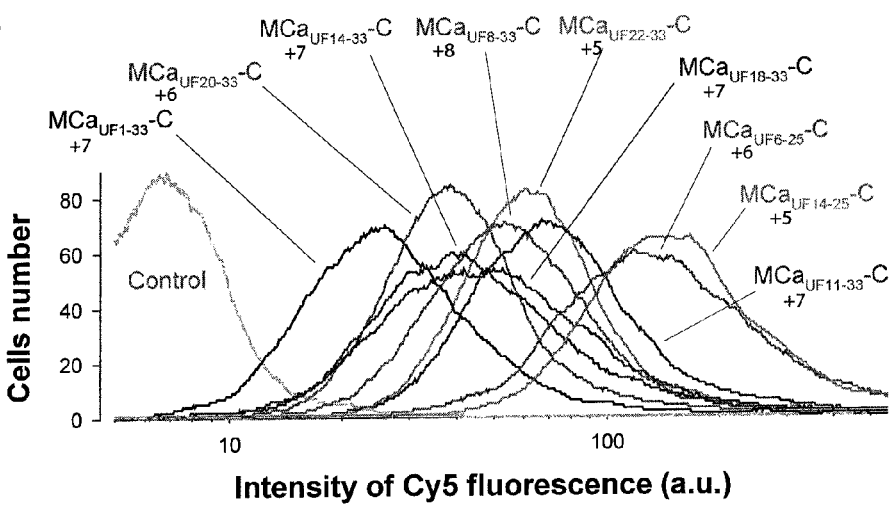

C

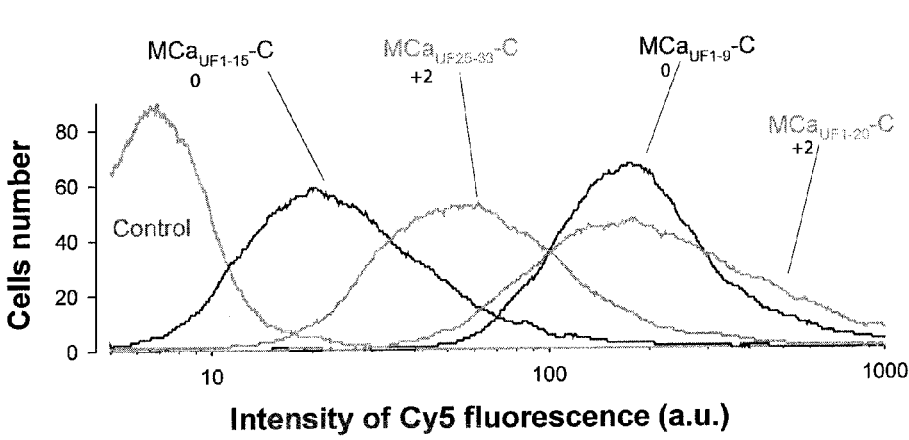

FIGURE 2

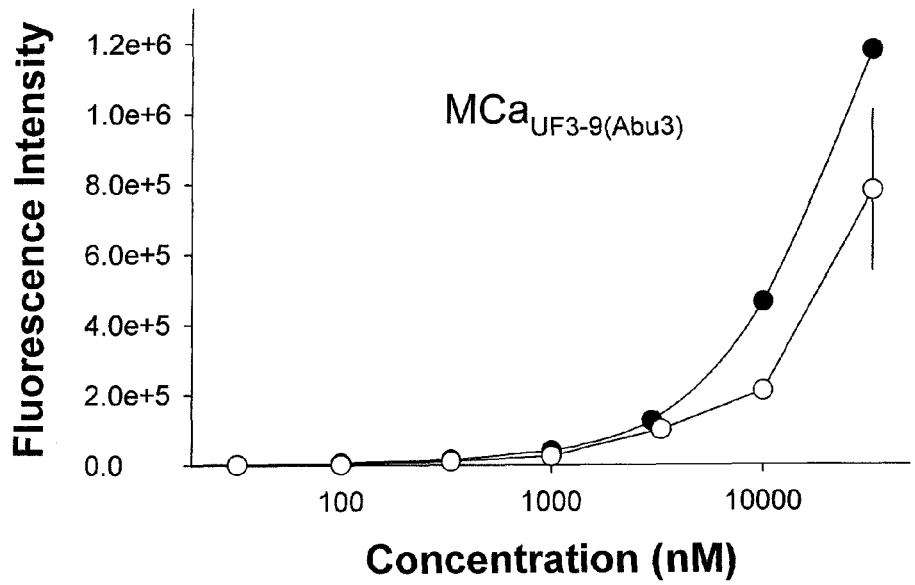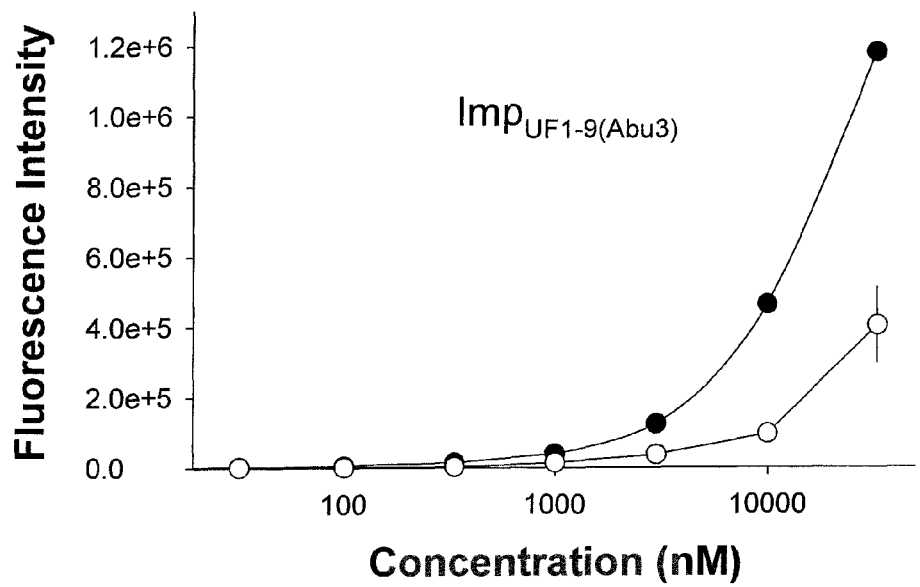
FIGURE 12

A Analogue compound
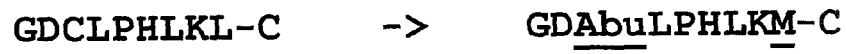
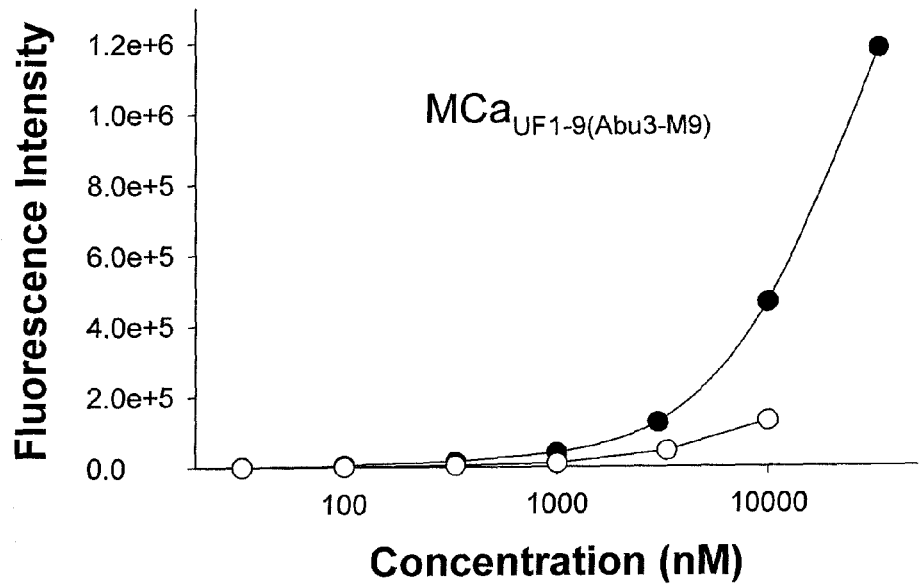
B Analogue compound
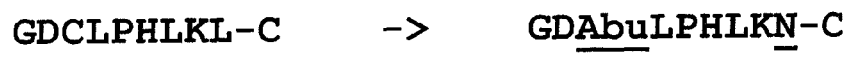
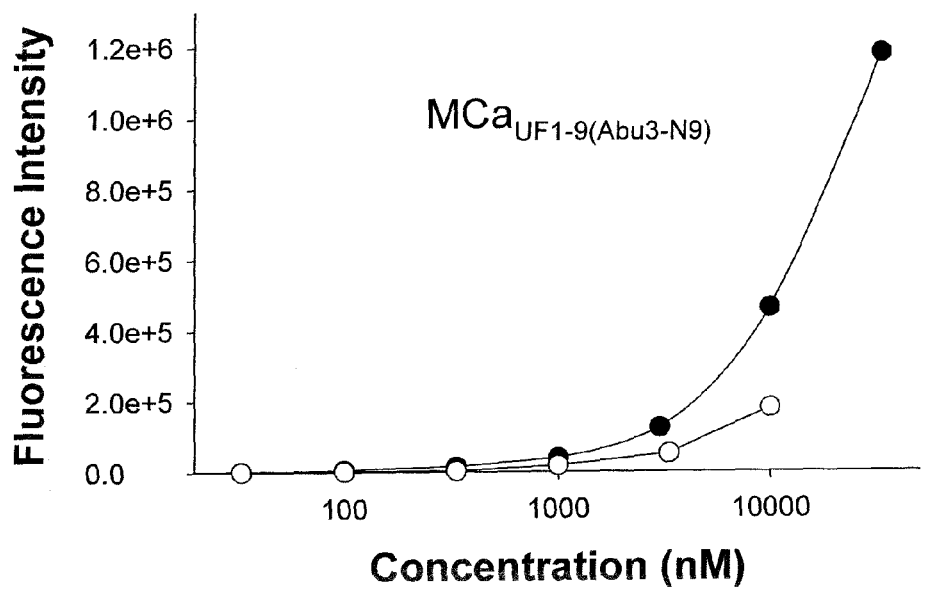
FIGURE 13

SMALL EFFICIENT CELL PENETRATING PEPTIDES DERIVED FROM THE SCORPION TOXIN MAUROCALCINE

The invention relates to small cell penetrating peptides (CPP) derived from the scorpion toxin maurocalcine and to their use as vectors for the intracellular delivery of various drugs and agents.

Cell-penetrating peptides (CPP), also called protein transduction domains (PTDs), membrane translocation sequences (MTS) or translocating peptides are capable of crossing the plasma membrane of cells and of carrying cell-impermeable compounds across the plasma membrane, efficiently, rapidly, at low concentration, in vitro and in vivo, into various cell types. The 60 amino-acid long homeodomain of the *Drosophila* transcription factor Antennapedia (ANTP) was the first CPP discovered and shown to serve as a signal for the internalization of other polypeptides. Its penetration and translocation properties were further restricted to a peptide of 16 residues (penetratine or Pen). Now along with Pen, multiple CPPs including protein transduction domains (PTD) found in proteins such as HIV-1 Tat and HSV-1 VP22, synthetic 7-9 homoarginine peptides and chimera peptides such as transportan, are intensively studied. Little structural resemblances have been found between the different families of CPP. The only characteristic common to all these peptides is that they are unusually enriched in basic amino acids resulting in a high positive net charge. Various molecules or particles of different sizes such as oligonucleotides, peptide nucleic acids (PNAs), siRNAs, cDNA, plasmids, peptides, proteins, antibodies, pharmacologicaly active drugs, imaging agents, liposomes and nanoparticles have been successfully delivered into cells when attached to a CPP. Thus, CPPs represent powerful tools for the delivery of various cargoes to their site of action in a cell, in particular the cytosol and the nucleus. These peptides have opened a new avenue in medicine and research, allowing otherwise impermeable agents of therapeutic, diagnostic and technical value to enter cells and induce biological responses.

Maurocalcine (MCa) is the first demonstrated example of an animal toxin peptide with efficient cell penetration properties. The toxin is a 33-mer peptide (SEQ ID NO: 1) that was initially isolated from the venom of a Tunisian chactid scorpion, *Scorpio maurus palmatus* (Fajloun et al., 2000). Maurocalcine belongs to a family of peptide that folds according to an Inhibitor Cystine Knot (ICK motif), and thus contains three disulfide bridges with a $Cys^1$-$Cys^4$, $Cys^2$-$Cys^5$ and $Cys^3$-$Cys^6$ connecting pattern (Moshbah et al., 2000). The solution structure, as defined by $^1$H-NMR, illustrates that MCa contains three β-strands (strand 1 from amino acid residues 9 to 11, strand 2 from 20 to 23, and strand 3 from 30 to 33). One distinctiveness of MCa is the fact that it is greatly enriched in basic amino acid residues. Out of the 33 amino acids that compose MCa, twelve of them are basic, most of them represented by Lys residues. Interestingly, the β-strands of MCa encompass most of the basic domains (FIG. 1A). MCa turned to be of interest for research for several reasons.

First, it is an exquisite pharmacological activator of the ryanodine receptor type 1 (RyR1) from skeletal muscle since it promotes high Po gating modes and long-lasting subconductance states of the ion channel (Chen et al., 2003; Lukacs et al., 2008). On myotubes, application of MCa rapidly induces $Ca^{2+}$ release from the sarcoplasmic reticulum (SR) (Estève et al., 2003), a result further confirmed by positive effect of MCa on the release of $Ca^{2+}$ from purified SR vesicles (Chen et al., 2003; Estève et al., 2003). The interaction of MCa with RyR1 has been witnessed by increased [$^3$H]-ryanodine binding onto purified RyR1 (Chen et al., 2003; Estève et al., 2003). The binding site for MCa on RyR1 has also been mapped and shown to correspond to domain(s) that have a predicted localization within the cytoplasm (Altafaj et al., 2005).

Second, MCa has a unique sequence homology with the II-III loop of the L-type calcium channel Cavil subunit over a domain that is slightly larger than the second β-strand of MCa (FIG. 1A) (Estève et al., 2003). This loop is heavily involved in excitation-contraction coupling through direct molecular interactions with RyR1 (Altafaj et al., 2005; Szappanos et al., 2005). This homology turns out to be of tremendous help for understanding how L-type channels are involved in excitation-contraction coupling (Lukacs et al., 2008, Szappanos et al., 2005; Pouvereau et al., 2006).

Third, MCa has been shown to act as a cell penetrating peptide (CPP) (Estève et al., 2005; International PCT Application WO 2006/051224 and corresponding US Patent Application US 2009/0142266). This discovery stemmed from earlier criticisms that MCa may not be an activator of RyR1 because peptide toxins were not known to cross the plasma membrane, which would be required here to bind to RyR1. Studies that were undertaken to demonstrate the ability of MCa to reach its target showed that i) MCa triggers $Ca^{2+}$ release from the sarcoplasmic reticulum a few seconds after its application in the extracellular medium (Estève et al., 2003), and ii) intracellular accumulation of fluorescent-streptavidine occurs if it incubated first with biotinylated MCa (Estève et al., 2005; International PCT Application WO 2006/0512249 and corresponding US Patent Application US 2009/0142266). Since these pioneering studies, MCa or full-length 33 amino acid analogues thereof proved powerful vectors for the cell entry of proteins, peptides (Ram et al., 2008), nanoparticles, or drugs such as doxorubicine (Aroui et al., Cancer Lett., 2009; Aroui et al., Apoptosis, 2009; Aroui et al., Pharm. Res., 2009). Although the mode of cell penetration of MCa may vary according to cargo nature, cell type or chemical linkage employed, the data gathered so far suggest that the peptide may enter cells according to two priming steps onto the plasma membrane: first an interaction with proteoglycans with an affinity in the micromolar range, followed by a second interaction with negatively charged lipids which occurs with greater affinity (Boisseau et al., 2006; Ram et al., 2008). The mode of cell entry of MCa is not altered by the absence of proteoglycans, but simply reduced quantitatively, suggesting that proteoglycans do not orient the mode of cell penetration. Two modes seem to concur to MCa cell entry, as far as observed, one related to macropinocytosis and another to membrane translocation. The balance between both modes of entry was found correlated to cargo nature and the type of MCa analogue used.

It is of great interest to pursue the study of MCa as CPP in spite of the wealth of new CPP sequences that are discovered yearly. Among the competitive advantage of MCa over other CPP sequences are the facts that it has almost no associated toxicity in vitro and in vivo, penetrates into cells at very low concentrations, and is extremely stable in vivo upon intravenous injection (over 24 hrs). While MCa appears as an elaborate and efficient CPP, its pharmacological properties represent a serious hindrance while envisioning in vitro and in vivo applications. In addition, because of its length (33 amino acid residues) and the presence of three internal disulfide bridges, MCa is a relatively difficult to synthesize CPP, comparatively to other CPP. Several attempts were made in the past to try to design MCa analogues which are less complex than MCa, lack the pharmacological effects of wild-type MCa but preserve or enhance its cell penetration efficiencies.

The first strategy, based on single point mutations spanning MCa sequence, preserved the disulfide bridges and the 3D structure of the analogues. The study of the MCa mutants demonstrated that the molecular determinant of MCa implicated in pharmacology and cell penetration overlap partially. In addition, this work confirmed that the main requirement for an efficient cell penetration of MCa is the presence of a basic surface. Many of the amino acids involved in RyR1 binding and pharmacology were located within the cluster of basic amino acids that presented sequence homology with the L-type $Ca_v1.1$ channel. Some of these residues, but not all, were also important for cell penetration properties. Using this approach, full-length MCa analogues with reduced or complete loss of pharmacological effects were defined (Mabrouk et al., 2007). Nevertheless, none of the analogues totally preserved the cell penetration efficiency of MCa. One analogue only had lost entirely its pharmacological action (MCa R24A). However, its cell penetration efficiency was decreased. Some other analogues were better that MCa itself for cell penetration. However, their affinity for RyR1 was unchanged or increased (MCa E12A). Combining a pair of mutations, one aiming at disrupting pharmacology and one at improving penetration, may thus be used in the future to define still better CPP analogues derived of full-length MCa.

The second strategy was based on the chemical synthesis of D-MCa, a full-length analogue entirely based on the use of D-amino acids. This peptide is a mirror image of the natural L-MCa but, like other D-CPP, preserves its cell penetration properties, while losing entirely its ability to interac with RyR1 (Poillot et al., 2010). This CPP analogue has several advantages. It no longer is sensitive to proteases which may be an additional advantage for in vivo experiments where the half-life of the circulating peptide matters. In these two strategies while being effective, one may argue that i) the peptides are still among the longest CPP known to date, implying increased costs of production, and ii) the yield of production of these peptides is hampered by the folding process. Also, the use of peptides with internal disulfide bridges, despite having advantageous features in term of stability in vivo, makes chemical coupling of these CPP to cargoes more complicated (difficulty to add extra Cys residues to the peptides for instance without interfering with the correct folding process).

The third strategy that was used to circumvent one of this criticism was the chemical synthesis of a full-length MCa analogue in which all internal Cys residues where replaced by isosteric 2-aminobutyric acid residues (Ram et al., J. Biol. Chem., 2008). The resulting peptide was still 33-mer long but one step in production was saved by avoiding the folding process. In addition, an extra-Cys residue could be added to the N-terminus of the peptide in order to favor simplified cargo grafting on this CPP analogue. This peptide, termed here C-MCaUF1-33 (C for extra-Cys, UF for unfolded, and 1-33 for its length, FIG. 1B) has no longer any secondary structures, but efficiently penetrates into cells. Interestingly also, the peptide completely lacks pharmacological activity indicating that folding and secondary structures are essential for binding onto RyR1. While this peptide is an efficient CPP, it remains less potent than MCa in its folded version.

The inventors have developed several truncated Mca peptides that have highly potent cell penetration capabilities, while losing pharmacological activity, preserving lack of cell toxicity, and with facilitated cargo grafting. Here, the inventors demonstrate that several efficient CPP can be derived from maurocalcine by replacing Cys residues by isosteric 2-aminobutyric acid residues and a sequence truncation down to peptides of up to 7 residues in length. A surprising finding is that all the truncated maurocalcine analogues possessed cell penetrating properties indicating that the maurocalcine is a highly specialized CPP. Many of the unfolded truncated MCa peptides are better CPP than unfolded MCa itself.

More surprisingly, the inventors have also found out that poorly charged MCa peptides (net positive charge of 0 to +3) can behave as efficient CPP. This is the case for MCaUF1-9, MCaUF3-9, MCaUF1-9(W3), HadUF1-11 and HadUF3-11 which are ones of the best performing CPPs, especially when low concentration of use is a quality of importance.

Interestingly, the truncated MCa peptides differ somewhat in their mode of cell penetration (direct membrane translocation versus endocytosis), some being more prone to enter cells by macropinocytosis than others. Various peptides were even insensitive to amiloride application suggesting that macropinocytosis did not contribute at all to their entry.

The inventors have also demonstrated that cargo coupling can occur at the N-terminus as well as the C-terminus of the peptide, enhancing the flexibility of cargo coupling to these CPPs.

The CPP potential of these peptides can be optimized by reintroducing one disulphide bond to restore some of the secondary structures that confer a competitive advantage to MCa for cell penetration. Further optimization of these CPPs is obtained by mutagenesis of the region Lys11-Ser18 including the mutation of E12 and D15 as well as further mutagenesis of negatively charged residues including D2 and E29.

The inventors have identified several interesting lead CPP based on unfolded MCa (MCaUF) truncation strategy. This is the case for MCaUF18-33 (macropinocytosis entry-independent), MCaUF1-9 (penetrates better at low concentration), and MCaUF14-25 (yields the greatest cell entry of the dye). These peptides are easy to produce, yield good cell penetration, and their cell penetrating characteristics can be further optimized by mutagenesis or by reintroducing one disulfide bridge to restore some of the secondary structures. This new generation of MCa analogues is predicted to have bright futures for CPP applications in vitro and in vivo.

In the following description, the standard one letter amino acid code is used. In addition, non-natural amino acids and groups of particular amino acids are referred to using the following one letter code:

a=L-alpha-aminobutyric acid, also named 2-amino butyric acid or Abu,

B=basic amino acid chosen from K and R,

J=hydrophobic amino acid chosen from W, F, L, I, V, M, A and C, $J^1$=hydrophobic amino acid chosen from W, F, L, I, V, A and C, and O=S, G, T, A, and V.

One aspect of the present invention relates to the use of a peptide as a vector for the intracellular delivery of a molecular cargo, wherein said peptide is a maurocalcine derived cell penetrating peptide consisting of a sequence selected from the group consisting of:

(I) $Z-X_1-X_2-X_3-X_4-X_5-X_6-X_7-Z'$, wherein:
 $X_1$ represents J or another amino acid different from B,
 $X_2$ represents J,
 $X_3$ represents B, J, or another amino different from S, T, D and E,
 $X_4$ represents J or another amino acid different from B, S, T, D and E,
 $X_5$ represents $J^1$,
 $X_6$ represents J, B, or another amino acid, and
 $X_7$ represents J, B, or another amino acid, with the proviso that the sequence $X_1$ to $X_7$ comprises three or four hydrophobic amino acids and one or two basic amino acids, and no more that two basic amino acids and four hydrophobic amino acids,
 Z and Z' together represent a sequence of no more than 13 amino acids, or Z and/or Z' are no amino acid (i.e. absent), and
 said sequence (I) has a net charge of 0 to +2 when Z and Z' are no amino acid or of 0 to +3 when Z and/or Z' are present, and (II) $U-X^aBBJBBBX^b-U'$, wherein:
 $X^a$ is S, G, T, J, Q or N,
 $X^b$ is G or J, wherein B and J are as defined above, and
 U is a sequence of 1 to 12 amino acids or no amino acid,
 U' is a sequence of 1 to 8 amino acids or no amino acid, with the proviso that only one of U and U' is present.

The peptide according to the present invention is a cell penetrating peptide or CPP. Therefore, it is capable of crossing the plasma membrane of cells and of carrying small and large non-permeant molecular cargoes across the plasma membrane, efficiently, rapidly, at low concentration, in vitro and in vivo, into various cell types. Non-permeant molecular cargoes include but are not limited to peptides, proteins including antibodies, small (oligonucleotides, PNAs) and large nucleic acids, small and large chemical compounds, nanoparticles and liposomes. These properties can be readily verified by technique known to those skilled in the art such as those described in the examples of the present application.

The peptide of the invention provides an efficient carrier or vector for the delivery of various drugs and agents of therapeutic, diagnostic and technological value to their site of action in a cell, in particular the cytosol and the nucleus. Therefore, the peptide of the invention can be used for various in vivo applications including therapy, diagnosis, medical imaging and research.

DEFINITIONS

"peptide" refers to a chain of natural amino acids (20 gene-encoded amino acids in a L- or D-configuration) linked via a peptide bond and furthermore comprises peptidomimetics of such peptide where the amino acid(s) and/or peptide bond(s) have been replaced by functional analogues. Such functional analogues include all known amino acids other than said 20 gene-encoded amino acids. A non-limitative list of non-coded amino acids is provided in Table 1A of US 2008/0234183 which is incorporated herein by reference. For example L-alpha-aminobutyric acid, also named 2-amino butyric acid (Abu) is an isosteric analogue of cysteine.

"net charge of a sequence" will refer to the value obtained by adding all the positive and negative charges which are present on the amino acids of a sequence, as shown in FIG. 2A; an acidic amino acid (D, E) has one negative charge (−1), a basic amino acid (K, R) has one positive charge (+1) and the other amino acids have no charge (0). H are not taken into consideration.

"cargo", "molecular cargo", 'impermeant cargo' refers to a substance that can be transported across the plasma membrane of cells and delivered into cells by using a cell penetrating peptide as a delivery vehicle. The cargo may be a molecule such as a small molecule or a macromolecule or a particle such as a nanoparticle or a liposome.

"cell" refers to a cell in a cell culture (in vitro) or in an intact multicellular organism (in vivo). The cell can be prokaryotic or eukaryotic. Preferably, the cell is from a mammal (human, animal) or a plant.

The peptide consisting of the sequence (I) is also named peptide (I) or peptide I and the peptide consisting of the sequence (II) is also named peptide (II) or peptide II. "Peptide" refers to both peptides (I) and (II).

The peptide (I) which consists of 7 to 20 amino acids is derived from the maurocalcine peptide 1 to 20 ($MCa_{1-20}$). The peptide $MCa_{1-20}$ which has the amino acid sequence SEQ ID NO: 2 comprises the sequence $X_1$ to $X_7$ in positions 3 to 9. The peptide $MCa_{3-9}$ has the sequence SEQ ID NO: 3, where $X_1$ is C, $X_2$ is L, $X_3$ is P, $X_4$ is H, $X_5$ is L, $X_6$ is K and $X_7$ is L. Furthermore, $X_7$ is R in $Opi/IpTx_{3-9}$ (SEQ ID NO: 6); $X_2$ is I, $X_3$ is K, $X_6$ is Q, and $X_7$ is R in $Hadru_{5-11}$ (SEQ ID NO: 9). Z is derived from the peptide $MCa_{1-2}$ (GD) and Z' is derived from the peptide $MCa_{10-20}$ (SEQ ID NO: 21). Preferably, $X_6$, $X_3$ and $X_7$, $X_6$ and $X_7$, $X_3$ and $X_7$ or $X_6$ are basic amino acids, and/or $X_1$ or $X_7$, or both, are hydrophobic amino acids. In preferred embodiments, all the hydrophobic amino acids of said peptide (I) are $J^1$. Preferably, $X_2$ and $X_5$ are L or $X_2$ is I and $X_5$ is L.

Preferably, the sequence $X_1-X_2-X_3-X_4-X_5-X_6-X_7$ is chosen from the group consisting of SEQ ID NO: 3 to 20 and the sequences wherein one, two, three, four, five, six or seven amino acids of SEQ ID NO: 3 to 20 have been substituted with a different amino acid. In preferred embodiments, at least the cysteine (C) in position 1 ($X_1$), the histidine (H) in position 4 ($X_4$) and/or the lysine (K) in position 6 ($X_6$) of SEQ ID NO: 3 to 20 have been substituted with a different amino acid. In some embodiments, the cysteine (C) in position 1 is substituted with 2-amino butyric acid. In some preferred embodiments, the sequence $X_1-X_2-X_3-X_4-X_5-X_6-X_7$ is chosen from the group consisting of SEQ ID NO: 3, 9, 12 and 18.

Preferably, Z consists of a sequence of 1 to 4 amino acids. In some embodiments Z consists of 2, 3 or 4 amino acids. Preferably, Z comprises one or two acidic amino acids (D, E). In some embodiments, Z is chosen from GD, GA, KD and SEKD.

Preferably, Z' is no amino acid or consists of the sequence (III) $Z'_1-Z'_2-Z'_3-Z'_4-Z'_5-Z'_6-Z'_7-Z'_8-Z'_9-Z'_{10}-Z'_{11}$, wherein:
 $Z'_1$ is J,
 $Z'_2$ is B, J, N, Q or no amino acid,
 $Z'_3$ is N, Q, P, G, J, D, E or no amino acid
 $Z'_4$ is N, Q, D, E or no amino acid,
 $Z'_5$ is N, Q, B or no amino acid,
 $Z'_6$ is N, Q, P, G, J, D, E or no amino acid,
 $Z'_7$ is J or no amino acid,
 $Z'_8$ is J or no amino acid,
 $Z'_9$ is S, G, T, J, Q, N or no amino acid, Z'$_{10}$ is B or no amino acid, Z'$_{11}$ is B or no amino acid, and wherein Z' does not comprise any internal deletion other than the deletion of Z'$_2$ to Z'$_9$, Z'$_3$ to Z'$_6$, or one or more of Z'$_3$, Z'$_6$ and Z'$_9$.

In preferred embodiments, Z' is chosen from the group consisting of:

SEQ ID NO: 21 to 35, the sequences wherein one, two, three, four, five, six, seven, eight, nine, ten or eleven amino acids of SEQ ID NO: 21 to 35 have been substituted. Preferably, the cysteine (C) residues in positions 7 (Z'$_7$), and eventually also the cysteine(s) in position 1 (Z'$_1$) and/or 8 (Z'$_8$) are substituted with Abu, the glutamic acid residue in position 3 (Z'$_3$) is substituted with N, Q, P, G or J, the aspartic acid residue in position 6 (Z'$_6$) is substituted with N, Q, P, G or J, and/or the serine or glycine residue in position 9 (Z'$_9$) is replaced with J, Q or N, and the N-terminal fragments of said sequences which consist of the first 1 to 10 amino acids of said sequences, and the fragments wherein the residues in positions 2 to 9 (Z'$_2$ to Z'$_9$), the residues in positions 3 to 6 (Z'$_3$ to Z'$_6$), or one or more of the residues in position 3 (Z'$_3$), 6 (Z'$_6$) and 9 (Z'$_9$) of SEQ ID NO: 21 to 35 have been deleted.

In preferred embodiments, the peptide (I) has a net charge of zero, +1 or +2. Preferably, X$_1$ to X$_7$ and Z together have a net charge of zero.

The peptide (II) which consists of 8 to 20 amino acids is derived from the maurocalcine peptides 6 to 25 and 18 to 33. The peptide MCa$_{6-25}$ has the amino acid sequence of SEQ ID NO: 106. The peptide MCa$_{18-33}$ has the amino acid sequence of SEQ ID NO: 107. The peptide MCa$_{18-25}$ has the sequence SEQ ID NO: 108. U is derived from the peptide MCa$_{6-17}$ (SEQ ID NO: 109) and U' is derived from the peptide MCa$_{26-33}$ (SEQ ID NO: 110).

In some embodiments X$^a$ is chosen from S, G, T and A. In other embodiments, X$^a$ is chosen from J, Q and N.

Preferably, the central sequence X$^a$BBJBBBX$^b$ is chosen from: SKKCKRR and GKKCKRR (SEQ ID NO: 108 and 111), and the sequences wherein one, two, three, four, five, six or seven amino acids of SEQ ID NO: 108 and 111 have been substituted with a different amino acid.

Preferably, U is no amino acid or consists of the sequence (IV) U$_1$-U$_2$-U$_3$-U$_4$-U$_5$-U$_6$-U$_7$-U$_8$-U$_9$-U$_{10}$-U$_{11}$-U$_{12}$, wherein:

U$_1$ is J or another amino acid different from K, R, S, T, D and E,

U$_2$ is J or no amino acid

U$_3$ is J, B, another amino acid, or no amino acid,

U$_4$ is J, B, another amino acid, or no amino acid,

U$_5$ is J or no amino acid,

U$_6$ is B, N, Q, J or no amino acid,

U$_7$ is N, Q, P, G, J, D, E or no amino acid,

U$_8$ is N, Q, D, E or no amino acid,

U$_9$ is N, Q, B or no amino acid,

U$_{10}$ is N, Q, P, G, J, D, E or no amino acid,

U$_{11}$ is J or no amino acid,

U$_{12}$ is J or no amino acid, and wherein U does not comprise any internal deletion other than the deletion of U$_7$ to U$_{10}$ or the deletion of U$_7$, U$_{10}$, or both residues.

In preferred embodiments, U is chosen from:

the sequences SEQ ID NO: 109 and 112 to 115, the sequences wherein one, two, three, four, five, six, seven, eight, nine, ten, eleven or twelve amino acids of SEQ ID NO: 109 and 112 to 115 have been substituted with a different amino acid. In preferred embodiments, the cysteine (C) residues in positions 11 (U$_{11}$) and 12 (U$_{12}$), and eventually also the cysteine in position 5 (U$_5$) are substituted with Abu; the glutamic acid residue (E) in position 7 (U$_7$) is substituted with N, Q, P, G or J, the aspartic acid residue (D) in position 10 (U$_{10}$) is substituted with N, Q, P, G or J, the histidine (H) residue in position 1 (U$_1$), and/or the lysine residue in position 3 (U$_3$) is substituted with a different amino acid, and the N-terminal fragments of said sequences which consist of the first 1 to 11 amino acids of said sequences, and the fragments wherein the residues in positions 7 to 10 (U$_7$ to U$_{10}$), the glutamic acid residue in position 7 (U$_7$), the aspartic acid residue in position 10 (U$_{10}$) or both residues of SEQ ID NO: 109 and 112 to 115 have been deleted. In some embodiments, the N-terminal fragment consists of the first five amino acids of said sequences.

Preferably, U' is no amino acid or consists of the sequence U'$_1$-U'$_2$-U'$_3$-U'$_4$-U'$_5$-U'$_6$-U'$_7$-U'$_8$, wherein:

U'$_1$ is O,

U'$_2$ is N, Q, or no amino acid,

U'$_3$ is P, J or no amino acid,

U'$_4$ is J, D, E or no amino acid,

U'$_5$ is B or no amino acid,

U'$_6$ is B or no amino acid,

U'$_7$ is J or no amino acid, and

U'$_8$ is B or no amino acid, wherein U' does not comprise any internal deletion other than the deletion of U'$_1$ to U'$_4$.

In preferred embodiments, U' is chosen from:

the sequences SEQ ID NO: 110 and 116 to 118, the sequences wherein one, two, three, four, five, six, seven or eight amino acids of SEQ ID NO: 110 and 116 to 118 have been substituted with a different amino acid. In preferred embodiments, the cysteine (C) residue in position 7 (U'$_7$) is substituted with Abu and/or the glutamic acid residue in position 4 (U'$_4$) is substituted with J, P, Q, N or G, and the N-terminal fragments of said sequences which consist of the first 1 to 7 amino acids of said sequences and the fragments of said sequences wherein the residues in positions 1 to 4 (U'$_1$ to U'$_4$) of SEQ ID NO: 110 and 116 to 118 have been deleted.

In preferred embodiments of the invention, the peptide (I) has a sequence selected from the group consisting of: SEQ ID NO: 2, 3 and 36 to 43 and the sequences which have at least 60% similarity to the full length sequence of any of SEQ ID NO: 2, 3 and 36 to 43. In some embodiments, the sequences have at least 70%, 80% or 90% similarity with said full-length sequences. In some embodiments, said sequences have also at least 40% identity, preferably at least 50%, 60%, 70% or 80% identity with said full-length sequences.

In preferred embodiments of the invention, the peptide (II) has a sequence selected from the group consisting of: SEQ ID NO: 106, 107, 108 and 119 and the sequences which have at least 60% similarity to the full length sequence of any of SEQ ID NO: 106, 107, 108 and 119. In some embodiments, the sequences have at least 70%, 80% or 90% similarity with said full-length sequences. In some embodiments, said sequences have also at least 40% identity, preferably at least 50%, 60%, 70% or 80% identity with said full-length sequences.

Percentage (%) sequence identity is defined as the percentage of amino acid residues in a candidate sequence that are identical with residues in the given listed sequences (referred to by SEQ ID NO: X) after aligning the sequences and introducing gaps if necessary, to achieve the maximum sequence identity and not considering any conservative substitutions as part of the sequence identity. Sequence identity is preferably calculated over the entire length of the respective sequences.

Percentage (%) sequence similarity is defined as the percentage of amino acid residues in a candidate sequence that are identical with residues in the given listed sequences (referred to by SEQ ID NO: X) after aligning the sequences and introducing gaps if necessary, to achieve the maximum sequence identity and considering any conservative substitutions as part of the sequence identity. Sequence similarity is preferably calculated over the entire length of the respective sequences.

Alignment for purposes of determining percent amino acid sequence identity/similarity can be achieved in various ways known to a person of skill in the art, for instance using publicly available computer software such as BLAST (Altschul et al., J. Mol. Biol., 1990, 215, 403-). When using such software, the default parameters, e.g., for gap penalty and extension penalty, are preferably used. For amino acid sequences, the BLASTP program uses as default a word length (W) of 3 and an expectation (E) of 10.

In some embodiments, the peptides according to the present invention comprise conservative amino acid replacements which, for example, may be between amino acids within the following groups: G, A, S and T; D and E; R, H and K; N and Q; I, L and V; F, Y and W; C and 2-aminobutyric acid.

In some embodiments, the peptide comprises a unique free cysteine (cysteine not linked to another cysteine via a disulfide bond). Preferably, said unique free cysteine is at the N- or C-terminus of the peptide. Preferably, the other cysteine residues of maurocalcine which are not linked via a disulfide bond are replaced with 2-amino butyric acid. In preferred embodiments of the present invention, said unique free cysteine is used for coupling the cargo covalently to the peptide by a disulphide, thioether or thiol-maleimide linkage.

In other embodiments, the peptide comprises two cysteines which are linked via a disulfide bond (intramolecular disulphide bond). Preferably, the peptide (I) comprises at least the residues $Z'_1$ to $Z'_8$ of the sequence Z', with or without the residue(s) $Z'_3$, $Z'_6$, and/or $Z'_9$, $Z'_2$ to $Z'_9$, or $Z'_3$ to $Z'_6$, and $X_1$ and $Z'_8$ or $X_1$ and $Z'_1$ are cysteine residues which are linked via a disulfide bond. Preferably, the peptide (11) comprises at least the residues $U_5$ to $U_{12}$ of the sequence U and $U_5$ and the residue J of the central sequence of said peptide II are cysteine residues which are linked via a disulfide bond. The presence or absence of disulphide bonds can be advantageous to improve the cell penetration efficiency and/or the conformational stability of the peptides according to the present invention.

The peptide according to the invention may consist of L-amino acids, D-amino acids or mixtures thereof. Preferably, the peptides comprise D-amino acids. In preferred embodiments of the present invention, the peptide consists of D-amino acids. Peptides comprising D-amino acids have the advantage of being more stable in vivo due to their increased resistance to proteolytic cleavage.

Preferred peptides (I) according to the present invention have a sequence selected from the group consisting of: SEQ ID NO: 2 to 105, 148, 150, 152, 154, 158, 160, 162, 164, 166, 168 and 170. More preferred peptides (I) are selected from the group consisting of SEQ ID NO: 2, 3, 9, 12, 18, 36, 37, 44, 46, 66, 150, 152 and 154.

Preferred peptides (II) according to the present invention have a sequence selected from the group consisting of: SEQ ID NO 106 to 108, 111 and 119 to 133.

In preferred embodiments, the peptide is modified. The modifications include esterification, glycosylation, acylation such as acetylation or linking myristic acid, amidation, phosphorylation, biotinylation, PEGylation, coupling of farnesyl and similar modifications which are well-known in the art. Modifications can be introduced at the the N-terminus, the C-terminus of the peptide or if deemed suitable, also to any amino acid other than the terminal amino acids (e.g. farnesyl coupling to a cysteine side chain). Conversion of the acid function on the C-terminus into an aldehyde and alkylation of the thiol function of a cysteine residue are used for chemoselective ligation or the formation of reduced peptide bonds.

Preferably, the peptide is used as a complex comprising at least the peptide and a molecular cargo.

The use according to the present invention comprises contacting the complex comprising the peptide and the cargo with cells, in vitro or in vivo, wherein the complex crosses the plasma membrane of the cells and the cargo is delivered into the cells, in vitro or in vivo. Preferably, the cargo is delivered into the cytoplasm and/or the nucleus of the cells.

The cargo can be a small molecule, a macromolecule or a particle. In a preferred embodiment, the cargo is selected from the group consisting of: oligonucleotides including antisense oligonucleotides, peptide nucleic acids (PNAs), small interfering RNAs, locked nucleic acids (LNAs), phosphorodiamidate morpholino oligonucleotides (PMOs) and decoy DNA molecules; plasmids; cDNAs; aptamers including DNA, RNA or peptide aptamers; peptides; proteins including antibodies; small and large chemical compounds including bioactive substances like drugs for the treatment of human, animal or plant diseases; labels such as fluorescent or radioactive molecules; imaging agents; liposomes, micelles and nanoparticles including liposomes, micelles and nanoparticles carrying an active agent such as nanocarriers. For example, the active agent can be encapsulated into the particles or grafted onto said particles by means well-known in the art. It is within the present invention that the complex comprises more than one peptide according to the present invention, i.e., a plurality of such peptides, whereby the plurality of the peptides may comprise a plurality of the same or of different peptides. Also, the complex according to the present invention may also comprise more than one cargo molecule, whereby the plurality of the cargo molecules may comprise a plurality of the same or of different cargo molecules.

In a preferred embodiment, the cargo is covalently or non-covalently bound to the peptide of the invention.

The cargo may be coupled to the peptide, directly or indirectly. Indirect coupling of the cargo to the peptide may be through a linker that is attached to the peptide of the invention. Linkers, also named spacers, that can be used to physically separate the peptide of the invention to the cargo are known in the art and include a peptide bond, an amino acid, a peptide of appropriate length or a different molecule providing the desired feature. The linker may be attached to the the N-terminus, the C-terminus of the peptide or if deemed suitable, also to any amino acid other than the terminal amino acids.

The peptide of the invention can be chemically linked to the cargo by covalent bonds using standard conjugation techniques. The cargo can be linked to the N-terminus, the C-terminus of the peptide, or if applicable, to any amino acid other than the terminal amino acids. Functional groups, modifications also called derivatizations or a linker may also be introduced into the peptide for conjugating the peptide to the cargo. Such covalent bonds are preferably formed between either a suitable reactive group of the peptide and the cargo and more preferably between a terminus of the peptide according to the present invention and the cargo molecule(s). Depending on the chemical nature of the cargo molecules, the moiety, group or radical with which such covalent bond is formed varies and it is within the skills of a person of the art to create such bond. Chemical linkage may be via a disulphide bond, thioether, thiol-maleimide or amide linkage. Other ways of linking the peptide to the cargo include use of a C-terminal aldehyde to form an oxime, use of a click reaction or formation of a morpholino linkage with a basic amino acid on the peptide. For coupling the peptide to the cargo using click chemistry, an alcyne or azido function may be added to the peptide using the N-alpha-(9-Fluorenylmethyloxycarbonyl)-L-propargylglycine, (S)-2-(Fmoc-amino)-4-pentynoic acid or N-alpha-(9-Fluorenylmethyloxycarbonyl)-4-azido-L-homoalanine or (S)-2-(9-Fluorenylmethyloxycarbonylamino)-4-azidobutanoic acid reagents. This type of construct is produced by well-known peptide chemical synthesis methods, preferably by solid phase synthesis.

In addition, when the cargo is a peptide or a protein including an antibody, the complex may be a fusion protein/peptide in which the cargo is fused to the N-terminus or the C-terminus of the peptide of the invention, directly or via a peptide spacer. This complex is produced by making a fusion in frame of a nucleotide sequence encoding the peptide of the invention to a nucleotide sequence encoding the peptide/protein cargo, and expressing the resulting chimeric gene using standard recombinant DNA techniques. The resulting fusion protein/peptide is of heterologous origin, i.e., it is different from naturally occurring peptides or proteins such as maurocalcine or other toxins of the same family.

The peptide can also be bound to the cargo (molecule or particle carrying the molecule) via non-covalent bounds such as ionic bonds, hydrogen bonds or hydrophobic interactions or a combination of such bonds. Non-limitative examples include streptavidine-biotin interactions between a biotinylated peptide and a cargo (for example nanoparticles like Quantum dots) that is conjugated to streptavidine or a biotinylated cargo and a peptide that is conjugated to streptavidine.

In some embodiments, the complex further comprises a targeting moiety, for example a targeting peptide for targeting the complex to specific cell types.

In a preferred embodiment, the cargo is linked covalently to the peptide of the invention via a cysteine linker that is attached to the N-terminus or the C-terminus of the peptide of the invention. Preferably, the cysteine residues of the peptide are replaced with 2-amino butyric acids, so that the cysteine linker is the unique cysteine of the peptide which is used for coupling the cargo covalently to the peptide by a linkage such a disulphide, thioether or thiol-maleimide linkage.

Examples of such peptides are SEQ ID NO: 134 to 139, 149, 151, 153, 155, 157, 159, 161, 163, 165, 167, 169 and 171. Preferred peptides (I) are selected from the group consisting of: SEQ ID NO: 134-136, 151, 153, 155 and 157.

The invention provides a peptide according to the present invention. Peptides according to the present invention may be provided in isolated or purified form, with or without the cargo.

The invention provides a complex comprising a peptide of the invention and a cargo.

The invention provides a pharmaceutical composition comprising (1) a complex comprising a peptide of the invention and an active agent, and (2) a pharmaceutically acceptable carrier.

The pharmaceutical composition comprises a therapeutically effective amount of the complex, e.g., sufficient to show benefit to the individual to whom it is administered. The pharmaceutical composition is formulated for administration by a number of routes, including but not limited to oral, parenteral and nasal.

The invention provides a method of treatment of a patient or subject in need for treatment for a disease condition, comprising the step of administering a therapeutically effective amount of a complex comprising a peptide of the invention and an active agent to the patient or subject.

The invention provides also a complex comprising a peptide of the invention and an active agent for treating a disease.

The active agent is a pharmaceutical agent or therapeutic capable of preventing, treating or ameliorating a disease in humans or animals. The active agent may be a protein including an antibody, an oligonucleotide including an antisense oligonucleotide, peptide nucleic acid (PNA), small interfering RNA, locked nucleic acids (LNA), phosphorodiamidate morpholino oligonucleotides (PMO) and decoy DNA molecule, a plasmid, an aptamer including DNA, RNA or peptide aptamer, a small or large chemical drug, or mixtures thereof. In particular, the active agent may be a chemotherapeutic drug used for treating cancer. Coupling anti-tumoral drugs to the cell penetrating peptides represent a valuable strategy to overcome drug resistance. The active agent is also an antigen or a nucleic acid molecule encoding said antigen (DNA vaccine) for use as a vaccine for the prevention or the treatment of an infectious disease or a cancer. The complex may comprise particles like nanoparticles, micelles or liposomes carrying both the peptide(s) and the active(s) agent(s).

Diseases to be prevented, treated or ameliorated may include any disease where improved penetration of the plasma and/or nuclear membrane by a pharmaceutical or therapeutical molecule may lead to an improved therapeutic effect. Diseases to be treated may include cancer, genetic, neurological, cardiovascular, metabolic, inflammatory, autoimmune and infectious diseases.

The invention provides a detection reagent, for example a diagnostic reagent, comprising a complex comprising a peptide of the invention and a detection agent. Preferably, the detection agent is covalently or non-covalently bound to the peptide. Detection agents are known in the art and include but are not limited to antibodies and oligonucleotide probes that are used for the detection (qualitative or quantitative detection) of an intracellular target, for example a protein or a nucleic acid target. When the intracellular target is associated with a disease (e.g., diagnostic marker), the detection agent is a diagnostic agent. According to a preferred embodiment, the complex further comprises a detectable moiety that produces a detectable signal when the intracellular target reacts with the detection agent. For example, the detectable moiety can be a fluorescent reporter system.

The invention provides a method of detecting an intracellular target, comprising:
  contacting the detection reagent of the invention with cells, in vitro or in vivo, wherein the detection reagent is capable of reacting with an intracellular target, and
  detecting the intracellular target that has reacted with the reagent, by any appropriate means.

The invention provides a method of diagnosis a disease, comprising:
  contacting the diagnostic reagent of the invention with cells, in vitro or in vivo, wherein the diagnostic reagent is capable of reacting with an intracellular diagnostic marker, and
  detecting the intracellular diagnostic marker that has reacted with the reagent, by any appropriate means.

The invention provides an imaging reagent, comprising a complex comprising a peptide of the invention and a label or a contrast agent. Preferably, the label or contrast agent is covalently or non-covalently bound to the peptide.

In optical imaging methods, the imaging reagent comprises a complex comprising a peptide of the invention and a label. The label is any molecule that produces a signal that can be detected in situ in living cells or tissues. The label can be a fluorescent molecule. This imaging reagent can be applied in optical imaging methods for research or diagnostic purposes.

In magnetic resonance imaging (MRI) the imaging reagent comprises a complex comprising a peptide of the invention and a contrast agent, usually a paramagnetic contrast agent (usually a gadolinium compound) or a superparamagnetic contrast agent (iron oxide nanoparticles). MRI was primarily used in medical imaging to demonstrate pathological or other physiological alteration of living tissues.

In positron emission tomography (PET), the imaging reagent comprises a complex comprising a peptide of the invention and a short-lived radioactive tracer isotope which has been chemically incorporated into a metabolically active molecule (usually a sugar, fluorodeoxyglucose, FDG) and which decays by emitting a positron. PET is a nuclear medicine imaging technique which produces a three-dimensional image or map of functional processes in the body.

The invention provides a nucleic acid molecule (DNA, RNA) comprising a nucleotide sequence encoding the peptide or the fusion peptide/protein according to the present invention.

The invention provides a nucleic acid recombinant vector comprising said nucleic acid molecule. Preferably, said recombinant vector is an expression vector comprising a regulatory sequence (promoter) operably linked to said nucleotide sequence, wherein the vector is capable of expressing the peptide or fusion peptide/protein of the invention when transfected or transformed into a host cell (mammalian, bacterial or fungal). Recombinant vectors include usual vectors used in genetic engineering and gene therapy including for example plasmids and viral vectors.

The invention provides a cell transformed with said recombinant vector.

The nucleic acid molecule, vector, cell of the invention are useful for the production of the peptide or fusion peptide/protein of the invention using well-known recombinant DNA techniques.

The invention provides a kit comprising one or more of:
  a peptide of the invention,
  a complex of the invention,
  a nucleic acid molecule, recombinant vector, cell transformant of the invention.
  a pharmaceutical composition of the invention, and
  a detection, diagnostic or imaging reagent of the invention.

TABLE I

Peptide sequences

| Peptide | Variant | Sequence | SEQ ID NO: |
|---|---|---|---|
| $MCa_{1-33}$ | | GDCLPHLKLCKENKDCCSKKC KRRGTNIEKRCR | 1 |
| $MCa_{1-20}$ | | GDCLPHLKLCKENKDCCSKK | 2 |
| $MCa_{3-9}$ | | CLPHLKL | 3 |
| | H6A | CLPALKL | 4 |
| | K8A | CLPHLAL | 5 |
| $Opi/IpTx_{3-9}$ | | CLPHLKR | 6 |
| | H6A | CLPALKR | 7 |
| | K8A | CLPHLAR | 8 |
| $HadruCa_{5-11}$ | | CIKHLQR | 9 |
| | H6A | CIKALQR | 10 |
| | K8A | CIKHLAR | 11 |
| $MCa_{3-9}$ | C3Abu | aLPHLKL | 12 |
| | C3Abu/H6A | aLPALKL | 13 |
| | C3Abu/K8A | aLPHLAL | 14 |

TABLE I-continued

Peptide sequences

| Peptide | Variant | Sequence | SEQ ID NO: |
|---|---|---|---|
| Opi/IpTx$_{3-9}$ | C3Abu | aLPHLKR | 15 |
| | C3Abu/H6A | aLPALKR | 16 |
| | C3Abu/K8A | aLPHLAR | 17 |
| HadruCa$_{5-11}$ | C5Abu | aIKHLQR | 18 |
| | C5Abu/H8A | aIKALQR | 19 |
| | C5Abu/K10A | aIKHLAR | 20 |
| MCa$_{10-20}$ | | CKENKDCCSKK | 21 |
| | C10, 16, 17Abu | aKENKDaaSKK | 22 |
| | C10, 16Abu | aKENKDaCSKK | 23 |
| Opi$_{10-20}$ | | CKENNDCCSKK | 24 |
| | C10, 16, 17Abu | aKENNDaaSKK | 25 |
| | C10, 16Abu | aKENNDaCSKK | 26 |
| IpTx$_{10-20}$ | | CKADNDCCGKK | 27 |
| | C10, 16, 17Abu | aKADNDaaGKK | 28 |
| | C10, 16Abu | aKADNDaCGKK | 29 |
| HemiCa$_{10-20}$ | | CKADKDCCSKK | 30 |
| | C10, 16, 17Abu | aKADKDaaSKK | 31 |
| | C10, 16Abu | aKADKDaCSKK | 32 |
| HadruCa$_{12-22}$ | | CRENKDCCSKK | 33 |
| | C12-18-19Abu | aRENKDaaSKK | 34 |
| | C12-18-Abu | aRENKDaCSKK | 35 |
| MCa$_{1-9}$ | | GDCLPHLKL | 36 |
| MCa$_{1-15}$ | | GDCLPHLKLCKENKD | 37 |
| MCa$_{1-15/\Delta12-15}$ | | GDCLPHLKLCK | 38 |
| MCa$_{1-15/\Delta12}$ | | GDCLPHLKLCKNKD | 39 |
| MCa$_{1-15/\Delta15}$ | | GDCLPHLKLCKENK | 40 |
| MCa$_{1-20/\Delta12-15}$ | | GDCLPHLKLCKCCSKK | 41 |
| MCa$_{1-20/\Delta12}$ | | GDCLPHLKLCKNKDCCSKK | 42 |
| MCa$_{1-20/\Delta15}$ | | GDCLPHLKLCKENKCCSKK | 43 |
| MCa$_{1-9}$ | C3Abu | GDaLPHLKL | 44 |
| | D2A/C3Abu | GAaLPHLKL | 45 |
| MCa$_{1-15}$ | C3, 10Abu | GDaLPHLKLaKENKD | 46 |
| | D2A/C3, 10Abu | GAaLPHLKLaKENKD | 47 |
| | H6A/C3, 10Abu | GDaLPALKLaKENKD | 48 |
| | K8A/C3, 10Abu | GDaLPHLALaKENKD | 49 |
| | E12A/C3, 10Abu | GDaLPHLALaKANKD | 50 |
| | D15A/C3, 10Abu | GDaLPHLALaKENKA | 51 |

TABLE I-continued

Peptide sequences

| Peptide | Variant | Sequence | SEQ ID NO: |
|---|---|---|---|
| MCa$_{1-15/\Delta 12-15}$ | C3, 10Abu | GDaLPHLKLaK | 52 |
| | D2A/C3, 10Abu | GAaLPHLKLaK | 53 |
| | H6A/C3, 10Abu | GDaLPALKLaK | 54 |
| | K8A/C3, 10Abu | GDaLPHLALaK | 55 |
| MCa$_{1-15/\Delta 12}$ | C3, 10Abu | GDaLPHLKLaKNKD | 56 |
| | D2A/C3, 10Abu | GAaLPHLKLaKNKD | 57 |
| | H6A/C3, 10Abu | GDaLPALKLaKNKD | 58 |
| | K8A/C3, 10Abu | GDaLPHLALaKNKD | 59 |
| | D15A/C3, 10Abu | GDaLPHLALaKNKA | 60 |
| MCa$_{1-15/\Delta 15}$ | C3, 10Abu | GDaLPHLKLaKENK | 61 |
| | D2A/C3, 10Abu | GAaLPHLKLaKENK | 62 |
| | H6A/C3, 10Abu | GDaLPALKLaKENK | 63 |
| | K8A/C3, 10Abu | GDaLPHLALaKENK | 64 |
| | E12A/C3, 10Abu | GDaLPHLKLaKANK | 65 |
| MCa$_{1-20}$ | C3, 10, 16, 17Abu | GDaLPHLKLaKENKDaaSKK | 66 |
| | D2A/C3, 10, 16, 17Abu | GAaLPHLKLaKENKDaaSKK | 67 |
| | H6A/C3, 10, 16, 17Abu | GDaLPALKLaKENKDaaSKK | 68 |
| | K8A/C3, 10, 16, 17Abu | GDaLPHLALaKENKDaaSKK | 69 |
| | D15A/C3, 10, 16, 17Abu | GDaLPHLKLaKENKAaaSKK | 70 |
| | E12A/C3, 10, 16, 17Abu | GDaLPHLKLaKANKDaaSKK | 71 |
| MCa$_{1-20/\Delta 12-15}$ | C3, 10, 16, 17Abu | GDaLPHLKLaKaaSKK | 72 |
| | D2A/C3, 10, 16, 17Abu | GAaLPHLKLaKaaSKK | 73 |
| | H6A/C3, 10, 16, 17Abu | GDaLPALKLaKaaSKK | 74 |
| | K8A/C3, 10, 16, 17Abu | GDaLPHLALaKaaSKK | 75 |
| MCa$_{1-20/\Delta 12}$ | C3, 10, 16, 17Abu | GDaLPHLKLaKNKDaaSKK | 76 |
| | D2A/C3, 10, 16, 17Abu | GAaLPHLKLaKNKDaaSKK | 77 |
| | H6A/C3, 10, 16, 17Abu | GDaLPALKLaKNKDaaSKK | 78 |
| | K8A/C3, 10, 16, 17Abu | GDaLPHLALaKNKDaaSKK | 79 |
| | D15A/C3, 10Abu | GDaLPHLKLaKNKAaaSKK | 80 |
| MCa$_{1-20/\Delta 15}$ | C3, 10, 16, 17Abu | GDaLPHLKLaKENKaaSKK | 81 |
| | D2A/C3, 10, 16, 17Abu | GAaLPHLKLaKENKaaSKK | 82 |
| | H6A/C3, 10, 16, 17Abu | GDaLPALKLaKENKaaSKK | 83 |
| | K8A/C3, 10, 16, 17Abu | GDaLPHLALaKENKaaSKK | 84 |
| | E12A/C3, 10, 16, 17Abu | GDaLPHLKLaKANKaaSKK | 85 |
| MCa$_{1-20F}$ | C10, 16Abu | GDCLPHLKLaKENKDaCSKK | 86 |
| | D2A/C10, 16Abu | GACLPHLKLaKENKDaCSKK | 87 |
| | H6A/C10, 16Abu | GDCLPALKLaKENKDaCSKK | 88 |

TABLE I-continued

Peptide sequences

| Peptide | Variant | Sequence | SEQ ID NO: |
|---|---|---|---|
| | K8A/C10, 16Abu | GDCLPHLALaKENKDaCSKK | 89 |
| | D15A/C10, 16Abu | GDCLPHLKLaKENKAaCSKK | 90 |
| | E12A/C10, 16Abu | GDCLPHLKLaKANKDaCSKK | 91 |
| MCa$_{1-20/\Delta 12-15}$ | C10, 16, Abu | GDCLPHLKLaKaCSKK | 92 |
| | D2A/C10, 16Abu | GACLPHLKLaKaCSKK | 93 |
| | H6A/C10, 16, Abu | GDCLPALKLaKaCSKK | 94 |
| | K8A/C10, 16Abu | GDCLPHLALaKaCSKK | 95 |
| MCa$_{1-20/\Delta 12}$ | C10, 16Abu | GDCLPHLKLaKNKDaCSKK | 96 |
| | D2A/C10, 16Abu | GACLPHLKLaKNKDaCSKK | 97 |
| | H6A/C10, 16Abu | GDCLPALKLaKNKDaCSKK | 98 |
| | K8A/C10, 16Abu | GDCLPHLALaKNKDaCSKK | 99 |
| | D15A/C3, 10, 16Abu | GDCLPHLKLaKNKAaCSKK | 100 |
| MCa$_{1-20/\Delta 15}$ | C10, 16, Abu | GDCLPHLKLaKENKaCSKK | 101 |
| | D2A/C10, 16Abu | GACLPHLKLaKENKaCSKK | 102 |
| | H6A/C10, 16Abu | GDCLPALKLaKENKaCSKK | 103 |
| | K8A/C10, 16Abu | GDCLPHLALaKENKaCSKK | 104 |
| | E12A/C10, 16Abu | GDCLPHLKLaKANKaCSKK | 105 |
| MCa$_{6-25}$ | | HLKLCKENKDCCSKKCKRRG | 106 |
| MCa$_{18-33}$ | | SKKCKRRGTNIEKRCR | 107 |
| MCa$_{18-25}$ | | SKKCKRRG | 108 |
| MCa$_{6-17}$ | | HLKLCKENKDCC | 109 |
| MCa$_{26-33}$ | | TNIEKRCR | 110 |
| IpTxa$_{18-25}$ | | GKKCKRR | 111 |
| IpTxa$_{6-17}$ | | HLRCKADNDCC | 112 |
| Opi$_{6-17}$ | | HLKRCKENNDCC | 113 |
| Hemi$_{6-17}$ | | HLKLCKADKDCC | 114 |
| Hadru$_{8-19}$ | | HLQRCRENKDCC | 115 |
| IpTXa$_{26-33}$ | | TNAEKRCR | 116 |
| Opi1-Hemi-Hadru$_{26-33}$ | | TNPEKRCR | 117 |
| Opi2$_{26-33}$ | | ANPEKRCR | 118 |
| MCa$_{14-25}$ | | KDCCSKKCKRRG | 119 |
| MCa$_{18-33}$ | C21, 32Abu | SKKaKRRGTNIEKRaR | 120 |
| MCa$_{18-33\Delta 26-29}$ | C21, 32Abu | SKKaKRRGKRaR | 121 |
| MCa$_{6-25}$ | C10, 16, 17, 21Abu | HLKLaKENKDaaSKKaKRRG | 122 |
| MCa$_{6-25}$ | H6A/C10, 16, 17, 21Abu | ALKLaKENKDaaSKKaKRRG | 123 |
| MCa$_{6-25}$ | K8A/C10, 16, 17, 21Abu | HLALaKENKDaaSKKaKRRG | 124 |

TABLE I-continued

Peptide sequences

| Peptide | Variant | Sequence | SEQ ID NO: |
|---|---|---|---|
| MCa$_{6-25}$ | E12A/C10, 16, 17, 21Abu | HLKLaKANKDaaSKKaKRRG | 125 |
| MCa$_{6-25}$ | D15A/C10, 16, 17, 21Abu | HLKLaKENKAaaSKKaKRRG | 126 |
| MCa$_{6-25F}$ | C16, 17Abu | HLKLCKENKDaaSKKCKRRG | 127 |
| MCa$_{6-25F}$ | H6A/C16, 17Abu | ALKLCKENKDaaSKKCKRRG | 128 |
| MCa$_{6-25F}$ | K8A/C16, 17Abu | HLALCKENKDaaSKKCKRRG | 129 |
| MCa$_{6-25F}$ | E12A/C16, 17Abu | HLKLCKANKDaaSKKCKRRG | 130 |
| MCa$_{6-25F}$ | D15A/ C16, 17Abu | HLKLCKENKAaaSKKCKRRG | 131 |
| MCa$_{14-25}$ | C16, 17, 21Abu | KDaaSKKaKRRG | 132 |
| MCa$_{14-25}$ | D15A/C16, 17, 21Abu | KAaaSKKaKRRG | 133 |
| MCa$_{1-20}$-C | C3, 10, 16, 17Abu | GDaLPHLKLaKENKDaaSKKC | 134 |
| MCa$_{1-15}$-C | C3, 10Abu | GDaLPHLKLaKENKDC | 135 |
| MCa$_{1-9}$-C | C3Abu | GDaLPHLKLC | 136 |
| MCa$_{18-33}$-C | C21, 32Abu | SKKaKRRGTNIEKRaRC | 137 |
| MCa$_{6-25}$-C | C10, 16, 17, 21Abu | HLKLaKENKDaaSKKaKRRGC | 138 |
| MCa$_{14-25}$-C | C16, 17, 21Abu | KDaaSKKaKRRGC | 139 |
| MCa$_{1-33}$-C | C3, 10, 16, 17, 21, 32Abu | GDaLPHLKLaKENKDaaSKKaKRRGTNIEKRaRC | 140 |
| MCa$_{8-33}$-C | C10, 16, 17, 21, 32Abu | KLaKENKDaaSKKaKRRGTNIEKRaRC | 141 |
| MCa$_{11-33}$-C | C16, 17, 21, 32Abu | KENKDaaSKKaKRRGTNIEKRaRC | 142 |
| MCa$_{14-33}$-C | C16, 17, 21, 32Abu | KDaaSKKaKRRGTNIEKRaRC | 143 |
| MCa$_{20-33}$-C | C21, 32Abu | KaKRRGTNIEKRaRC | 144 |
| MCa$_{22-33}$-C | C32Abu | KRRGTNIEKRaRC | 145 |
| MCa$_{25-33}$-C | C32Abu | GTNIEKRaRC | 146 |
| MCa$_{1-9}$-C | C3A | GDALPHLKLC | 147 |
| ImP$_{1-9}$ | C3Abu | GDaLPHLKR | 148 |
| Imp$_{1-9}$-C | C3Abu | GDaLPHLKRC | 149 |
| Had$_{1-11}$ | C5Abu | SEKDalKHLQR | 150 |
| Had$_{1-11}$-C | C5Abu | SEKDalKHLQRC | 151 |
| Had$_{3-11}$ | C5Abu | KDalKHLQR | 152 |
| Had$_{3-11}$-C | C5Abu | KDalKHLQRC | 153 |
| MCa$_{1-9}$ | C3W | GDWLPHLKL | 154 |
| MCa$_{1-9}$-C | C3W | GDWLPHLKLC | 155 |
| MCa$_{1-9}$-C | D2A, C3Abu | GAaLPHLKLC | 156 |
| MCa$_{3-9}$-C | C3Abu | aLPHLKLC | 157 |
| MCa$_{1-9}$ | C3Abu, H6W | GDaLPWLKL | 158 |
| MCa$_{1-9}$-C | C3Abu, H6W | GDaLPWLKLC | 159 |
| MCa$_{1-9}$ | C3Abu, L4W | GDaWPHLKL | 160 |

TABLE I-continued

Peptide sequences

| Peptide | Variant | Sequence | SEQ ID NO: |
|---|---|---|---|
| MCa$_{1-9}$-C | C3Abu, L4W | GDaWPHLKLC | 161 |
| MCa$_{1-9}$ | C3Abu, L7F | GDaLPHFKL | 162 |
| MCa$_{1-9}$-C | C3Abu, L7F | GDaLPHFKLC | 163 |
| MCa$_{1-9}$ | C3Abu, L9M | GDaLPHLKM | 164 |
| MCa$_{1-9}$-C | C3Abu, L9M | GDaLPHLKMC | 165 |
| MCa$_{1-9}$ | C3Q | GDQLPHLKL | 166 |
| MCa$_{1-9}$-C | C3Q | GDQLPHLKLC | 167 |
| MCa$_{1-9}$ | C3Abu, L9N | GDaLPHLKN | 168 |
| MCa$_{1-9}$-C | C3Abu, L9N | GDaLPHLKNC | 169 |
| MCa$_{1-9}$ | C3Abu, P5R, K8I | GDaLRHLIL | 170 |
| MCa$_{1-9}$-C | C3Abu, P5R, K8I | GDaLRHLILC | 171 |
| Tat-C | | GRKKRRQRRR-C | 172 |

MCa: Maurocalcine. IpTxa/Imp: Imperatoxine. Opi: Opicalcine. Hemi: Hemicalcine. Hadru/Had: Hadrucalcine For a better understanding of the invention and to show how the same may be carried into effect, there will now be shown by way of example only, specific embodiments, methods and processes according to the present invention with reference to the accompanying drawings in which:

FIG. 1 shows the efficacy of cargo penetration as a function of grafting position on MCaUF1-33. (A) Amino acid sequence of MCa$_F$ in single letter code. The positions of half-cystine residues and basic amino acids are highlighted in grey. Cys residues are numbered. Secondary structures (β strands) are indicated by arrows. The grey box is the sequence of homology of MCa with the dihydropyridine-sensitive Ca$_v$1.1 channel. (B) Amino acid sequences of unfolded MCa analogues in single letter code. Cys residues are replaced by isosteric 2-aminobutyric acid residues (Abu, in grey) to form MCa$_{UF1-33}$. An additional N-terminal (C-MCa$_{UF1-33}$) or C-terminal (MCa$_{UF1-33}$-C) Cys residue was added in two novel analogues competent for cargo grafting (shown in grey). (C) Comparison of cell penetration efficacy between Cy5-C-MCa$_{UF1-33}$ and MCa$_{UF1-33}$-C-Cy5 as determined by flow cytometry. CHO cells were incubated 2 hrs with 3 μM peptide, washed, and treated 5 min by 1 mg/ml trypsin before quantification of intracellular fluorescence.

FIG. 2 shows the primary structure of truncated MCa$_{UF}$ analogues and comparison of cell penetration efficacies. (A) Primary structures of truncated MCa$_{UF}$-C analogues and determination of their net positive charge and percentage of basic amino acid residues within the sequence. A total of 12 truncated MCa$_{UF}$-C analogues derived from MCa$_{UF1-33}$-C (SEQ ID NO: 140) were produced, three with truncations in C-terminus, seven in N-terminus, and two in both N- and C-termini: MCa$_{UF1-20}$-C (SEQ ID NO: 134); MCa$_{UF1-15}$-C (SEQ ID NO: 135); MCa$_{UF1-9}$-C (SEQ ID NO: 136); MCa$_{UF8-33}$-C (SEQ ID NO: 141); MCa$_{UF11-33}$-C (SEQ ID NO: 142); MCa$_{UF14-33}$-C (SEQ ID NO: 143); MCa$_{UF18-33}$-C (SEQ ID NO: 137); MCa$_{UF20-33}$-C (SEQ ID NO: 144); MCa$_{UF22-33}$-C (SEQ ID NO: 145); MCa$_{UF25-33}$-C (SEQ ID NO: 146); MCa$_{UF6-25}$-C (SEQ ID NO: 138); MCa$_{UF14-25}$-C (SEQ ID NO: 139). Positively charged residues are in grey (His residues were not counted), Abu residues that replace Cys residues are indicated. (B) Comparative cell penetration efficacy of all MCa$_{UF}$-C-truncated analogues that possess a net positive charge ≥+5. The non-truncated MCa$_{UF1-33}$-C-Cy5 analogue is shown as reference (black line) for the efficacy of cell penetration of all analogues. Experimental conditions: CHO cell incubation with 1 μM of each analogue for 2 hrs and fluorescence quantification by flow cytometry. (C) Same as (B) but for truncated MCa$_{UF}$-C-Cy5 analogues with positive net charge ≤+2.

FIG. 3 shows the extent of colocalization of the Cy5-labeled peptides with the rhodamine labeled plasma membrane. NS, non significant; *≤0.1; ≤0.05; and *≤0.001.

FIG. 4 shows the amiloride sensitivity of truncated MCa$_{UF}$ peptide cell entry. (A) Representative flow cytometry analyses of the effect of 5 mM amiloride on MCa$_{UF1-33}$-C-Cy5 (upper left panel), MCa$_{UF1-15}$-C-Cy5 (upper right panel), MCa$_{UF20-33}$-C-Cy5 (lower left panel) and MCa$_{UF18-33}$-C-Cy5 (lower right panel) entries. Numbers in red represent average decrease or increase in peptide entry upon amiloride treatment. Cells were treated 2 hrs with 3 μM peptide concentration with or without 5 mM amiloride. (B) Average effect of amiloride on mean cell entry of the truncated peptides. Positive values reflect increase in cell entries, whereas negative values indicate reduction in cell penetration.

FIG. 5 shows the dose-dependent cell penetration of truncated MCaUF peptides. (A) Representative example of the dose-dependent cell penetration of MCa$_{UF8-33}$-C-Cy5 in CHO cells as analyzed by flow cytometry. The peptide was incubated 2 hrs with the cells before analyses. There was no saturation of cell entry for a concentration up to 33 (B) Dose-dependent cell penetration of N-terminal truncated MCaUF peptides compared to $MCa_{UF1-33}$-C-Cy5 (open circle, dotted line). (C) Dose-dependent cell penetration of Cterminal truncated MCaUF peptides. (D) Dose-dependent cell penetration of N- and C-terminal truncated MCaUF peptides. Note the increase in scale for the penetration of these two peptides.

FIG. 6 shows the lack of pharmacology of the truncated peptides and reduced cell toxicity. (A) Effect of MCaF, MCaUF1-33 and truncated MCaUF peptides on [$^3$H]-ryanodine binding. Data were expressed as x-fold increase in binding induced by the peptides. (B) Effect of 1 and 10 µM MCaUF1-33 and truncated MCaUF peptides on CHO cell viability. Peptides were incubated 24 hrs with the cells in vitro.

FIG. 7 shows the dose-dependent cell penetration of the reference peptide $MCa_{UF1-9(Abu3)}$-C-Cy5 (closed circle) in F98 cells as analyzed by flow cytometry (A). B. Comparison of the reference peptide (closed circle) with the $MCa_{UF1-9(A3)}$-C-Cy5 peptide (open circle) in F98 cells.

FIG. 12 shows the dose-dependent cell penetration of the $MCa_{UF3-9\ (Abu3)}$-C-Cy5 (A) and $Imp_{UF1-9\ (Abu3)}$-C-Cy5 (B) peptides (open circle) in F98 cells compared to the reference peptide $MCa_{UF1-9(Abu3)}$-C-Cy5 (closed circle) as analyzed by flow cytometry.

FIG. 13 shows the dose-dependent cell penetration of the $MCa_{UF1-9(Abu3-M9)}$-C-Cy5(A) and $MCa_{UF1-9(Abu3-N9)}$-C-Cy5 (B) peptides (open circle) in F98 cells compared to the reference peptide $MCa_{UF1-9(Abu3)}$-C-Cy5 (closed circle) as analyzed by flow cytometry.

Figure 15:
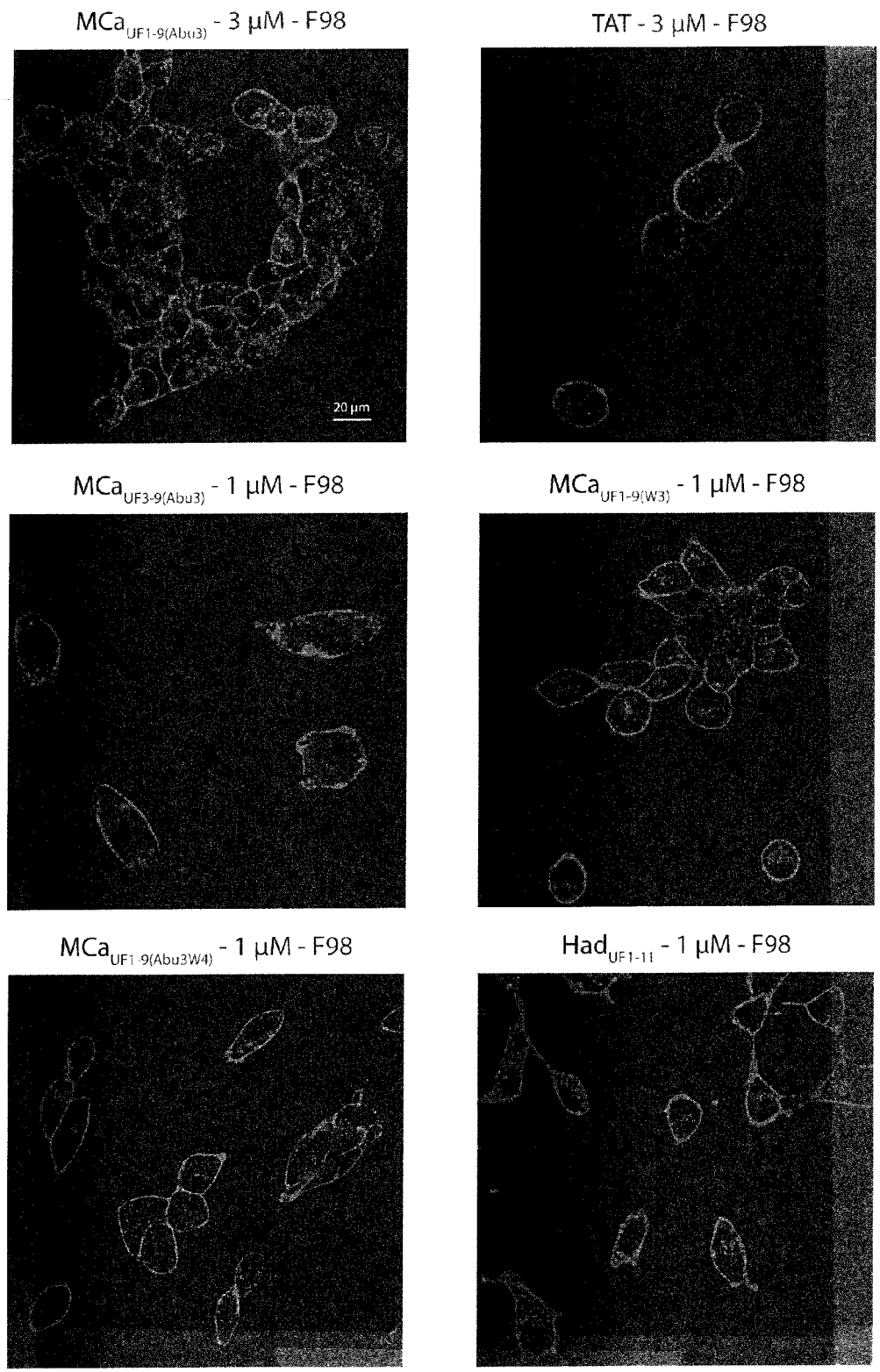

FIG. 15 shows the comparison of penetration of 3 µM $MCa_{UF1-9(Abu3)}$-C-Cy5, 1 µM derived peptides ($MCa_{UF3-9(Abu3)}$-C-Cy5, $MCa_{UF1-9(W3)}$-C-Cy5, $MCa_{UF1-9(Abu3-W4)}$-C-Cy5, $Had_{UF1-11(Abu5)}$-C-Cy5) and 3 µM TAT-C-Cy5 in F98 cell line as analyzed by confocal microscopy. The membrane is stained by Rhodamine-conjugated concanavalin A. The Cy5 labeled peptide that has penetrated into cells is visualized as intracellular foci. There will now be described by way of example a specific mode contemplated by the Inventors. In the following description numerous specific details are set forth in order to provide a thorough understanding. It will be apparent however, to one skilled in the art, that the present invention may be practiced without limitation to these specific details. In other instances, well known methods and structures have not been described so as not to unnecessarily obscure the description.

EXAMPLE 1

Experimental Procedures

1) Reagents

N-α-Fmoc-L-aminoacid, Wang-Tentagel resin and reagents used for peptide syntheses were obtained from Iris Biotech. Solvents were analytical grade products from Acros Organics. Cy5 maleimide mono-reactive dye was purchased from GE Healthcare.

2) Solid-Phase Peptide Syntheses

Chemical syntheses of MCa analogues were performed as previously described (Poillot et al., 2010). Briefly, analogues of MCa were chemically synthesized by the solid-phase method (Merrifield, R. B., 1969) using an automated peptide synthesizer (CEM© Liberty). Peptide chains were assembled stepwise on 0.24 mEq of Fmoc-D-Arg-Pbf-Wang-Tentagel resin using 0.24 mmol of N-α-fluorenylmethyloxycarbonyl (Fmoc) L-amino-acid derivatives. The side-chain protecting groups were: Trityl for Cys and Asn, tert-butyl for Ser, Thr, Glu and Asp, Pbf for Arg and tert-butylcarbonyl for Lys. Reagents were at the following concentrations: Fmoc-amino-acids (0.2 M Fmoc-AA-OH in dimethylformamide (DMF)), activator (0.5 M 2-(1H-benzotriazole-1-yl)-1,1,3,3-tetramethyluronium hexafluorophosphate in DMF), activator base (2M diisopropylethylamine in N-methyl-pyrrolidone (NMP)) and deprotecting agent (5% piperazine/0.1 M 1-hydroxybenzotriazole in DMF), as advised by PepDriver (CEM©). After peptide chain assembly, resins were treated 4 hrs at room temperature with a mixture of trifluoroacetic acid/water/triisopropylsilan (TIS)/dithiothreitol (DTT) (92.5/2.5/2.5/2.5). The peptide mixtures were then filtered and the filtrates were precipitated by adding cold t-butylmethyl ether. The crude peptides were pelleted by centrifugation (10.000×g, 15 min) and the supernatants were discarded. MCa analogues were purified by HPLC using a Vydac C18 column (218TP1010, 25×10 cm). Elutions of the peptides were performed with a 10-60% acetonitrile linear Gradient containing 0.1% trifluoroacetic acid. The purified fractions were analyzed by analytical RP-HPLC (Vydac C18 column 218TP104, 25×4.6 cm). All analogues were characterized by MALDI-TOF mass spectrometry.

3) Labeling of Peptide with Cy5

Each peptide was labeled with Cy5 according to the manufacturer's protocol (GE HEALTHCARE). Peptides were dissolved at 1 mg/ml in 0.1 M $Na_2CO_3$ buffer, pH 9.3. 300 µl of the solubilized peptides were added to Cy5-maleimide containing tubes. The mixtures were incubated during 2 hrs at room temperature and then purified by HPLC using an analytical Vydac C18 column. Elution of the Cy5-labeled peptides was performed with a 10-60% acetonitrile linear gradient containing 0.1% trifluoroacetic acid. The pure peak fractions were lyophilized and peptides quantified by UV spectrophotometer at 649 nm.

4) Cell Culture

Chinese hamster ovary (CHO) and F98 rat glioma cell lines (from ATCC) were maintained at 37° C. in 5% CO2 in F-12K nutrient medium (INVITROGEN) supplemented with 10% (v/v) heat-inactivated fetal bovine serum (INVITROGEN) and 10,000 units/ml streptomycine and penicillin (INVITROGEN) for the CHO cells, and 2% heat-inactivated fetal bovine serum and 100 units/ml streptomycine and penicillin for the F98 cells 5) MTT Assay Cells were seeded into 96-well micro plates at a density of approximately 8×104 cells/well. After 2 days of culture, the cells were incubated for 24 hrs at 37° C. with MCa analogues at a concentration of 10 µM. Control wells containing cell culture medium alone or with cells, both without peptide addition, were included in each experiment. 0.1% saponin was used as toxic agent for comparison. The cells were then incubated with 3-(4, 5-dimethylthiazol-2-yl)-2, 5-diphenyl-tetrazolium bromide (MTT) for 30 min. Conversion of MTT into purple colored MTT formazan by the living cells indicates the extent of cell viability. The crystals were dissolved with dimethyl sulfoxide (DMSO) and the optical density was measured at 540 nm using a microplate reader (Biotek ELx-800, MANDEL SCIENTIFIC INC.) for quantification of cell viability. All assays were run in triplicates.

6) Confocal Microscopy

For analysis of the subcellular localization of MCa-Cy5 analogues in living cells, cell cultures were incubated with the fluorescent peptides for 2 hrs, and then washed with phosphate-buffered saline (PBS) alone. The plasma membrane was stained with 5 µg/ml rhodamine-conjugated concanavalin A (MOLECULAR PROBES) for 5 min. Cells were washed once more. Live cells were then immediately analyzed by confocal laser scanning microscopy using a Leica TCS-SPE operating system. Rhodamine (580 nm) and Cy5 (670 nm) were sequentially excited and emission fluorescence were collected in z-confocal planes of 10-15 nm steps.

7) Flow Cytometry

CHO and F98 cells were incubated with various concentrations of Cy5-labeled peptides in F-12K culture medium without serum at 37° C. for 2 hrs. The cells were then washed with PBS to remove excess extracellular peptide and treated with 1 mg/ml trypsin (INVITROGEN) for 5 min at 37° C. to detach cells from the surface, and centrifuged at 200 g before suspension in PBS. For experiments with the macropinocytosis inhibitor, amiloride, CHO cells were initially washed with F-12K and preincubated for 30 min at 37° C. with 1 mM amiloride (SIGMA). The cells were then incubated for 2 hrs at 37° C. with 1 µM of the Cy5-MCa analogues. For all these experimental conditions, flow cytometry analyses were performed with live cells using a Becton Dickinson flow cytometer LSR II or an Accuri® flow cytometer (BD BIOSCIENCES). Data were obtained and analyzed using FCS express software (DE NOVO) or Accuri® proprietary software CFlow sampler. Live cells were gated by forward/side scattering from a total of 10,000 events.

8) Preparation of Heavy SR Vesicles

Heavy SR vesicles were prepared following the method of Kim et al., J. Biol. Chem., 1983. Protein concentration was measured by the Biuret method. [3H]-Ryanodine binding assay—Heavy SR vesicles (1 mg/ml) were incubated at 37° C. for 2 hrs in an assay buffer composed of 10 nM [$^3$H]-ryanodine, 150 mM KCl, 2 mM EGTA, 2 mM $CaCl_2$ (pCa=5), and 20 mM MOPS, pH 7.4. Truncated MCa analogues were added prior to the addition of heavy SR vesicles. [$^3$H]-ryanodine bound to heavy SR vesicles was measured by filtration through Whatman GF/B glass filters followed by three washes with 5 ml of ice-cold washing buffer composed of 150 mM NaCl, 20 mM HEPES, pH 7.4. [$^3$H]-ryanodine retained on the filters was measured by liquid scintillation. Non-specific binding was measured in the presence of 80 µM unlabeled ryanodine. The data are presented as mean±S.E. Each experiment was performed in triplicate.

9) Statistical Analyses

All data are given as mean±SD for n number of observations, and statistical significance (p) was calculated using Student's t test.

EXAMPLE 2

Non Folded Truncated Maurocalcine Peptides are Efficient CPP

Figure 1:
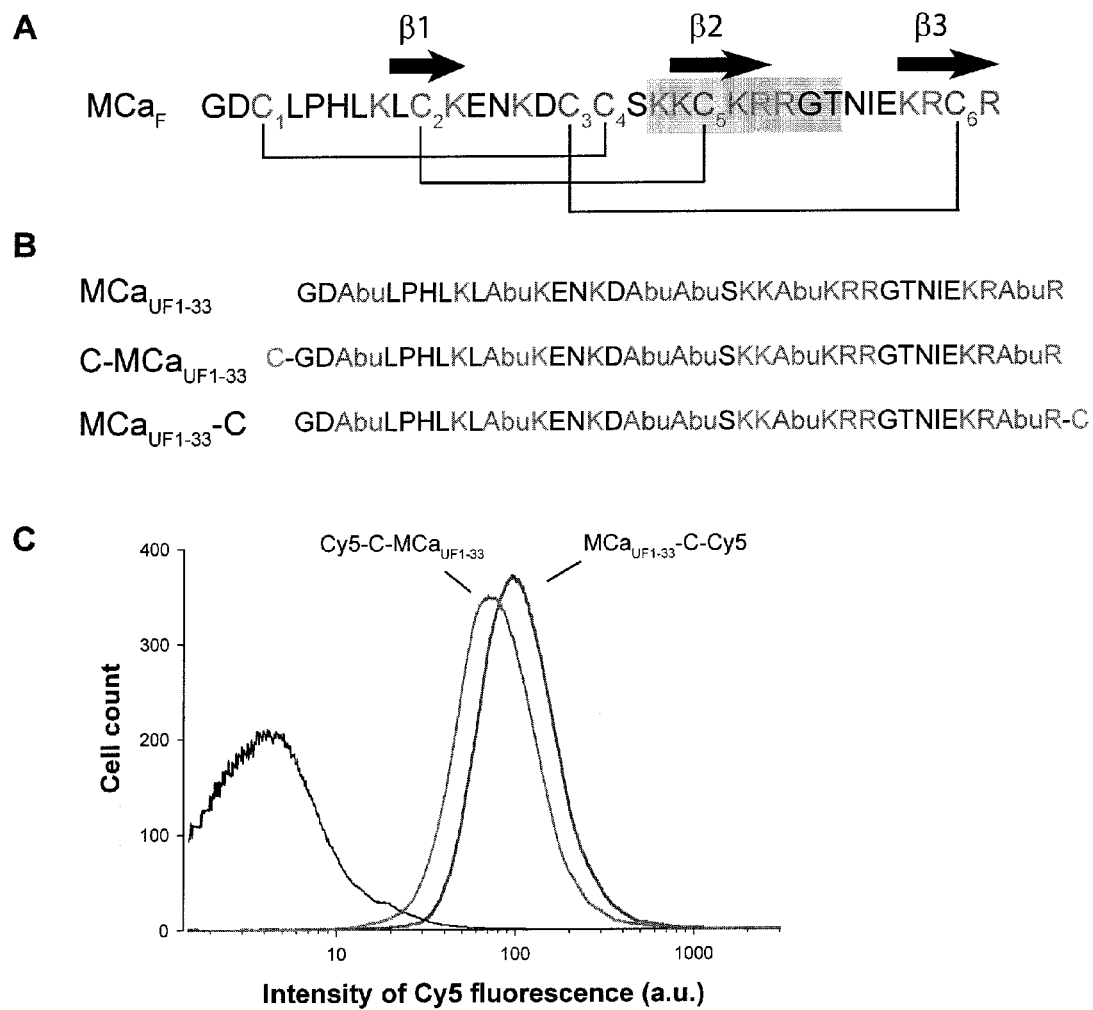

FIG. 1A illustrates the primary structure of MCa with its secondary structures (β strands) and its pattern of disulfide bridges. This peptide will be termed MCaF, for folded (F) MCa. An earlier report has demonstrated that replacing the six internal cysteine residues of MCa by Abu residues results in a pharmacologically-inert and unfolded (UF) CPP ($MCa_{UF1-33}$, FIG. 1B). This peptide loses its secondary structures (Ram et al., J. Biol. Chem., 2008). Since the present application aims at identifying shorter CPP sequences based on $MCa_{UF1-33}$ sequence by the delivery of Cy5 cargo, the inventors first determined where at the N-terminus (C-$MCa_{UF1-33}$) or C-terminus ($MCa_{UF1-33}$-C) the cargo could be best grafted after addition of an extra cysteine residue (C) (FIG. 1B). As shown, both vector/cargo complexes Cy5-C-$MCa_{UF1-33}$ and $MCa_{UF1-33}$-C-Cy5 penetrated efficiently within CHO cells, as estimated by confocal microscopy or by flow cytometry (FIG. 1C). At 3 NM, a slightly better cell penetration was observed with Cy5 localized at the C-terminus of $MCa_{UF1-33}$, but this difference was not significant. Since chemical syntheses of truncated $MCa_{UF1-33}$ analogues was facilitated by adding the extra cysteine residue at the C-terminus of the sequence rather than at the N-terminus, the inventors kept on working on the basis of $MCa_{UF1-33}$-C sequence. Nevertheless, these data indicate for the first time that cargo grafting on the CPP $MCa_{UF1-33}$ can be performed likewise at both extremities of the sequence. Next, the inventors designed a series of truncated MCaUF-C peptides comprising either a C-terminal truncation (3 analogues: $MCa_{UF1-20}$-C, $MCa_{UF1-15}$-C and $MCa_{UF1-9}$-C), a N-terminal truncation (7 analogues: $MCaUF_{8-33}$-C, $MCa_{UF11-33}$-C, $MCa_{UF14-33}$-C, $MCa_{UF18-33}$-C, 33-C, $MCa_{UF20-33}$-C, $MCa_{UF22-33}$-C and $MCa_{UF25-33}$-C), and Both N- and C-terminal truncations (2 analogues: $MCa_{UF6-25}$-C and $MCa_{UF14-25}$-C) (FIG. 2A). All of these analogues were then labeled with Cy5 to investigate their cell penetration properties. Every one of these peptides has been designed in such a way that the cargo would be removed from the peptide upon trypsin cleavage. This was useful for the flow cytometry experiments in which the fluorescence associated to the cells is measured after trypsin treatment, thereby potentially removing the cargo from peptides that would eventually be associated to the outer part of the plasma membrane. The net positive charges of the peptides were drastically different, ranging from 0 ($MCa_{UF1-15}$-C and $MCa_{UF1-9}$-C) to +8 ($MCa_{UF8-33}$-C). However, many of the peptides contained a percentage of positively charged residues equal ($MCa_{UF-25-33}$-C) or superior to MCaF or $MCa_{UF1-33}$ (8 out of twelve analogues). Three analogues had a lower percentage of basic residues than MCaF (all three C-terminal truncated analogues, $MCa_{UF1-20}$-C, $MCa_{UF1-15}$-C and $MCa_{UF1-9}$-C). The inventors first evaluated by flow cytometry the fluorescence accumulation within CHO cells that occurred after 2 hrs incubation with 3 µM of positively charged MCa peptides (net charge ≥+5; FIG. 2B). This first study revealed several unexpected findings. First, all of the charged peptides (8 tested) demonstrated CPP properties. These peptides had all the $K_{22}R_{23}R_{24}$ sequence in common, a cluster of basic amino acid residues shown to contribute to the dose-efficacy of cell penetration of MCaF in an earlier study (Mabrouk et al., 2007). Interestingly, removing the last 8 C-terminal amino acids of MCa had little impact on the cell penetration properties (if one compares $MCa_{UF14-25}$-C with $MCa_{UF14-33}$-C). Similarly, the removal of the amino acid region His6-Asn13 did not drastically change cell penetration properties ($MCa_{UF6-25}$-C versus $MCa_{UF14-25}$-C). Second, all peptides appeared to behave better than the reference peptide $MCa_{UF1-33}$-C, suggesting that sequence truncation of MCaUF may represent a potent strategy to define more efficient CPP. Less positively charged peptides were also tested for their ability to penetrate into CHO cells (FIG. 2C). No less surprisingly, all peptides showed CPP properties, including two peptides with no net positive charge ($MCa_{UF1-9}$-C and $MCa_{UF1-15}$-C). $MCa_{UF1-9}$-C appeared as a better CPP than $MCa_{UF1-15}$-C suggesting that the Abu-Asp region introduces no competitive advantage and confirming results shown in FIG. 2B. This may represent an inhibitory region because of the presence of $Glu_{12}$ and and $Asp_{15}$, two negatively charged residues. The finding that mutation of $Glu_{12}$ to Ala enhances cell penetration of both MCaF (Mabrouk et al., 2007) and MCaUF (Ram et al., J. Biol. Chem., 2008) further supports this conclusion. MCaUF25-33-C turned out to have also CPP properties, even though this sequence did not confer a competitive advantage to other MCa CPP analogues as shown in FIG. 2B. The overall message from this first study is that all truncated MCaUF analogues can behave as CPP at the concentration tested. The findings suggest that MCa is a peptide fully specialized to achieve cell penetration including in domains that are not highly charged.

EXAMPLE 3

Figure 3:
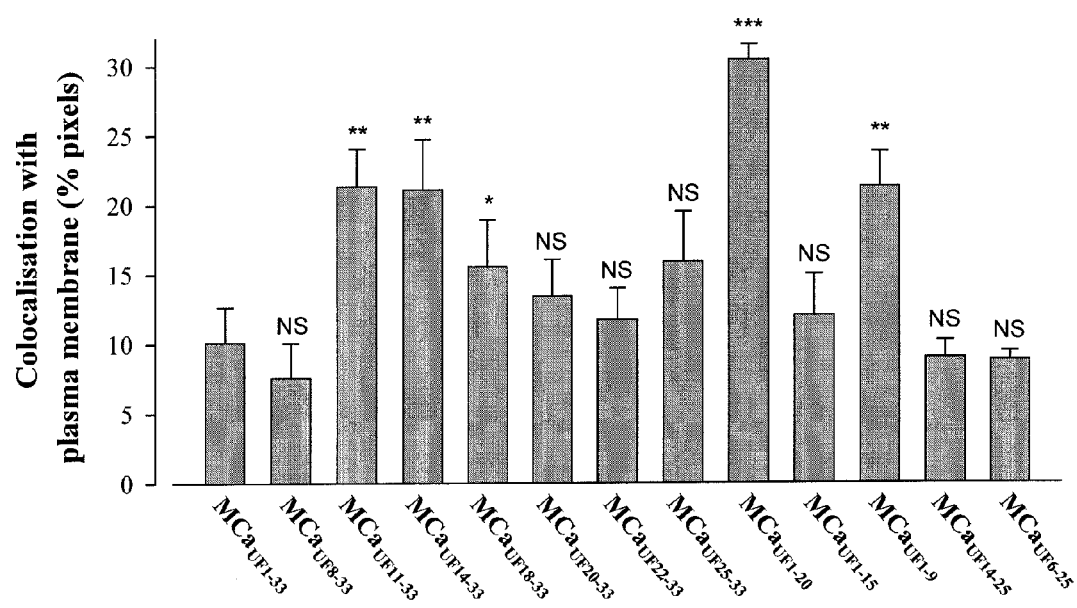

The Intracellular Distribution of all Truncated MCaUF Analogues Bear Resemblance with that of the Full Length MCaUF While all truncated derivatives of MCaUF1-33 show cell penetration properties according to the flow cytometry analyses, the inventors examined whether there were differences in intracellular distribution among these peptides. This question was investigated by confocal microscopy after 2 hrs of peptide accumulation into CHO cells. Interestingly, all peptides showed very resembling intracellular distributions, although the degree of accumulated cell fluorescence varied somewhat with peptide sequences. In confirmation of the flow cytometry results, the peptide that appeared to penetrate the least was the full length unfolded MCa, $MCa_{UF1-33}$-C-Cy5. The vast majority of the fluorescence appears in punctuate dots within the cells. In many cases, these dots appear at higher concentrations within one pole of the cell ($MCa_{UF8-33}$-C-Cy5, $MCa_{UF11-33}$-C-Cy5, $MCa_{UF25-33}$-C-Cy5, and $MCa_{UF1-9}$-C-Cy5 for instance). On various occasions also, all of the peptides tend to present a sub-plasma membrane distribution, forming a rim of smaller circumference than the concanavalin A labeling itself. This sub-plasma membrane rim localization was more evident for CHO cells labeled with $MCa_{UF14-25}$-C-Cy5. Finally, more rarely, a direct plasma membrane labeling by the peptide-cargo complex was observable. This type of labeling could be observed with N-terminal truncated vectors exclusively and was most evident or $MCa_{UF22-33}$-C-Cy5. The staining of the plasma membrane was always diffuse in contrast to intracellular staining which was mainly punctuated. Diffuse membrane labeling was also observed for $MCa_{UF25-33}$-C-Cy5 and $MCaUF_{20-33}$-C-Cy5, two peptides that differ from 2 to 3 amino acids with $MCa_{UF22-33}$-C-Cy5. It was difficult to evidence for the other vector/cargo complexes. The inventors propose that this staining coincides with an alteration of the duration of peptide plasma membrane residency for these truncated $MCa_{UF}$ analogues. The lower occurrence of this diffuse staining for the other truncated variants may reflect faster internalization by endocytosis and/or membrane translocation. Globally, these effects reflect cell entry and distribution tendencies that were hard to quantify and they should therefore be interpreted with caution. In an attempt to better apprehend peptide behavior at the plasma membrane, the inventors quantified the extent of Cy5/rhodamine staining colocalization. Rhodamine-positive staining was also Cy5-positive for 63% to 86% of the pixels (best performing peptides were $MCa_{UF14-33}$-C-Cy5, $MCa_{UF18-33}$-C-Cy5, $MCa_{UF20-33}$-C-Cy5 and $MCa_{UF22-33}$-C-Cy5). This finding indicates that the peptides invade large membrane areas and that membrane interaction is not limited to small specialized surface areas. In contrast, Cy5-positive pixels were rhodamine-positive to far more variable extents (FIG. 3). For instance, 10.1±2.6% of $MCa_{UF1-33}$-C-Cy5, the reference compound, was colocalized with the plasma membrane indicator. In spite of the fact that short plasma membrane staining times were used (few minutes), a fraction of the colocalization that is quantified also corresponds to intracellular staining following ongoing endocytosis. Nevertheless, this result indicates that this peptide does not remain stuck within the plasma membrane during its 2 hrs incubation with CHO cells. It indicates relatively fast cell penetration thus. Many of the other peptides however behaved differently from $MCa_{UF1-33}$-C-Cy5. Indeed, several peptides show surprisingly higher colocalization with rhodamine (21.3±2.6% for $MCa_{UF11-33}$-C-Cy5 and 30.4±1.4% for $MCa_{UF1-20}$-C-Cy5 for instance). These higher values of colocalization indicate that some peptides remain for longer periods of time or at higher concentration within the plasma membrane. Alternatively, these peptides may rely more heavily on endocytosis for cell penetration and are present within intracellular organelles to which subsequent endocytotic vesicles that contain rhodamine labeling will fuse. Peptides most concerned by these behaviors were $MCa_{UF11-33}$-C-Cy5 and $MCa_{UF14-33}$-C-Cy5, that contained two or one of the CPP inhibitory negative charges (Glu12 and Asp15), and $MCa_{UF1-9}$-C-Cy5 and $MCa_{UF1-20}$-C-Cy5, that were poorly charged peptides.

EXAMPLE 4

Amiloride-Sensitivity of the Cell Penetration of Truncated $MCa_{UF}$ Analogues

Figure 4:
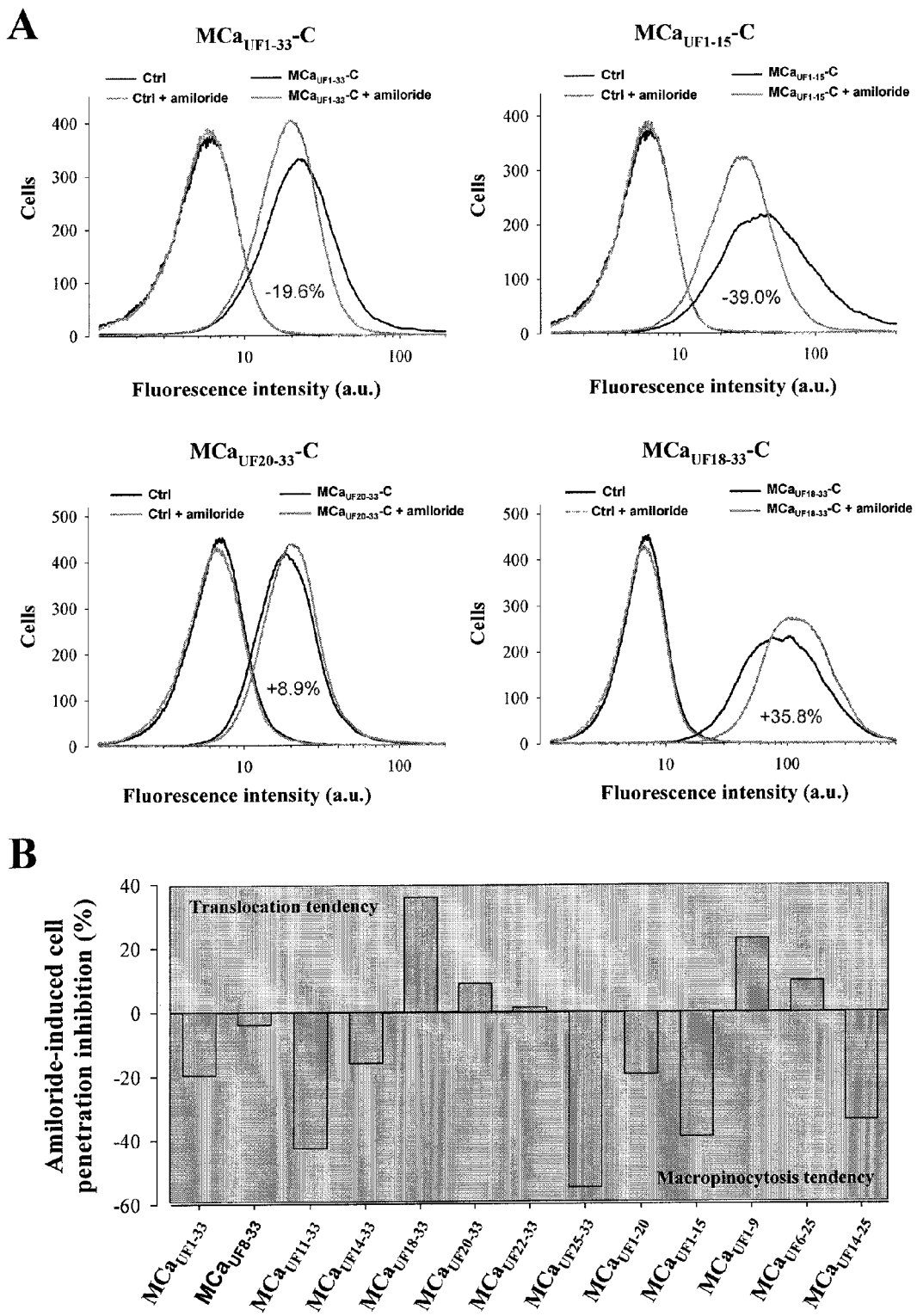

In earlier studies, the inventors have demonstrated that the cell entry of $MCa_{UF1-33}$ was largely sensitive to amiloride, suggesting a predominant macropinocytosis mechanism for its cell penetration (Ram et al., J. Biol. Chem., 2008, 283, 24274-24284). However, it was likely that such a predominant reliance on macropinocytosis was also conferred by the cargo type transported (streptavidine in that report). The inventors therefore conducted an in depth analysis of the amiloride-sensitivity of the various truncated MCaUF peptides with Cy5 as cargo and quantified by flow cytometry the degree of cell penetration inhibition in CHO cells. FIG. 4A illustrates the amiloride-sensitivity of four different truncated peptides. As shown, amiloride inhibits the cell penetration of $MCa_{UF1-33}$-C-Cy5 by 19.6% and of $MCa_{UF1-15}$-C-Cy5 by 39%. The finding that amiloride blocks to a far lesser extend the penetration of Cy5 compared to that of streptavidin (Ram et al., J. Biol. Chem., 2008, 283, 24274-24284) when $MCa_{UF1-33}$ is the vector indicates the influence of the cargo nature on the mechanism of cell entry. Surprisingly, blocking macropinocytosis was found to enhance rather than inhibit the cell penetration of $MCa_{UF20-33}$-C-Cy5 and $MCa_{UF18-33}$-C-Cy5 (FIG. 4A). Preserving the plasma membrane from undergoing macropinocytosis may free surface areas for enhanced peptide translocation trough the membrane. The effect of amiloride was always associated with a sharpening of the fluorescence intensity distribution in the x axis (see for instance $MCa_{UF1-15}$-C-Cy5), reflecting reduced cell heterogeneity for the mechanisms underlying peptide penetration. The amiloride-sensitivity of cell penetration was further investigated for all truncated MCaUF peptides and the results presented in FIG. 4B. Four peptides showed higher amiloride-sensitivity than $MCa_{UF1-33}$-C-Cy5 ($MCa_{UF11-33}$-C-Cy5, $MCa_{UF25-33}$-C-Cy5, $MCa_{UF1-15}$-C-Cy5 and $MCa_{UF14-25}$-C-Cy5). All other peptides showed reduced amiloride-sensitivities or a tendency for greater cell penetration under the effect of amiloride. The inventors conclude that the Cy5 cargo does not promote macropinocytosis as the main route of peptide entry, and that truncation of MCaUF may lead to analogues that rely to a lesser extent on macropinocytosis for cell entry.

EXAMPLE 5

Comparative Dose-Dependent Cell Penetration of the $MCa_{UF}$ Analogues

Figure 5:
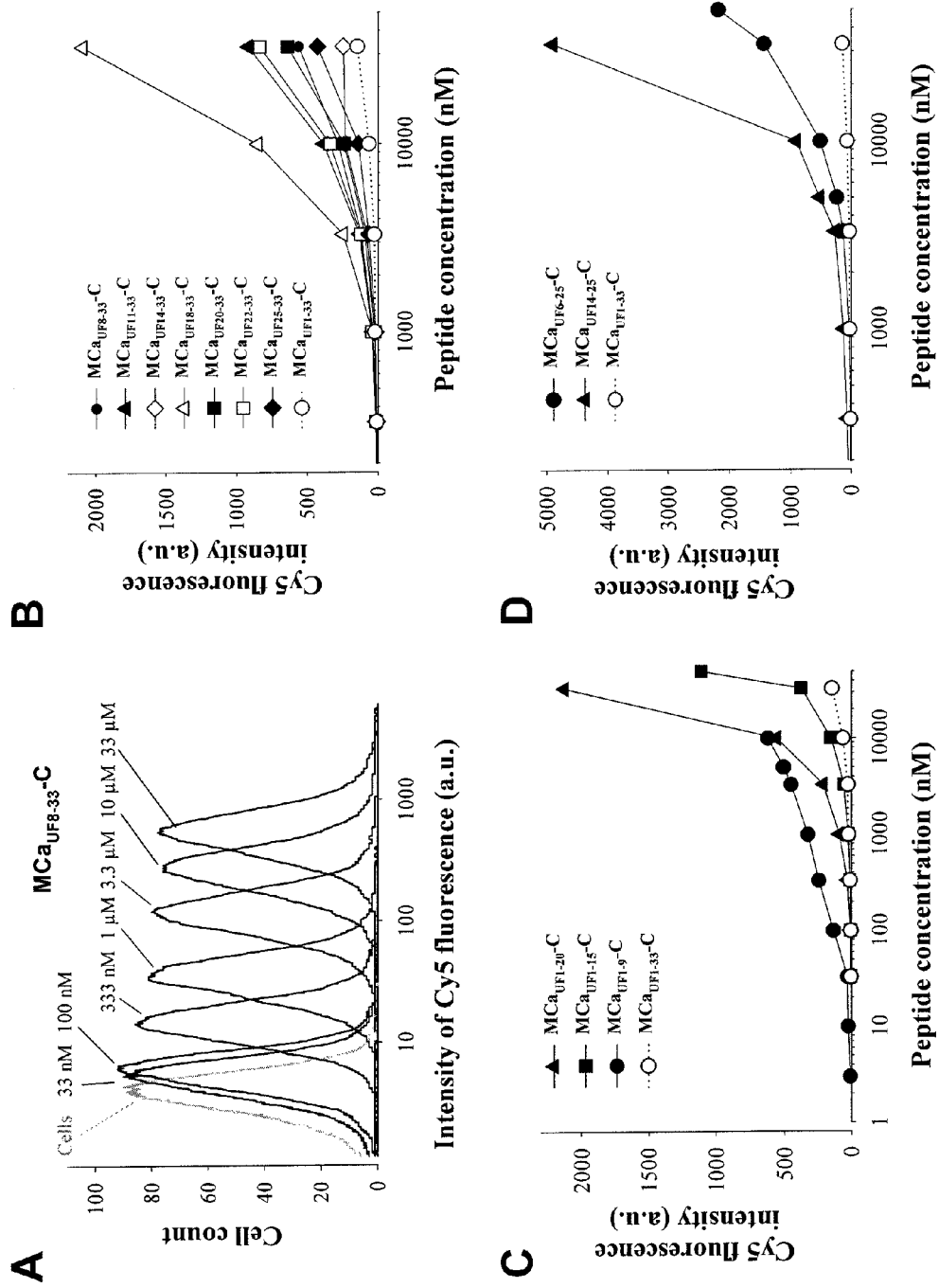

While the inventors compared the properties of cell penetration of truncated peptides at rather mild concentrations, the inventors also aimed at comparing the dose-dependence of cell penetration of these peptides by flow cytometry (FIG. 5). One example of such an analysis is shown for peptide $MCaUF_{8-33}$-C-Cy5 in FIG. 5A. 33 µM was the highest concentration that could be tested on CHO cells and obviously cell penetration did not show any sign of saturation for cell incubation times with this peptide for 2 hrs. The dose-dependent cell penetration were compared for all N-terminal truncated peptides (FIG. 5B), C-terminal truncated peptides (FIG. 5C), and double truncated analogues (FIG. 5D) with the same settings. These analyses confirm that $MCa_{UF1-33}$-C-Cy5 is the least-performing cell penetrating peptide. Most truncated peptides show detectable cell penetration at concentrations equal or above 1 µM. One remarkable exception to this rule was noticeable. $MCa_{UF1-9}$-C-Cy5 shows an unusual dose-dependent penetration with detectable cell penetration at 10 nM and only small progressive increases in fluorescence intensity with higher peptide concentrations (FIG. 5C). This peptide was therefore the best performing peptide for cell penetration at low concentrations. Finally, additional information that could be taken from these analyses is that the peptides differed significantly with regard to the maximal extent of cell penetration. Among the N-terminal truncated $MCa_{UF}$ analogues, $MCa_{UF18-33}$-C-Cy5 performed drastically better than the other truncated peptides (FIG. 5B). The difference in cell penetration among $MCa_{UF11-33}$-C-Cy5 and $MCa_{UF18-33}$-C-Cy5 resides in the removal of KENKD-AbuAbu sequence which the inventors presume is inhibitory to some extent because of the presence of Glu12 and Asp15.

Among the C-terminal truncated peptides, $MCa_{UF1-20}$-C-Cy5 was performing as well as $MCa_{UF8-33}$-C-Cy5, and although not tested at higher concentrations, $MCa_{UF1-9}$-C-Cy5 would be expected to perform still better. Finally, for N- and C-terminal truncated analogues, the best peptide turns out to be $MCa_{UF14-25}$-C-Cy5 that yields the greatest fluorescence accumulation at 33, µM compared to all other truncated MCaUF analogues.

EXAMPLE 6

Figure 6:
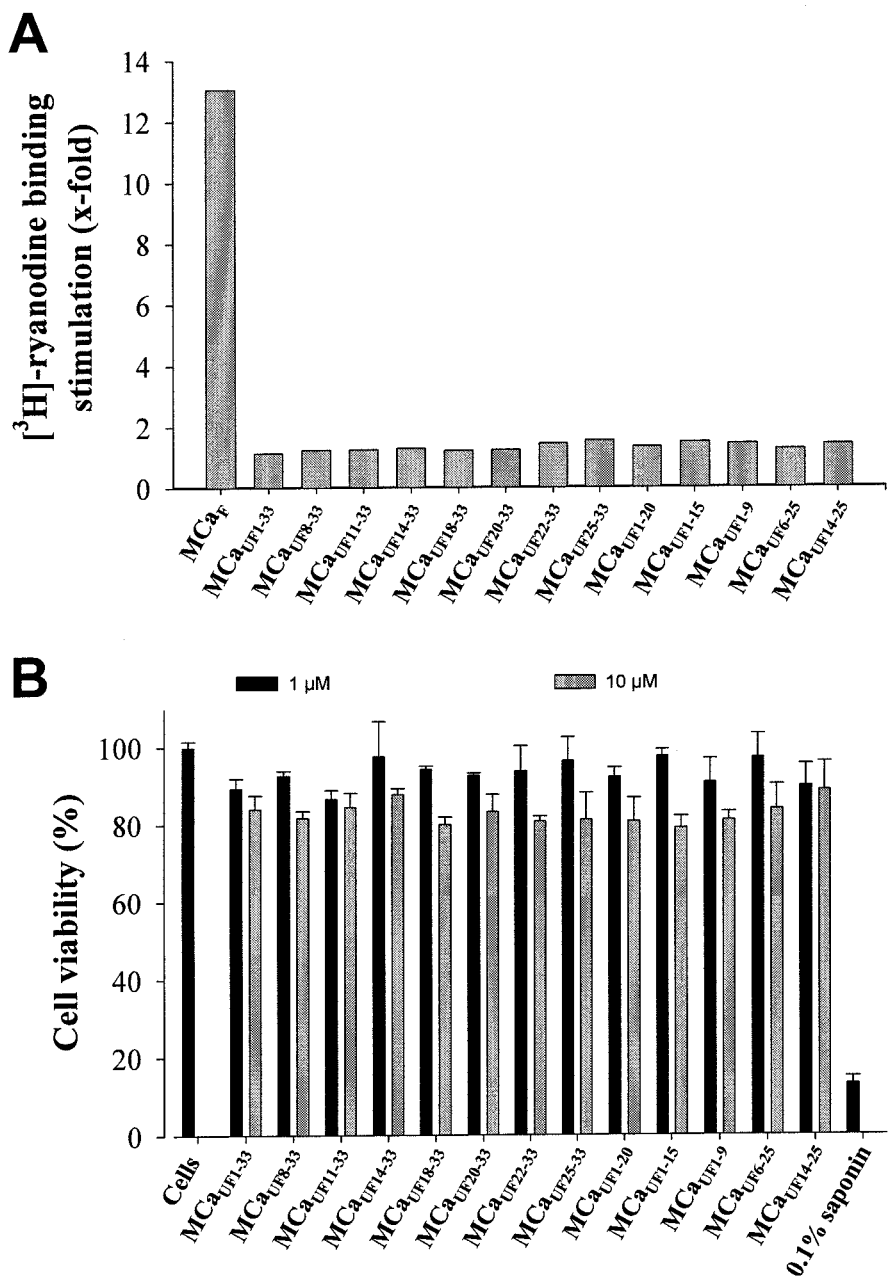
Figure 7:
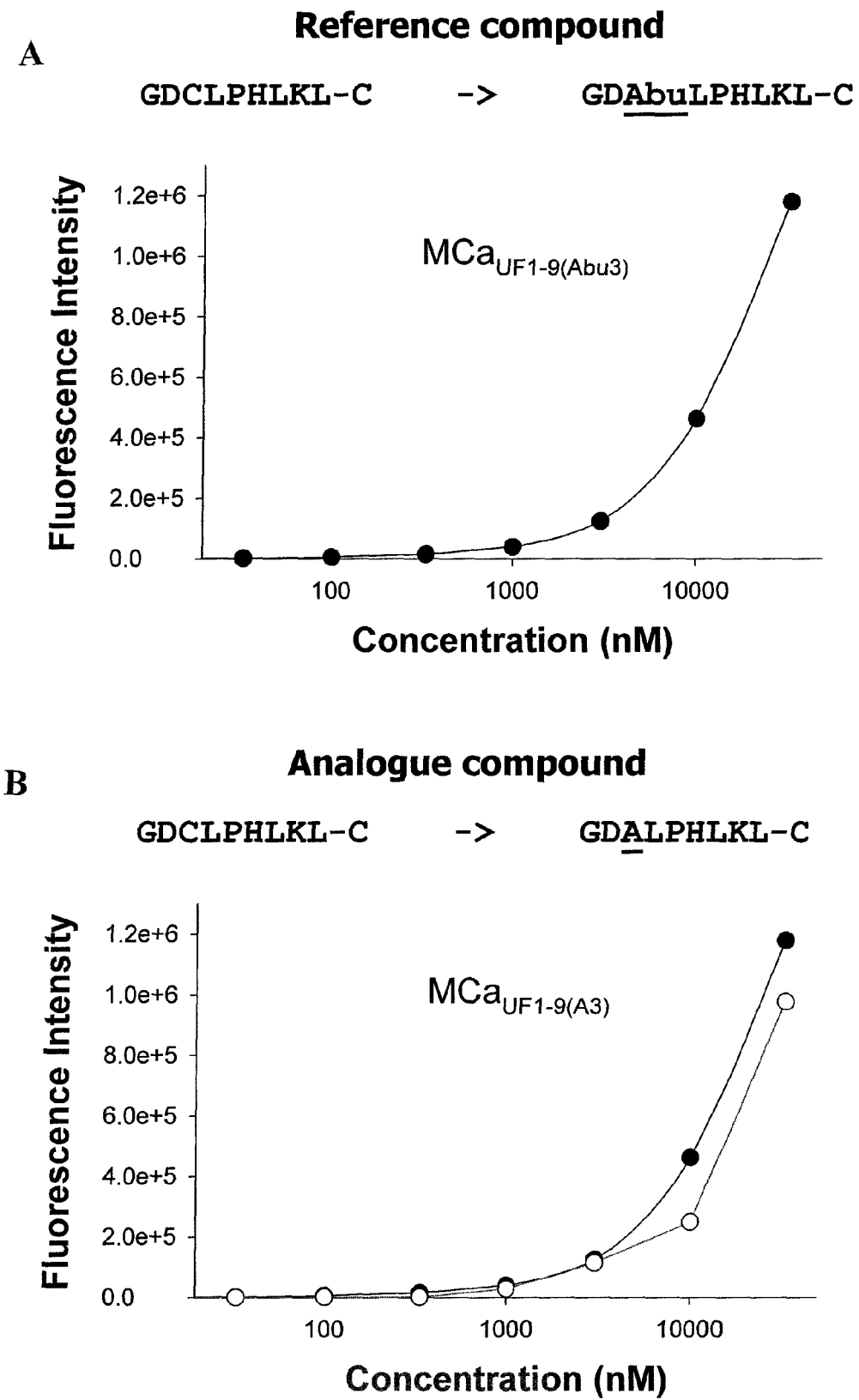
Figure 8:
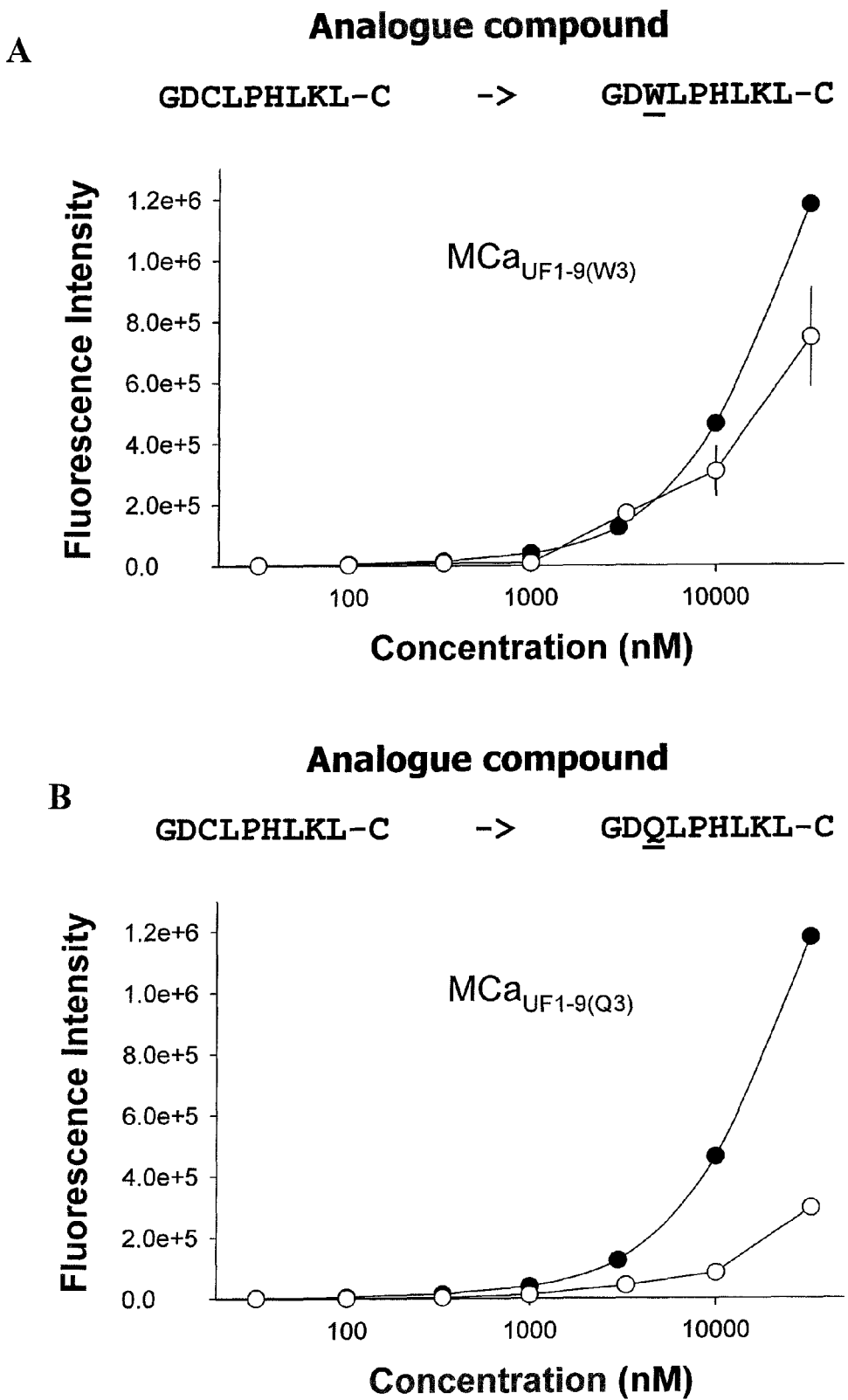
FIG. 8 shows the dose-dependent cell penetration of the $MCa_{UF1-9(W3)}$-C-Cy5 (A) and $MCa_{UF1-9(Q3)}$-C-Cy5 (B) peptides (both in open circle) in F98 cells compared to the reference peptide $MCa_{UF1-9(Abu3)}$-C-Cy5 (closed circle) as analyzed by flow cytometry.
Figure 9:
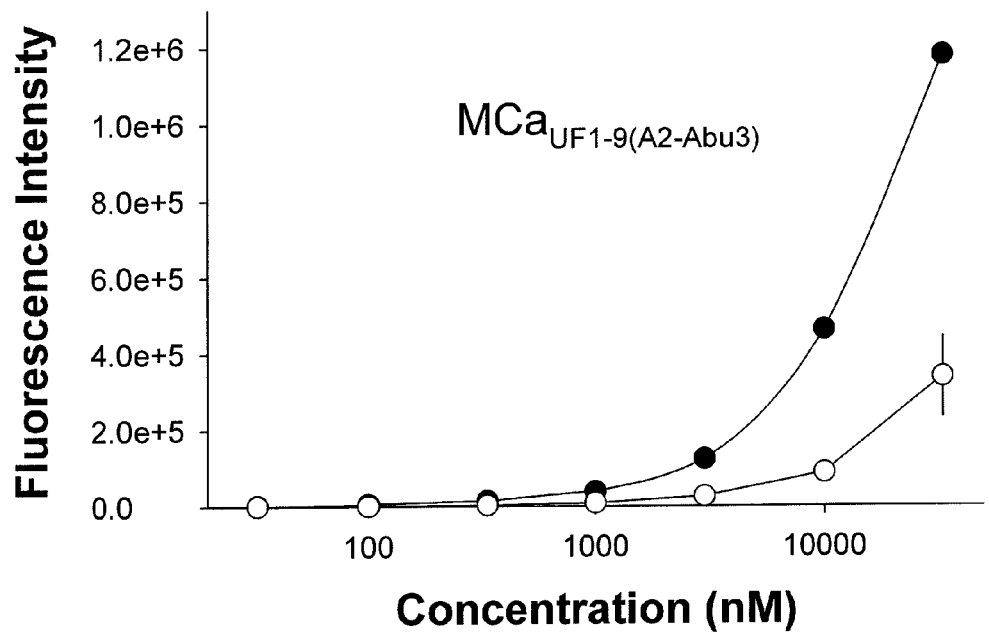
FIG. 9 shows the dose-dependent cell penetration of the $MCa_{UF1-9(A2-Abu3)}$-C-Cy5 peptide (open circle) in F98 cells compared to the reference peptide $MCa_{UF1-9(Abu3)}$-C-Cy5 (closed circle) as analyzed by flow cytometry.
Figure 10:
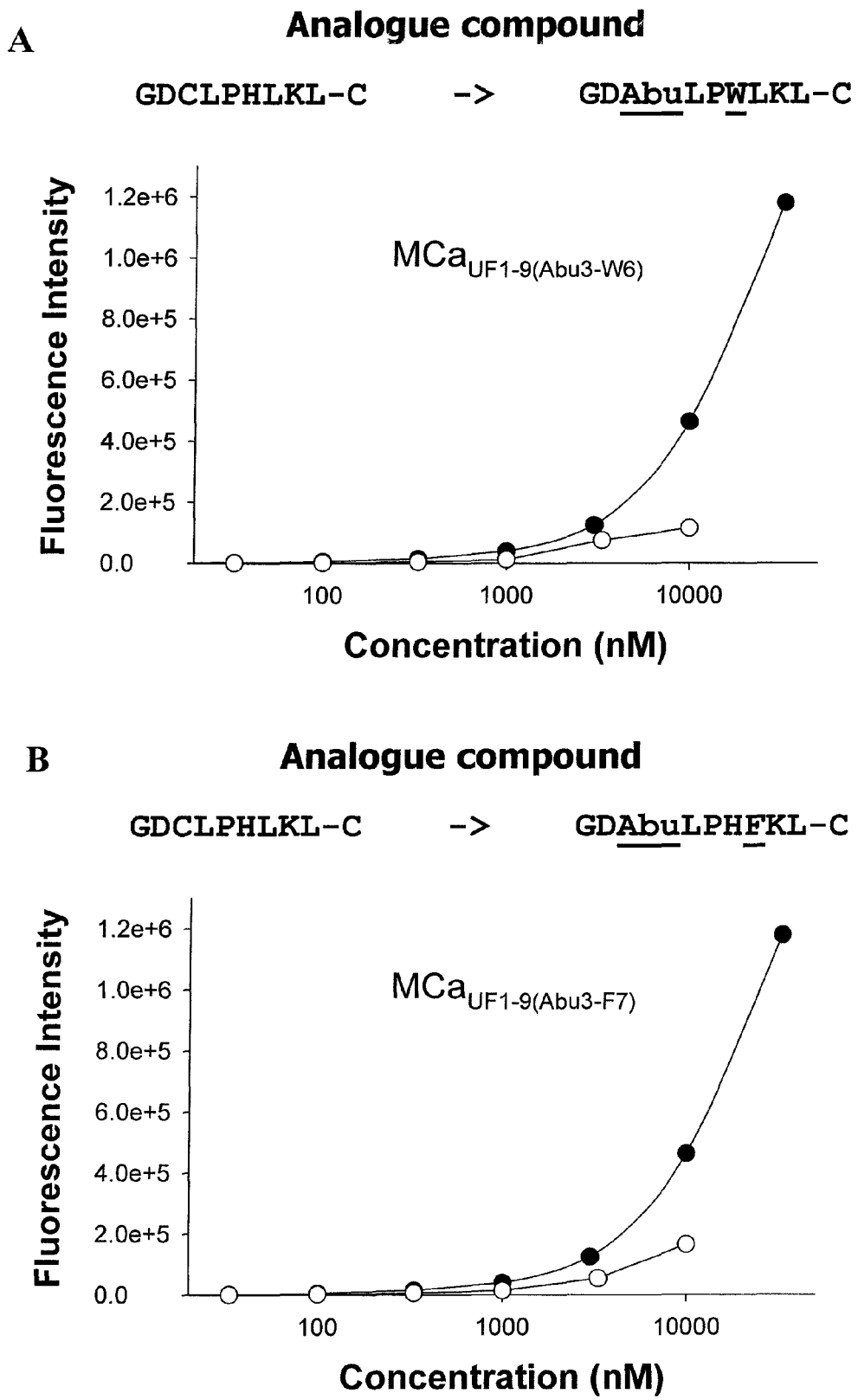
FIG. 10 shows the dose-dependent cell penetration of the $MCa_{UF1-9(Abu3-W6)}$-C-Cy5 (A) and $MCa_{UF1-9(Abu3-F7)}$-C-Cy5 (B) peptides (open circle) in F98 cells compared to the reference peptide $MCa_{UF1-9(Abu3)}$-C-Cy5 (closed circle) as analyzed by flow cytometry.
Figure 11:
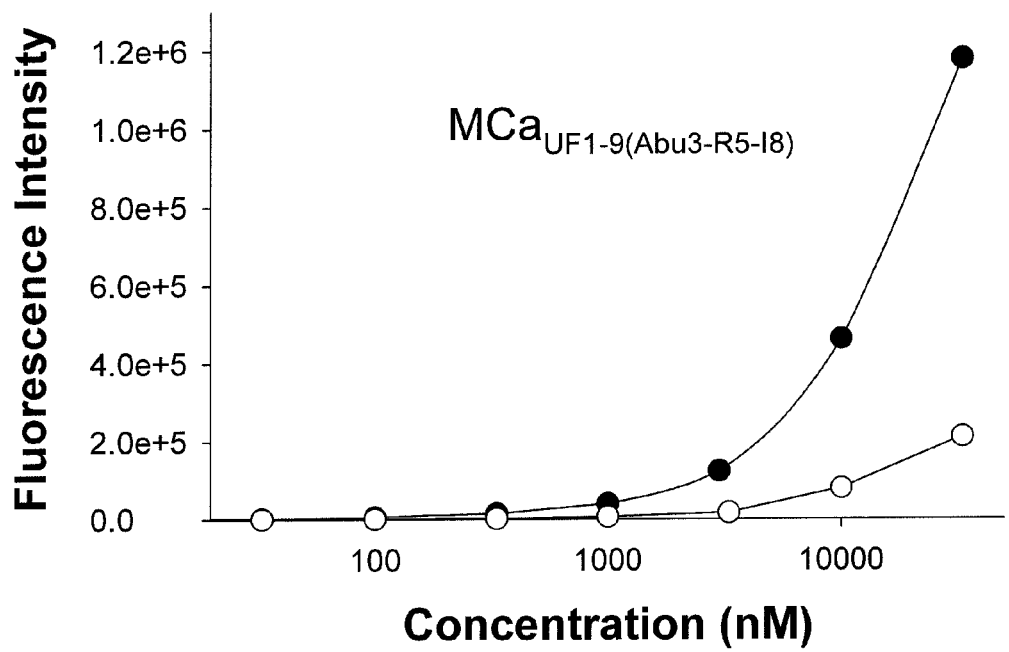
FIG. 11 shows the dose-dependent cell penetration of the $MCa_{UF1-9\ (Abu3-R5-18)}$-C-Cy5 peptide (open circle) in F98 cells compared to the reference peptide $MCa_{UF1-9(Abu3)}$-C-Cy5 (closed circle) as analyzed by flow cytometry.
Figure 14:
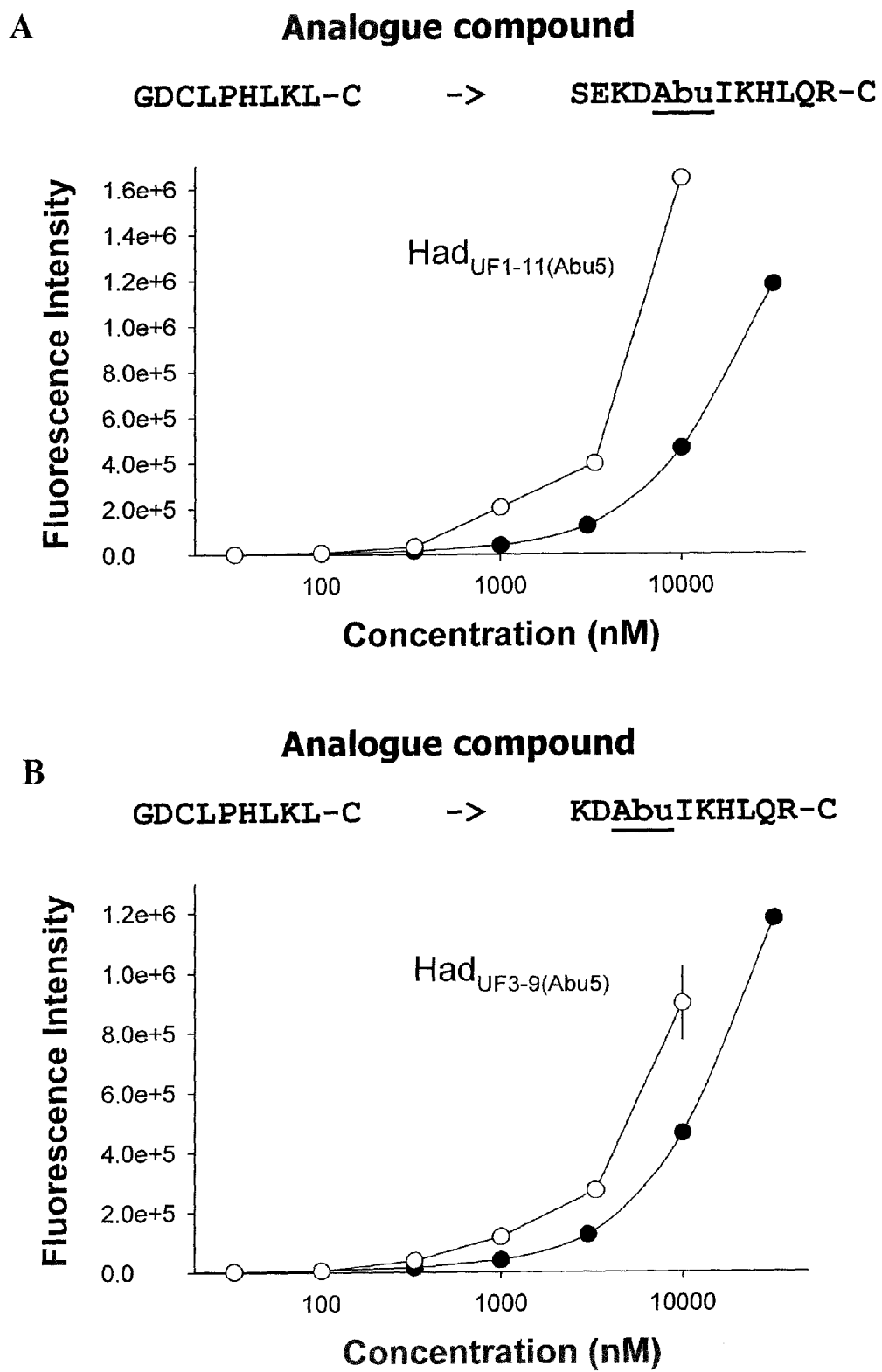
FIG. 14 shows the dose-dependent cell penetration of the $Had_{UF1-11(Abu5)}$-C-Cy5 (A) and $Had_{UF3-9(Abu5)}$-C-Cy5 (B) peptides (open circle) in F98 cells compared to the reference peptide $MCa_{UF1-9(Abu3)}$-C-Cy5 (closed circle) as analyzed by Flow cytometry.

Truncated MCaUF Peptides Lack Pharmacological Effects and are Predominantly Non Toxic An earlier report has shown that $MCa_{UF1-33}$ is unable to interact with MCa's target, the ryanodine receptor RyR1 (Ram et al., J. Biol. Chem., 2008). This is due to the loss of secondary structures owing to the lack of internal disulfide bridging. The inventors did therefore expect that truncated analogues of $MCa_{UF}$ should also be pharmacologically inert. This hypothesis was challenged by testing the ability of the Cy5-free peptides to stimulate [$^3$H]-ryanodine binding (FIG. 6A). As shown, contrary to MCaF that contains secondary structures and disulfide bridges, none of the peptides the inventors designed had an effect on [$^3$H]-ryanodine binding. Finally, the peptides were challenged for their toxicity by incubating CHO cells with 1 or 10 µM peptide concentrations for an extended duration (24 hrs) that far exceeds the duration challenged for cell penetration (FIG. 6B). A 10 µM peptide concentration was generally slightly more toxic than 1 µM except for $MCa_{UF14-25}$-C. At 1 µM, toxicity never exceeded 8% and significances of these effects were negligible. In contrast, toxicity could reach 20% at 10 µM peptide concentration and these effects had higher significance. Most peptides behaved equally well or better than $MCa_{UF1-33}$-C indicating that truncation did not enhance cell toxicity of the peptides.

EXAMPLE 7

Synthesis of a Peptide Containing a Disulfide Bond and a N-Terminal Thiol Function for Coupling to the Cargo The peptide is synthesized by the solid phase method as described in example 1. The peptide bound to the resin is labeled with N-Succinimidyl-S-acetylthioacetate (SATA) to introduce a protected thiol group at the N-terminus of the peptide.

Labeling of Peptide with SATA

SATA (76 mg in 60 µl DMF) and then phosphate buffer saline (PBS), pH 7.4 (540 µl) were added to the peptide bound to the resin (10 mg in 600 µl of PBS, pH 7.4) and the mixture was agitated for 1 hour at room temperature, filtered and washed three times with methanol. The peptide was then deprotected and cleaved from the resin as follows. The preceding mixture was treated 4 hrs at room temperature with a mixture of TFA (Trifluoroacétique acid; 9.25 ml), triisopropylsilane (250 µl), water (250 µl), and Dithiothreitol (250 mg), filtered, and the filtrate was precipitated by adding cold diethyl ether (40 ml) The crude peptide was pelleted by centrifugation (10,000 g, 15 min). The pellet was washed three times by resuspension in diethyl ether (10 ml) and centrifugation (10,000 g, 15 min). The supernatant was discarded and the peptide was air-dried.

Disulphide Bond Formation 4,4'-Dipyridyl disulfide (114 µL of a 10 mM solution in methanol) was added to the labeled peptide (2 mg in 2 ml of acetonitrile (50%), water (50%) and TFA (0.1% TFA) and the mixture was agitated at room temperature for 2 hrs. The solvent was evaporated using a rotavapor. The oxydised peptide (containing an intramolecular disulfide bond) was solubilized in TFA (2 ml of a 0.1% solution in water), purified by HPLC using a JUPITER™ 4 µm PROTEO 90A column (250 mm×10 mm; PHENOMENEX) and a 10-60% acetonitrile gradient (40 minutes, 4 ml/min rate), and lyophilized.

Deprotection of the Thiol Group

The peptide (2 mg in 1 ml of PBS, pH 7.4) was treated with the deacetylation solution (100 µl of 0.5 M hydroxylamine, 25 mM EDTA in PBS, pH 7.4) for 2 hrs at room temperature, purified by HLPC as described above, and lyophilized.

EXAMPLE 8

Cell Penetration of Small Peptides Derived from $MCa_{UF1-9}$

Cy5-labeled peptides derived from $MCa_{UF1-9}$ were synthesized and assayed by confocal microscopy or flow cytometry as described in example 1. The results are presented in FIGS. 7-15.

The analysis of the $MCa_{UF1-9}$ truncated variant ($MCa_{UF3-9(Abu3)}$) shows that a peptide of 7 residues derived from $MCa_{UF1-9}$ is an efficient CPP (FIG. 12A).

The analysis of the $MCa_{UF1-9}$ variants with point mutations, including Imperatoxin and Hadrucalcine derived peptides, show that the first residues of the $MCa_{UF1-9}$ derived CPP may have various sequences including for example GA ($MCa_{UF1-9(A2-Abu3)}$; FIG. 9A), SEKD or KD ($Had_{UF1-11(Abu5)}$ and $Had_{UF3-9(Abu5)}$; FIGS. 14A and 14B), and GD ($MCa_{UF1-9(Abu3)}$, FIG. 7A; all other variants tested).

The residue in position 3 of the $MCa_{UF1-9}$ derived CPP may be, either a hydrophobic amino acid such as a cysteine analog (Abu; $MCa_{UF1-9(Abu3)}$; FIG. 7A), an alanine ($MCa_{UF1-9(A3)}$; FIG. 7B) or a tryptophan ($MCa_{UF1-9(W3)}$; FIG. 8A), or an other amino acid different from K and R, for example a glutamine ($MCa_{UF1-9(Q3)}$; FIG. 8B). It is preferably a hydrophobic amino acid.

The residue in position 4 of the $MCa_{UF1-9}$ derived CPP is a hydrophobic amino acid, preferably a leucine ($MCa_{U1-9(Abu3)}$; FIG. 7A) or an isoleucine ($Had_{UF1-11(Abu5)}$ and $Had_{UF3-9(Abu5)}$; FIGS. 14A and 14B).

The residue in position 5 of the $MCa_{UF1-9}$ derived CPP is a basic amino acid chosen from K ($Had_{UF1-11(Abu5)}$ and $Had_{UF3-9(Abu5)}$; FIGS. 14A and 14B) and R ($MCa_{UF1-9(Abu3-R5-18)}$; FIG. 11A), or another amino acid different from S, T, D and E such as P ($MCa_{UF1-9(Abu3)}$; FIG. 7A). Preferably, it is P, K or R.

The residue in position 6 of the $MCa_{UF1-9}$ derived CPP is either an amino acid different from S, T, D and E, such as H ($MCa_{UF1-9(Abu3)}$, $Had_{UF1-11(Abu5)}$ and $Had_{UF3-9(Abu5)}$; FIGS. 7A, 14A and 14B), or a hydrophobic amino acid, for example a tryptophan ($MCa_{UF1-9(Abu3-W6)}$; FIG. 10A). Preferably, it is H.

The residue in position 7 of the $MCa_{UF1-9}$ derived CPP is a hydrophobic amino acid, for example a leucine ($MCa_{UF1-9(Abu3)}$, $Had_{UF1-11(Abu5)}$, $Had_{UF3-9(Abu5)}$; FIGS. 7A, 14A and 14B) or a phenylalanine ($MCa_{UF1-9(Abu3-F7)}$; FIG. 10B). Preferably, it is L.

The residue in position 8 of the $MCa_{UF1-9}$ derived CPP is a basic amino acid, for example a lysine ($MCa_{UF1-9(Abu3)}$, FIG. 7A), a hydrophobic amino acid, for example an isoleucine ($MCa_{UF1-9(Abu3-R5-18)}$; FIG. 11A), or another amino acid different from S, T, D and E, for example a glutamine ($Had_{UF1-11(Abu5)}$, $Had_{UF3-9(Abu5)}$, FIGS. 14A and 14B). Preferably, it is K, Q, R or N.

The residue in position 9 of the $MCa_{UF1-9}$ derived CPP is a hydrophobic amino acid, for example a leucine ($MCa_{UF1-9(Abu3)}$, FIG. 7A) or a methionine ($MCa_{UF1-9(Abu3-M9)}$, FIG. 13A), a basic amino acid, for example an arginine ($IMp_{UF1-9(Abu3)}$, $Had_{UF1-11(Abu5)}$, $Had_{UF3-9(Abu5)}$; FIGS. 12B, 14A and 14B), or an other amino acid, for example an asparagine ($MCa_{UF1-9(Abu3-N9)}$, FIG. 13B). Preferably, it is L, R, I or K.

Interestingly, the hadrucalcine derived peptides $Had_{UF1-11(Abu5)}$ and $Had_{UF3-9(Abu5)}$ perform better as CPP than the maurocalcine derived peptide $MCa_{UF1-9(Abu3)}$ (FIGS. 14A and 14B).

Comparison of MCa and Had derived peptides to a classical CPP (Tat basic peptide: GRKKRRQRRR-C; SEQ ID NO: 172) shows that 3 µM $MCa_{UF1-9(Abu3)}$ or 1 µM $MCa_{UF3-9(Abu3)}$, $MCa_{UF1-9(W3)}$, $MCa_{UF1-9(Abu3-W4)}$ or $Had_{UF1-11(Abu5)}$ proved better CPP than Tat at 3 µM (FIG. 15).

REFERENCES

1. Fajloun, Z., Kharrat, R., Chen, L., Lecomte, C., Di Luccio, E., Bichet, D., El Ayeb, M., Rochat, H., Allen, P. D., Pessah, I. N., De Waard, M., and Sabatier, J. M. (2000) FEBS Lett 469, 179-185.
2. Mosbah, A., Kharrat, R., Fajloun, Z., Renisio, J. G., Blanc, E., Sabatier, J. M., El Ayeb, M., and Darbon, H. (2000) Proteins 40, 436-442.
3. Chen, L., Esteve, E., Sabatier, J. M., Ronjat, M., De Waard, M., Allen, P. D., and Pessah, I. N. (2003) J Biol Chem 278, 16095-16106.
4. Lukacs, B., Sztretye, M., Almassy, J., Sarkozi, S., Dienes, B., Mabrouk, K., Simut, C., Szabo, L., Szentesi, P., De Waard, M., Ronjat, M., Jona, I., and Csemoch, L. (2008) Biophys J 95, 3497-3509.
5. Esteve, E., Smida-Rezgui, S., Sarkozi, S., Szegedi, C., Regaya, I., Chen, L., Altafaj, X., Rochat, H., Allen, P., Pessah, I. N., Marty, I., Sabatier, J. M., Jona, I., De Waard, M., and Ronjat, M. (2003) J Biol Chem 278, 37822-37831.
6. Altafaj, X., Cheng, W., Esteve, E., Urbani, J., Grunwald, D., Sabatier, J. M., Coronado, R., De Waard, M., and Ronjat, M. (2005) J Biol Chem 280, 4013-4016.
7. Szappanos, H., Smida-Rezgui, S., Cseri, J., Simut, C., Sabatier, J. M., De Waard, M., Kovacs, L., Csemoch, L., and Ronjat, M. (2005) J Physiol 565, 843-853.
8. Pouvreau, S., Csemoch, L., Allard, B., Sabatier, J. M., De Waard, M., Ronjat, M., and Jacquemond, V. (2006) Biophys J 91, 2206-2215.
9. Esteve, E., Mabrouk, K., Dupuis, A., Smida-Rezgui, S., Altafaj, X., Grunwald, D., Platel, J. C., Andreotti, N., Marty, I., Sabatier, J. M., Ronjat, M., and De Waard, M. (2005) J Biol Chem 280, 12833-12839.
10. Ram, N., Weiss, N., Texier-Nogues, I., Aroui, S., Andreotti, N., Pirollet, F., Ronjat, M., Sabatier, J. M., Darbon, H., Jacquemond, V., and De Waard, M. (2008) J Biol Chem.
11. Aroui, S., Brahim, S., De Waard, M., Breard, J., and Kenani, A. (2009) Cancer Lett 285, 28-38.
12. Aroui, S., Brahim, S., Hamelin, J., De Waard, M., Breard, J., and Kenani, A. (2009) Apoptosis 14, 1352-1365.

13. Aroui, S., Ram, N., Appaix, F., Ronjat, M., Kenani, A., Pirollet, F., and De Waard, M. (2009) Pharm Res 26, 836-845.
14. Boisseau, S., Mabrouk, K., Ram, N., Garmy, N., Collin, V., Tadmouri, A., Mikati, M., Sabatier, J. M., Ronjat, M., Fantini, J., and De Waard, M. (2006) Biochim Biophys Acta 1758, 308-319.
15. Ram, N., Aroui, S., Jaumain, E., Bichraoui, H., Mabrouk, K., Ronjat, M., Lortat-Jacob, H., and De Waard, M. (2008) J Biol Chem 283, 24274-24284.
16. Mabrouk, K., Ram, N., Boisseau, S., Strappazzon, F., Rehaim, A., Sadoul, R., Darbon, H., Ronjat, M., and De Waard, M. (2007) Biochim Biophys Acta 1768, 2528-2540.
17. Poillot, C., Dridi, K., Bichraoui, H., Pecher, J., Alphonse, S., Douzi, B., Ronjat, M., Darbon, H., and De Waard, M. (2010) J Biol Chem 285, 34168-34180.
18. Merrifield, R. B. (1969) Adv Enzymol Relat Areas Mol Biol 32, 221-296.
19. Kim, D. H., Ohnishi, S. T., and Ikemoto, N. (1983) J Biol Chem 258, 9662-9668.

---

The invention claimed is:

1. A method of using a peptide as a vector for the intracellular delivery of a molecular cargo comprising the step of delivering a complex of said peptide and molecular cargo across a plasma membrane of a cell, wherein said peptide is a maurocalcine derived cell penetrating peptide comprising the sequence:

$$Z-X_1-X_2-X_3-X_4-X_5-X_6-X_7-Z',$$

wherein:
the sequence $X_1-X_2-X_3-X_4-X_5-X_6-X_7$ is selected from the group consisting of SEQ ID NO: 3 to 20,
Z is absent or is selected from GD, GA, KD and SEKD (SEQ ID NO: 173), and
Z' is absent or is selected from the group consisting of:
  a) SEQ ID NO: 22, 25, 28, 31 and 34;
  b) SEQ ID NO: 22, 25, 28, 31 and 34, wherein the glutamic acid residue in position 3 or the aspartic acid residue in position 6 is substituted with N, Q, P or G, and/or the serine or glycine residue in position 9 is substituted with Q or N;
  c) N-terminal fragments of SEQ ID NO: 22, 25, 28, 31 and 34, wherein the N-terminal fragments consist of the first 1 to 10 amino acids of said sequences, and
  d) one or more of the sequences of a), b), and c) wherein the residues in positions 2 to 9, the residues in positions 3 to 6, or one or more of the residues in position 3, 6 and 9 of said sequences have been deleted.

2. The method of using according to claim 1, wherein the sequence $X_1-X_2-X_3-X_4-X_5-X_6-X_7$ is chosen from the group consisting of SEQ ID NO: 3, 9, 12 and 18.

3. The method of using according to claim 1, wherein said peptide is selected from the group consisting of: SEQ ID NO: 3 to 20, 44 to 85, 148, 150, and 152.

4. The method according to claim 3, wherein said peptide is selected from the group consisting of: SEQ ID NO: 3, 9, 12, 18, 44, 46, 66, 150, and 152.

5. The method of using according to claim 1, wherein said peptide consists of L-amino acids, D-amino acids or a mixture thereof.

6. The method of using according to claim 1, wherein said peptide comprises a cysteine at its N- or C-terminus.

7. The method of claim 1, further comprising the step of contacting said peptide and molecular cargo with the cell.

8. The method of claim 7 wherein said contacting step is performed in vitro.

9. The method of claim 7 wherein said contacting step is performed in vivo.

10. The method of claim 1, wherein said complex further comprises a targeting moiety.

11. A method of treating a subject in need comprising the step of administering a therapeutically effective amount of a complex comprising an active agent and a peptide comprising a sequence according to claim 1.

* * * * *

SEQUENCE LISTING

<160> NUMBER OF SEQ ID NOS: 173

<210> SEQ ID NO 1
<211> LENGTH: 33
<212> TYPE: PRT
<213> ORGANISM: Scorpio maurus palmatus

<400> SEQUENCE: 1

Gly Asp Cys Leu Pro His Leu Lys Leu Cys Lys Glu Asn Lys Asp Cys
1               5                   10                  15

Cys Ser Lys Lys Cys Lys Arg Arg Gly Thr Asn Ile Glu Lys Arg Cys
            20                  25                  30

Arg

<210> SEQ ID NO 2
<211> LENGTH: 20
<212> TYPE: PRT
<213> ORGANISM: artificial sequence
<220> FEATURE:
<223> OTHER INFORMATION: MCa1-20

<400> SEQUENCE: 2

Gly Asp Cys Leu Pro His Leu Lys Leu Cys Lys Glu Asn Lys Asp Cys
1               5                   10                  15

Cys Ser Lys Lys
            20

<210> SEQ ID NO 3
<211> LENGTH: 7
<212> TYPE: PRT
<213> ORGANISM: artificial sequence
<220> FEATURE:
<223> OTHER INFORMATION: MCa3-9

<400> SEQUENCE: 3

Cys Leu Pro His Leu Lys Leu
1               5

<210> SEQ ID NO 4
<211> LENGTH: 7
<212> TYPE: PRT
<213> ORGANISM: artificial sequence
<220> FEATURE:
<223> OTHER INFORMATION: MCa3-9 H6A variant

<400> SEQUENCE: 4

Cys Leu Pro Ala Leu Lys Leu
1               5

<210> SEQ ID NO 5
<211> LENGTH: 7
<212> TYPE: PRT
<213> ORGANISM: artificial sequence

```
<220> FEATURE:
<223> OTHER INFORMATION: MCa3-9 K8A variant

<400> SEQUENCE: 5

Cys Leu Pro His Leu Ala Leu
1               5

<210> SEQ ID NO 6
<211> LENGTH: 7
<212> TYPE: PRT
<213> ORGANISM: artificial sequence
<220> FEATURE:
<223> OTHER INFORMATION: Opi/IpTx3-9

<400> SEQUENCE: 6

Cys Leu Pro His Leu Lys Arg
1               5

<210> SEQ ID NO 7
<211> LENGTH: 7
<212> TYPE: PRT
<213> ORGANISM: artificial sequence
<220> FEATURE:
<223> OTHER INFORMATION: Opi/IpTx3-9 H6A variant

<400> SEQUENCE: 7

Cys Leu Pro Ala Leu Lys Arg
1               5

<210> SEQ ID NO 8
<211> LENGTH: 7
<212> TYPE: PRT
<213> ORGANISM: artificial sequence
<220> FEATURE:
<223> OTHER INFORMATION: Opi/IpTx3-9 K8A variant

<400> SEQUENCE: 8

Cys Leu Pro His Leu Ala Arg
1               5

<210> SEQ ID NO 9
<211> LENGTH: 7
<212> TYPE: PRT
<213> ORGANISM: artificial sequence
<220> FEATURE:
<223> OTHER INFORMATION: HadruCa5-11

<400> SEQUENCE: 9

Cys Ile Lys His Leu Gln Arg
1               5

<210> SEQ ID NO 10
<211> LENGTH: 7
<212> TYPE: PRT
<213> ORGANISM: artificial sequence
<220> FEATURE:
<223> OTHER INFORMATION: HadruCa5-11 H6A variant

<400> SEQUENCE: 10

Cys Ile Lys Ala Leu Gln Arg
1               5

<210> SEQ ID NO 11
<211> LENGTH: 7
<212> TYPE: PRT
<213> ORGANISM: artificial sequence
<220> FEATURE:
```

<223> OTHER INFORMATION: HadruCa5-11 K8A variant

<400> SEQUENCE: 11

Cys Ile Lys His Leu Ala Arg
1               5

<210> SEQ ID NO 12
<211> LENGTH: 7
<212> TYPE: PRT
<213> ORGANISM: artificial sequence
<220> FEATURE:
<223> OTHER INFORMATION: MCa3-9 C3Abu variant
<220> FEATURE:
<221> NAME/KEY: VARIANT
<222> LOCATION: (1)..(1)
<223> OTHER INFORMATION: 2-amino butyric acid

<400> SEQUENCE: 12

Xaa Leu Pro His Leu Lys Leu
1               5

<210> SEQ ID NO 13
<211> LENGTH: 7
<212> TYPE: PRT
<213> ORGANISM: artificial sequence
<220> FEATURE:
<223> OTHER INFORMATION: MCa3-9 C3Abu/H6A variant
<220> FEATURE:
<221> NAME/KEY: VARIANT
<222> LOCATION: (1)..(1)
<223> OTHER INFORMATION: 2-amino butyric acid

<400> SEQUENCE: 13

Xaa Leu Pro Ala Leu Lys Leu
1               5

<210> SEQ ID NO 14
<211> LENGTH: 7
<212> TYPE: PRT
<213> ORGANISM: artificial sequence
<220> FEATURE:
<223> OTHER INFORMATION: MCa3-9  C3Abu/K8A variant
<220> FEATURE:
<221> NAME/KEY: variant
<222> LOCATION: (1)..(1)
<223> OTHER INFORMATION: 2-amino butyric acid

<400> SEQUENCE: 14

Xaa Leu Pro His Leu Ala Leu
1               5

<210> SEQ ID NO 15
<211> LENGTH: 7
<212> TYPE: PRT
<213> ORGANISM: artificial sequence
<220> FEATURE:
<223> OTHER INFORMATION: Opi/IpTx3-9  C3Abu variant
<220> FEATURE:
<221> NAME/KEY: VARIANT
<222> LOCATION: (1)..(1)
<223> OTHER INFORMATION: 2-amino butyric acid

<400> SEQUENCE: 15

Xaa Leu Pro His Leu Lys Arg
1               5

<210> SEQ ID NO 16
<211> LENGTH: 7
<212> TYPE: PRT

<213> ORGANISM: artificial sequence
<220> FEATURE:
<223> OTHER INFORMATION: Opi/IpTx3-9 C3Abu/H6A variant
<220> FEATURE:
<221> NAME/KEY: variant
<222> LOCATION: (1)..(1)
<223> OTHER INFORMATION: 2-amino butyric acid

<400> SEQUENCE: 16

Xaa Leu Pro Ala Leu Lys Arg
1               5

<210> SEQ ID NO 17
<211> LENGTH: 7
<212> TYPE: PRT
<213> ORGANISM: artificial sequence
<220> FEATURE:
<223> OTHER INFORMATION: Opi/IpTx3-9 C3Abu/K8A variant
<220> FEATURE:
<221> NAME/KEY: variant
<222> LOCATION: (1)..(1)
<223> OTHER INFORMATION: 2-amino butyric acid

<400> SEQUENCE: 17

Xaa Leu Pro His Leu Ala Arg
1               5

<210> SEQ ID NO 18
<211> LENGTH: 7
<212> TYPE: PRT
<213> ORGANISM: artificial sequence
<220> FEATURE:
<223> OTHER INFORMATION: HadruCa5-11 C3Abu variant
<220> FEATURE:
<221> NAME/KEY: variant
<222> LOCATION: (1)..(1)
<223> OTHER INFORMATION: 2-amino butyric acid

<400> SEQUENCE: 18

Xaa Ile Lys His Leu Gln Arg
1               5

<210> SEQ ID NO 19
<211> LENGTH: 7
<212> TYPE: PRT
<213> ORGANISM: artificial sequence
<220> FEATURE:
<223> OTHER INFORMATION: HadruCa5-11 C3Abu/H8A variant
<220> FEATURE:
<221> NAME/KEY: variant
<222> LOCATION: (1)..(1)
<223> OTHER INFORMATION: 2-amino butyric acid

<400> SEQUENCE: 19

Xaa Ile Lys Ala Leu Gln Arg
1               5

<210> SEQ ID NO 20
<211> LENGTH: 7
<212> TYPE: PRT
<213> ORGANISM: artificial sequence
<220> FEATURE:
<223> OTHER INFORMATION: HadruCa5-11 C3Abu/K10A variant
<220> FEATURE:
<221> NAME/KEY: variant
<222> LOCATION: (1)..(1)
<223> OTHER INFORMATION: 2-amino butyric acid

<400> SEQUENCE: 20

Xaa Ile Lys His Leu Ala Arg

<210> SEQ ID NO 21
<211> LENGTH: 11
<212> TYPE: PRT
<213> ORGANISM: artificial sequence
<220> FEATURE:
<223> OTHER INFORMATION: MCa10-20

<400> SEQUENCE: 21

Cys Lys Glu Asn Lys Asp Cys Cys Ser Lys Lys
1               5                   10

<210> SEQ ID NO 22
<211> LENGTH: 11
<212> TYPE: PRT
<213> ORGANISM: artificial sequence
<220> FEATURE:
<223> OTHER INFORMATION: MCa10-20 C10,16,17Abu variant
<220> FEATURE:
<221> NAME/KEY: variant
<222> LOCATION: (1)..(1)
<223> OTHER INFORMATION: 2-amino butyric acid
<220> FEATURE:
<221> NAME/KEY: variant
<222> LOCATION: (7)..(7)
<223> OTHER INFORMATION: 2-amino butyric acid
<220> FEATURE:
<221> NAME/KEY: variant
<222> LOCATION: (8)..(8)
<223> OTHER INFORMATION: 2-amino butyric acid

<400> SEQUENCE: 22

Xaa Lys Glu Asn Lys Asp Xaa Xaa Ser Lys Lys
1               5                   10

<210> SEQ ID NO 23
<211> LENGTH: 11
<212> TYPE: PRT
<213> ORGANISM: artificial sequence
<220> FEATURE:
<223> OTHER INFORMATION: MCa10-20 C10,16Abu variant
<220> FEATURE:
<221> NAME/KEY: variant
<222> LOCATION: (1)..(1)
<223> OTHER INFORMATION: 2-amino butyric acid
<220> FEATURE:
<221> NAME/KEY: variant
<222> LOCATION: (7)..(7)
<223> OTHER INFORMATION: 2-amino butyric acid

<400> SEQUENCE: 23

Xaa Lys Glu Asn Lys Asp Xaa Cys Ser Lys Lys
1               5                   10

<210> SEQ ID NO 24
<211> LENGTH: 11
<212> TYPE: PRT
<213> ORGANISM: artificial sequence
<220> FEATURE:
<223> OTHER INFORMATION: Opi10-20

<400> SEQUENCE: 24

Cys Lys Glu Asn Asn Asp Cys Cys Ser Lys Lys
1               5                   10

<210> SEQ ID NO 25
<211> LENGTH: 11
<212> TYPE: PRT
<213> ORGANISM: artificial sequence

```
<220> FEATURE:
<223> OTHER INFORMATION: Opi10-20 C10,16,17Abu variant
<220> FEATURE:
<221> NAME/KEY: variant
<222> LOCATION: (1)..(1)
<223> OTHER INFORMATION: 2-amino butyric acid
<220> FEATURE:
<221> NAME/KEY: variant
<222> LOCATION: (7)..(7)
<223> OTHER INFORMATION: 2-amino butyric acid
<220> FEATURE:
<221> NAME/KEY: variant
<222> LOCATION: (8)..(8)
<223> OTHER INFORMATION: 2-amino butyric acid

<400> SEQUENCE: 25

Xaa Lys Glu Asn Asn Asp Xaa Xaa Ser Lys Lys
1               5                   10

<210> SEQ ID NO 26
<211> LENGTH: 11
<212> TYPE: PRT
<213> ORGANISM: artificial sequence
<220> FEATURE:
<223> OTHER INFORMATION: Opi10-20 C10,16Abu variant
<220> FEATURE:
<221> NAME/KEY: variant
<222> LOCATION: (1)..(1)
<223> OTHER INFORMATION: 2-amino butyric acid
<220> FEATURE:
<221> NAME/KEY: variant
<222> LOCATION: (7)..(7)
<223> OTHER INFORMATION: 2-amino butyric acid

<400> SEQUENCE: 26

Xaa Lys Glu Asn Asn Asp Xaa Cys Ser Lys Lys
1               5                   10

<210> SEQ ID NO 27
<211> LENGTH: 11
<212> TYPE: PRT
<213> ORGANISM: artificial sequence
<220> FEATURE:
<223> OTHER INFORMATION: IpTx10-20

<400> SEQUENCE: 27

Cys Lys Ala Asp Asn Asp Cys Cys Gly Lys Lys
1               5                   10

<210> SEQ ID NO 28
<211> LENGTH: 11
<212> TYPE: PRT
<213> ORGANISM: artificial sequence
<220> FEATURE:
<223> OTHER INFORMATION: IpTx10-20 C10,16,17Abu variant
<220> FEATURE:
<221> NAME/KEY: variant
<222> LOCATION: (1)..(1)
<223> OTHER INFORMATION: 2-amino butyric acid
<220> FEATURE:
<221> NAME/KEY: variant
<222> LOCATION: (7)..(7)
<223> OTHER INFORMATION: 2-amino butyric acid
<220> FEATURE:
<221> NAME/KEY: variant
<222> LOCATION: (8)..(8)
<223> OTHER INFORMATION: 2-amino butyric acid

<400> SEQUENCE: 28

Xaa Lys Ala Asp Asn Asp Xaa Xaa Gly Lys Lys
1               5                   10
```

```
<210> SEQ ID NO 29
<211> LENGTH: 11
<212> TYPE: PRT
<213> ORGANISM: artificial sequence
<220> FEATURE:
<223> OTHER INFORMATION: IpTx10-20 C10,16Abu variant
<220> FEATURE:
<221> NAME/KEY: variant
<222> LOCATION: (1)..(1)
<223> OTHER INFORMATION: 2-amino butyric acid
<220> FEATURE:
<221> NAME/KEY: variant
<222> LOCATION: (7)..(7)
<223> OTHER INFORMATION: 2-amino butyric acid

<400> SEQUENCE: 29

Xaa Lys Ala Asp Asn Asp Xaa Cys Gly Lys Lys
1               5                   10

<210> SEQ ID NO 30
<211> LENGTH: 11
<212> TYPE: PRT
<213> ORGANISM: artificial sequence
<220> FEATURE:
<223> OTHER INFORMATION: HemiCa10-20

<400> SEQUENCE: 30

Cys Lys Ala Asp Lys Asp Cys Cys Ser Lys Lys
1               5                   10

<210> SEQ ID NO 31
<211> LENGTH: 11
<212> TYPE: PRT
<213> ORGANISM: artificial sequence
<220> FEATURE:
<223> OTHER INFORMATION: HemiCa10-20 C10,16,17Abu variant
<220> FEATURE:
<221> NAME/KEY: variant
<222> LOCATION: (1)..(1)
<223> OTHER INFORMATION: 2-amino butyric acid
<220> FEATURE:
<221> NAME/KEY: variant
<222> LOCATION: (7)..(7)
<223> OTHER INFORMATION: 2-amino butyric acid
<220> FEATURE:
<221> NAME/KEY: variant
<222> LOCATION: (8)..(8)
<223> OTHER INFORMATION: 2-amino butyric acid

<400> SEQUENCE: 31

Xaa Lys Ala Asp Lys Asp Xaa Xaa Ser Lys Lys
1               5                   10

<210> SEQ ID NO 32
<211> LENGTH: 11
<212> TYPE: PRT
<213> ORGANISM: artificial sequence
<220> FEATURE:
<223> OTHER INFORMATION: HemiCa10-20 C10,16Abu variant
<220> FEATURE:
<221> NAME/KEY: variant
<222> LOCATION: (1)..(1)
<223> OTHER INFORMATION: 2-aminobutyric acid
<220> FEATURE:
<221> NAME/KEY: variant
<222> LOCATION: (7)..(7)
<223> OTHER INFORMATION: 2-aminobutyric acid

<400> SEQUENCE: 32

Xaa Lys Ala Asp Lys Asp Xaa Cys Ser Lys Lys
1               5                   10
```

```
<210> SEQ ID NO 33
<211> LENGTH: 11
<212> TYPE: PRT
<213> ORGANISM: artificial sequence
<220> FEATURE:
<223> OTHER INFORMATION: HadruCa12-22

<400> SEQUENCE: 33

Cys Arg Glu Asn Lys Asp Cys Cys Ser Lys Lys
1               5                   10

<210> SEQ ID NO 34
<211> LENGTH: 11
<212> TYPE: PRT
<213> ORGANISM: artificial sequence
<220> FEATURE:
<223> OTHER INFORMATION: HadruCa12-22 C12,18,19Abu variant
<220> FEATURE:
<221> NAME/KEY: variant
<222> LOCATION: (1)..(1)
<223> OTHER INFORMATION: 2-amino butyric acid
<220> FEATURE:
<221> NAME/KEY: variant
<222> LOCATION: (7)..(7)
<223> OTHER INFORMATION: 2-amino butyric acid
<220> FEATURE:
<221> NAME/KEY: variant
<222> LOCATION: (8)..(8)
<223> OTHER INFORMATION: 2-amino butyric acid

<400> SEQUENCE: 34

Xaa Arg Glu Asn Lys Asp Xaa Xaa Ser Lys Lys
1               5                   10

<210> SEQ ID NO 35
<211> LENGTH: 11
<212> TYPE: PRT
<213> ORGANISM: artificial sequence
<220> FEATURE:
<223> OTHER INFORMATION: HadruCa12-22 C12,18 Abu variant
<220> FEATURE:
<221> NAME/KEY: variant
<222> LOCATION: (1)..(1)
<223> OTHER INFORMATION: 2-amino butyric acid
<220> FEATURE:
<221> NAME/KEY: variant
<222> LOCATION: (7)..(7)
<223> OTHER INFORMATION: 2-amino butyric acid

<400> SEQUENCE: 35

Xaa Arg Glu Asn Lys Asp Xaa Cys Ser Lys Lys
1               5                   10

<210> SEQ ID NO 36
<211> LENGTH: 9
<212> TYPE: PRT
<213> ORGANISM: artificial sequence
<220> FEATURE:
<223> OTHER INFORMATION: MCa1-9

<400> SEQUENCE: 36

Gly Asp Cys Leu Pro His Leu Lys Leu
1               5

<210> SEQ ID NO 37
<211> LENGTH: 15
<212> TYPE: PRT
<213> ORGANISM: artificial sequence
<220> FEATURE:
```

<223> OTHER INFORMATION: MCa1-15

<400> SEQUENCE: 37

Gly Asp Cys Leu Pro His Leu Lys Leu Cys Lys Glu Asn Lys Asp
1               5                   10                  15

<210> SEQ ID NO 38
<211> LENGTH: 11
<212> TYPE: PRT
<213> ORGANISM: artificial sequence
<220> FEATURE:
<223> OTHER INFORMATION: MCa1-15delta 12-15

<400> SEQUENCE: 38

Gly Asp Cys Leu Pro His Leu Lys Leu Cys Lys
1               5                   10

<210> SEQ ID NO 39
<211> LENGTH: 14
<212> TYPE: PRT
<213> ORGANISM: artificial sequence
<220> FEATURE:
<223> OTHER INFORMATION: MCa1-15delta12

<400> SEQUENCE: 39

Gly Asp Cys Leu Pro His Leu Lys Leu Cys Lys Asn Lys Asp
1               5                   10

<210> SEQ ID NO 40
<211> LENGTH: 14
<212> TYPE: PRT
<213> ORGANISM: artificial sequence
<220> FEATURE:
<223> OTHER INFORMATION: MCa1-15delta15

<400> SEQUENCE: 40

Gly Asp Cys Leu Pro His Leu Lys Leu Cys Lys Glu Asn Lys
1               5                   10

<210> SEQ ID NO 41
<211> LENGTH: 16
<212> TYPE: PRT
<213> ORGANISM: artificial sequence
<220> FEATURE:
<223> OTHER INFORMATION: MCa1-20delta12-15

<400> SEQUENCE: 41

Gly Asp Cys Leu Pro His Leu Lys Leu Cys Lys Cys Cys Ser Lys Lys
1               5                   10                  15

<210> SEQ ID NO 42
<211> LENGTH: 19
<212> TYPE: PRT
<213> ORGANISM: artificial sequence
<220> FEATURE:
<223> OTHER INFORMATION: MCa1-20delta12

<400> SEQUENCE: 42

Gly Asp Cys Leu Pro His Leu Lys Leu Cys Lys Asn Lys Asp Cys Cys
1               5                   10                  15

Ser Lys Lys

<210> SEQ ID NO 43
<211> LENGTH: 19
<212> TYPE: PRT
<213> ORGANISM: artificial sequence -continued

```
<220> FEATURE:
<223> OTHER INFORMATION: MCa1-20delta15

<400> SEQUENCE: 43

Gly Asp Cys Leu Pro His Leu Lys Leu Cys Lys Glu Asn Lys Cys Cys
1               5                   10                  15

Ser Lys Lys

<210> SEQ ID NO 44
<211> LENGTH: 9
<212> TYPE: PRT
<213> ORGANISM: artificial sequence
<220> FEATURE:
<223> OTHER INFORMATION: MCa1-9 C3Abu variant
<220> FEATURE:
<221> NAME/KEY: VARIANT
<222> LOCATION: (3)..(3)
<223> OTHER INFORMATION: 2-amino butyric acid

<400> SEQUENCE: 44

Gly Asp Xaa Leu Pro His Leu Lys Leu
1               5

<210> SEQ ID NO 45
<211> LENGTH: 9
<212> TYPE: PRT
<213> ORGANISM: artificial sequence
<220> FEATURE:
<223> OTHER INFORMATION: MCa1-9 D2A/C3Abu variant
<220> FEATURE:
<221> NAME/KEY: VARIANT
<222> LOCATION: (3)..(3)
<223> OTHER INFORMATION: 2-amino butyric acid

<400> SEQUENCE: 45

Gly Ala Xaa Leu Pro His Leu Lys Leu
1               5

<210> SEQ ID NO 46
<211> LENGTH: 15
<212> TYPE: PRT
<213> ORGANISM: artificial sequence
<220> FEATURE:
<223> OTHER INFORMATION: MCa1-15 C3,10Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid

<400> SEQUENCE: 46

Gly Asp Xaa Leu Pro His Leu Lys Leu Xaa Lys Glu Asn Lys Asp
1               5                   10                  15

<210> SEQ ID NO 47
<211> LENGTH: 15
<212> TYPE: PRT
<213> ORGANISM: artificial sequence
<220> FEATURE:
<223> OTHER INFORMATION: MCa1-15 D2A/C3,10Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
```

<223> OTHER INFORMATION: 2-amino butyric acid

<400> SEQUENCE: 47

Gly Ala Xaa Leu Pro His Leu Lys Leu Xaa Lys Glu Asn Lys Asp
1               5                   10                  15

<210> SEQ ID NO 48
<211> LENGTH: 15
<212> TYPE: PRT
<213> ORGANISM: artificial sequence
<220> FEATURE:
<223> OTHER INFORMATION: MCa1-15 H6A/C3,10Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid

<400> SEQUENCE: 48

Gly Asp Xaa Leu Pro Ala Leu Lys Leu Xaa Lys Glu Asn Lys Asp
1               5                   10                  15

<210> SEQ ID NO 49
<211> LENGTH: 15
<212> TYPE: PRT
<213> ORGANISM: artificial sequence
<220> FEATURE:
<223> OTHER INFORMATION: MCa1-15 K8A/C3,10Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid

<400> SEQUENCE: 49

Gly Asp Xaa Leu Pro His Leu Ala Leu Xaa Lys Glu Asn Lys Asp
1               5                   10                  15

<210> SEQ ID NO 50
<211> LENGTH: 15
<212> TYPE: PRT
<213> ORGANISM: artificial sequence
<220> FEATURE:
<223> OTHER INFORMATION: MCa1-15 E12A/C3,10Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid

<400> SEQUENCE: 50

Gly Asp Xaa Leu Pro His Leu Ala Leu Xaa Lys Ala Asn Lys Asp
1               5                   10                  15

<210> SEQ ID NO 51
<211> LENGTH: 15
<212> TYPE: PRT
<213> ORGANISM: artificial sequence
<220> FEATURE:
<223> OTHER INFORMATION: MCa1-15 D15A/C3,10Abu variant
<220> FEATURE:
<221> NAME/KEY: VARIANT

```
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid

<400> SEQUENCE: 51

Gly Asp Xaa Leu Pro His Leu Ala Leu Xaa Lys Glu Asn Lys Ala
1               5                   10                  15

<210> SEQ ID NO 52
<211> LENGTH: 11
<212> TYPE: PRT
<213> ORGANISM: artificial sequence
<220> FEATURE:
<223> OTHER INFORMATION: MCa1-15delta12-15 C3,10Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid

<400> SEQUENCE: 52

Gly Asp Xaa Leu Pro His Leu Lys Leu Val Lys
1               5                   10

<210> SEQ ID NO 53
<211> LENGTH: 11
<212> TYPE: PRT
<213> ORGANISM: artificial sequence
<220> FEATURE:
<223> OTHER INFORMATION: MCa1-15delta12-15 D2A/C3,10Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid

<400> SEQUENCE: 53

Gly Ala Xaa Leu Pro His Leu Lys Leu Xaa Lys
1               5                   10

<210> SEQ ID NO 54
<211> LENGTH: 11
<212> TYPE: PRT
<213> ORGANISM: artificial sequence
<220> FEATURE:
<223> OTHER INFORMATION: MCa1-15delta12-15 H6A/C3,10Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid

<400> SEQUENCE: 54

Gly Asp Xaa Leu Pro Ala Leu Lys Leu Ser Lys
1               5                   10

<210> SEQ ID NO 55
<211> LENGTH: 11
<212> TYPE: PRT
```

-continued

```
<213> ORGANISM: artificial sequence
<220> FEATURE:
<223> OTHER INFORMATION: MCa1-15delta12-15 K8A/C3,10Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid

<400> SEQUENCE: 55

Gly Asp Xaa Leu Pro His Leu Ala Leu Xaa Lys
1               5                   10

<210> SEQ ID NO 56
<211> LENGTH: 14
<212> TYPE: PRT
<213> ORGANISM: artificial sequence
<220> FEATURE:
<223> OTHER INFORMATION: MCa1-15delta12 C3,10Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid

<400> SEQUENCE: 56

Gly Asp Xaa Leu Pro His Leu Lys Leu Xaa Lys Asn Lys Asp
1               5                   10

<210> SEQ ID NO 57
<211> LENGTH: 14
<212> TYPE: PRT
<213> ORGANISM: artificial sequence
<220> FEATURE:
<223> OTHER INFORMATION: MCa1-15delta12 D2A/C3,10Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid

<400> SEQUENCE: 57

Gly Ala Xaa Leu Pro His Leu Lys Leu Xaa Lys Asn Lys Asp
1               5                   10

<210> SEQ ID NO 58
<211> LENGTH: 14
<212> TYPE: PRT
<213> ORGANISM: artificial sequence
<220> FEATURE:
<223> OTHER INFORMATION: MCa1-15delta12 H6A/C3,10Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid

<400> SEQUENCE: 58

Gly Asp Xaa Leu Pro Ala Leu Lys Leu Xaa Lys Asn Lys Asp
1               5                   10
```

```
<210> SEQ ID NO 59
<211> LENGTH: 14
<212> TYPE: PRT
<213> ORGANISM: artificial sequence
<220> FEATURE:
<223> OTHER INFORMATION: MCa1-15delta12 K8A/C3,10Abu
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid

<400> SEQUENCE: 59

Gly Asp Xaa Leu Pro His Leu Ala Leu Xaa Lys Asn Lys Asp
1               5                   10

<210> SEQ ID NO 60
<211> LENGTH: 14
<212> TYPE: PRT
<213> ORGANISM: artificial sequence
<220> FEATURE:
<223> OTHER INFORMATION: MCa1-15delta12 D15A/C3,10Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid

<400> SEQUENCE: 60

Gly Asp Xaa Leu Pro His Leu Ala Leu Xaa Lys Asn Lys Ala
1               5                   10

<210> SEQ ID NO 61
<211> LENGTH: 14
<212> TYPE: PRT
<213> ORGANISM: artificial sequence
<220> FEATURE:
<223> OTHER INFORMATION: MCa1-15delta15 C3,10Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid

<400> SEQUENCE: 61

Gly Asp Xaa Leu Pro His Leu Lys Leu Xaa Lys Glu Asn Lys
1               5                   10

<210> SEQ ID NO 62
<211> LENGTH: 14
<212> TYPE: PRT
<213> ORGANISM: artificial sequence
<220> FEATURE:
<223> OTHER INFORMATION: MCa1-15delta15 D2A/C3,10Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
```

```
<400> SEQUENCE: 62

Gly Ala Xaa Leu Pro His Leu Lys Leu Xaa Lys Glu Asn Lys
1               5                   10

<210> SEQ ID NO 63
<211> LENGTH: 14
<212> TYPE: PRT
<213> ORGANISM: artificial sequence
<220> FEATURE:
<223> OTHER INFORMATION: MCa1-15delta15 H6A/C3,10Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid

<400> SEQUENCE: 63

Gly Asp Xaa Leu Pro Ala Leu Lys Leu Xaa Lys Glu Asn Lys
1               5                   10

<210> SEQ ID NO 64
<211> LENGTH: 14
<212> TYPE: PRT
<213> ORGANISM: artificial sequence
<220> FEATURE:
<223> OTHER INFORMATION: MCa1-15delta15 K8A/C3,10Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid

<400> SEQUENCE: 64

Gly Asp Xaa Leu Pro His Leu Ala Leu Xaa Lys Glu Asn Lys
1               5                   10

<210> SEQ ID NO 65
<211> LENGTH: 14
<212> TYPE: PRT
<213> ORGANISM: artificial sequence
<220> FEATURE:
<223> OTHER INFORMATION: MCa1-15delta15 E12A/C3,10Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid

<400> SEQUENCE: 65

Gly Asp Xaa Leu Pro His Leu Lys Leu Xaa Lys Ala Asn Lys
1               5                   10

<210> SEQ ID NO 66
<211> LENGTH: 20
<212> TYPE: PRT
<213> ORGANISM: artificial sequence
<220> FEATURE:
<223> OTHER INFORMATION: MCa1-20 C3,10,16,17Abu variant
<220> FEATURE:
<221> NAME/KEY: VARIANT
<222> LOCATION: (3)..(3)
```

```
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid
<220> FEATURE:
<221> NAME/KEY: VARIANT
<222> LOCATION: (17)..(17)
<223> OTHER INFORMATION: 2-amino butyric acid

<400> SEQUENCE: 66

Gly Asp Xaa Leu Pro His Leu Lys Leu Xaa Lys Glu Asn Lys Asp Xaa
1               5                   10                  15

Xaa Ser Lys Lys
            20

<210> SEQ ID NO 67
<211> LENGTH: 20
<212> TYPE: PRT
<213> ORGANISM: artificial sequence
<220> FEATURE:
<223> OTHER INFORMATION: MCa1-20 D2A/C3,10,16,17Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid
<220> FEATURE:
<221> NAME/KEY: VARIANT
<222> LOCATION: (17)..(17)
<223> OTHER INFORMATION: 2-amino butyric acid

<400> SEQUENCE: 67

Gly Ala Xaa Leu Pro His Leu Lys Leu Xaa Lys Glu Asn Lys Asp Xaa
1               5                   10                  15

Xaa Ser Lys Lys
            20

<210> SEQ ID NO 68
<211> LENGTH: 20
<212> TYPE: PRT
<213> ORGANISM: artificial sequence
<220> FEATURE:
<223> OTHER INFORMATION: MCa1-20 H6A/C3,10,16,17Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid
<220> FEATURE:
<221> NAME/KEY: VARIANT
<222> LOCATION: (17)..(17)
<223> OTHER INFORMATION: 2-amino butyric acid

<400> SEQUENCE: 68
```

```
Gly Asp Xaa Leu Pro Ala Leu Lys Leu Xaa Lys Glu Asn Lys Asp Xaa
1               5                   10                  15
Xaa Ser Lys Lys
            20

<210> SEQ ID NO 69
<211> LENGTH: 20
<212> TYPE: PRT
<213> ORGANISM: artificial sequence
<220> FEATURE:
<223> OTHER INFORMATION: MCa1-20 K8A/C3,10,16,17Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid
<220> FEATURE:
<221> NAME/KEY: VARIANT
<222> LOCATION: (17)..(17)
<223> OTHER INFORMATION: 2-amino butyric acid

<400> SEQUENCE: 69

Gly Asp Xaa Leu Pro His Leu Ala Leu Xaa Lys Glu Asn Lys Asp Xaa
1               5                   10                  15
Xaa Ser Lys Lys
            20

<210> SEQ ID NO 70
<211> LENGTH: 20
<212> TYPE: PRT
<213> ORGANISM: artificial sequence
<220> FEATURE:
<223> OTHER INFORMATION: MCa1-20 D15A/C3,10,16,17Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid
<220> FEATURE:
<221> NAME/KEY: VARIANT
<222> LOCATION: (17)..(17)
<223> OTHER INFORMATION: 2-amino butyric acid

<400> SEQUENCE: 70

Gly Asp Xaa Leu Pro His Leu Lys Leu Xaa Lys Glu Asn Lys Ala Xaa
1               5                   10                  15
Xaa Ser Lys Lys
            20

<210> SEQ ID NO 71
<211> LENGTH: 20
<212> TYPE: PRT
<213> ORGANISM: artificial sequence
<220> FEATURE:
<223> OTHER INFORMATION: MCa1-20 E12A/C3,6,10,16,17Abu variant
<220> FEATURE:
```

-continued

```
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid
<220> FEATURE:
<221> NAME/KEY: VARIANT
<222> LOCATION: (17)..(17)
<223> OTHER INFORMATION: 2-amino butyric acid

<400> SEQUENCE: 71

Gly Asp Xaa Leu Pro His Leu Lys Leu Xaa Lys Ala Asn Lys Asp Xaa
1               5                   10                  15

Xaa Ser Lys Lys
            20

<210> SEQ ID NO 72
<211> LENGTH: 16
<212> TYPE: PRT
<213> ORGANISM: artificial sequence
<220> FEATURE:
<223> OTHER INFORMATION: MCa1-20delta12-15 C3,10,16,17Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (12)..(12)
<223> OTHER INFORMATION: 2-amino butyric acid
<220> FEATURE:
<221> NAME/KEY: VARIANT
<222> LOCATION: (13)..(13)
<223> OTHER INFORMATION: 2-amino butyric acid

<400> SEQUENCE: 72

Gly Asp Xaa Leu Pro His Leu Lys Leu Xaa Lys Xaa Xaa Ser Lys Lys
1               5                   10                  15

<210> SEQ ID NO 73
<211> LENGTH: 16
<212> TYPE: PRT
<213> ORGANISM: artificial sequence
<220> FEATURE:
<223> OTHER INFORMATION: MCa1-20delta12-15 D2A/C3,10,16,17Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (12)..(12)
<223> OTHER INFORMATION: 2-amino butyric acid
<220> FEATURE:
<221> NAME/KEY: VARIANT
<222> LOCATION: (13)..(13)
<223> OTHER INFORMATION: 2-amino butyric acid

<400> SEQUENCE: 73
```

-continued

Gly Ala Xaa Leu Pro His Leu Lys Leu Xaa Lys Xaa Xaa Ser Lys Lys
1               5                   10                  15

<210> SEQ ID NO 74
<211> LENGTH: 16
<212> TYPE: PRT
<213> ORGANISM: artificial sequence
<220> FEATURE:
<223> OTHER INFORMATION: MCa1-20delta12-15 H6A/C3,10,16,17Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (12)..(12)
<223> OTHER INFORMATION: 2-amino butyric acid
<220> FEATURE:
<221> NAME/KEY: VARIANT
<222> LOCATION: (13)..(13)
<223> OTHER INFORMATION: 2-amino butyric acid

<400> SEQUENCE: 74

Gly Asp Xaa Leu Pro Ala Leu Lys Leu Xaa Lys Xaa Xaa Ser Lys Lys
1               5                   10                  15

<210> SEQ ID NO 75
<211> LENGTH: 16
<212> TYPE: PRT
<213> ORGANISM: artificial sequence
<220> FEATURE:
<223> OTHER INFORMATION: MCa1-20delta12-15 K8A/C3,10,16,17Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (12)..(12)
<223> OTHER INFORMATION: 2-amino butyric acid
<220> FEATURE:
<221> NAME/KEY: VARIANT
<222> LOCATION: (13)..(13)
<223> OTHER INFORMATION: 2-amino butyric acid

<400> SEQUENCE: 75

Gly Asp Xaa Leu Pro His Leu Ala Leu Xaa Lys Xaa Xaa Ser Lys Lys
1               5                   10                  15

<210> SEQ ID NO 76
<211> LENGTH: 19
<212> TYPE: PRT
<213> ORGANISM: artificial sequence
<220> FEATURE:
<223> OTHER INFORMATION: MCa1-20delta12 C3,10,16,17Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (15)..(15)

```
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid

<400> SEQUENCE: 76

Gly Asp Xaa Leu Pro His Leu Lys Leu Xaa Lys Asn Lys Asp Xaa Xaa
1               5                   10                  15

Ser Lys Lys

<210> SEQ ID NO 77
<211> LENGTH: 19
<212> TYPE: PRT
<213> ORGANISM: artificial sequence
<220> FEATURE:
<223> OTHER INFORMATION: MCa1-20delta12 D2A/C3,10,16,17Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (15)..(15)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid

<400> SEQUENCE: 77

Gly Ala Xaa Leu Pro His Leu Lys Leu Xaa Lys Asn Lys Asp Xaa Xaa
1               5                   10                  15

Ser Lys Lys

<210> SEQ ID NO 78
<211> LENGTH: 19
<212> TYPE: PRT
<213> ORGANISM: artificial sequence
<220> FEATURE:
<223> OTHER INFORMATION: MCa1-20delta12 H6A/C3,10,16,17Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (15)..(15)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid

<400> SEQUENCE: 78

Gly Asp Xaa Leu Pro Ala Leu Lys Leu Xaa Lys Asn Lys Asp Xaa Xaa
1               5                   10                  15

Ser Lys Lys

<210> SEQ ID NO 79
<211> LENGTH: 19
<212> TYPE: PRT
```

```
<213> ORGANISM: artificial sequence
<220> FEATURE:
<223> OTHER INFORMATION: MCa1-20delta12 K8A/C3,10,16,17Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (15)..(15)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid

<400> SEQUENCE: 79

Gly Asp Xaa Leu Pro His Leu Ala Leu Xaa Lys Asn Lys Asp Xaa Xaa
1               5                   10                  15

Ser Lys Lys

<210> SEQ ID NO 80
<211> LENGTH: 19
<212> TYPE: PRT
<213> ORGANISM: artificial sequence
<220> FEATURE:
<223> OTHER INFORMATION: MCa1-20delta12 D15A/C3,10,16,17Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (15)..(15)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid

<400> SEQUENCE: 80

Gly Asp Xaa Leu Pro His Leu Lys Leu Xaa Lys Asn Lys Ala Xaa Xaa
1               5                   10                  15

Ser Lys Lys

<210> SEQ ID NO 81
<211> LENGTH: 19
<212> TYPE: PRT
<213> ORGANISM: artificial sequence
<220> FEATURE:
<223> OTHER INFORMATION: MCa1-20delta15 C3,10,16,17Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (15)..(15)
<223> OTHER INFORMATION: 2-amino butyric acid
<220> FEATURE:
<221> NAME/KEY: VARIANT
```

-continued

```
<222> LOCATION: (16)..(16)
<223> OTHER INFORMATION: 2-amino butyric acid

<400> SEQUENCE: 81

Gly Asp Xaa Leu Pro His Leu Lys Leu Xaa Lys Glu Asn Lys Xaa Xaa
1               5                   10                  15

Ser Lys Lys

<210> SEQ ID NO 82
<211> LENGTH: 19
<212> TYPE: PRT
<213> ORGANISM: artificial sequence
<220> FEATURE:
<223> OTHER INFORMATION: MCa1-20delta15 D2A/C3,10,16,17Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (15)..(15)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid

<400> SEQUENCE: 82

Gly Ala Xaa Leu Pro His Leu Lys Leu Xaa Lys Glu Asn Lys Xaa Xaa
1               5                   10                  15

Ser Lys Lys

<210> SEQ ID NO 83
<211> LENGTH: 19
<212> TYPE: PRT
<213> ORGANISM: artificial sequence
<220> FEATURE:
<223> OTHER INFORMATION: MCa1-20delta15 H6A/C3,10,16,17Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (15)..(15)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid

<400> SEQUENCE: 83

Gly Asp Xaa Leu Pro Ala Leu Lys Leu Xaa Lys Glu Asn Lys Xaa Xaa
1               5                   10                  15

Ser Lys Lys

<210> SEQ ID NO 84
<211> LENGTH: 19
<212> TYPE: PRT
<213> ORGANISM: artificial sequence
<220> FEATURE:
<223> OTHER INFORMATION: MCa1-20delta15 K8A/C3,10,16,17Abu variant
```

```
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (15)..(15)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid

<400> SEQUENCE: 84

Gly Asp Xaa Leu Pro His Leu Ala Leu Xaa Lys Glu Asn Lys Xaa Xaa
1               5                   10                  15

Ser Lys Lys

<210> SEQ ID NO 85
<211> LENGTH: 19
<212> TYPE: PRT
<213> ORGANISM: artificial sequence
<220> FEATURE:
<223> OTHER INFORMATION: MCa1-20delta15 E12A/C3,10,16,17Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (15)..(15)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid

<400> SEQUENCE: 85

Gly Asp Xaa Leu Pro His Leu Lys Leu Xaa Lys Ala Asn Lys Xaa Xaa
1               5                   10                  15

Ser Lys Lys

<210> SEQ ID NO 86
<211> LENGTH: 20
<212> TYPE: PRT
<213> ORGANISM: artificial sequence
<220> FEATURE:
<223> OTHER INFORMATION: MCa1-20F C10,16Abu variant
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid

<400> SEQUENCE: 86

Gly Asp Cys Leu Pro His Leu Lys Leu Xaa Lys Glu Asn Lys Asp Xaa
1               5                   10                  15

Cys Ser Lys Lys
            20
```

```
<210> SEQ ID NO 87
<211> LENGTH: 20
<212> TYPE: PRT
<213> ORGANISM: artificial sequence
<220> FEATURE:
<223> OTHER INFORMATION: MCa1-20F D2A/C10,16Abu variant
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid

<400> SEQUENCE: 87

Gly Ala Cys Leu Pro His Leu Lys Leu Xaa Lys Glu Asn Lys Asp Xaa
1               5                   10                  15
Cys Ser Lys Lys
            20

<210> SEQ ID NO 88
<211> LENGTH: 20
<212> TYPE: PRT
<213> ORGANISM: artificial sequence
<220> FEATURE:
<223> OTHER INFORMATION: MCa1-20F H6A/C10,16Abu variant
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid

<400> SEQUENCE: 88

Gly Asp Cys Leu Pro Ala Leu Lys Leu Xaa Lys Glu Asn Lys Asp Xaa
1               5                   10                  15
Cys Ser Lys Lys
            20

<210> SEQ ID NO 89
<211> LENGTH: 20
<212> TYPE: PRT
<213> ORGANISM: artificial sequence
<220> FEATURE:
<223> OTHER INFORMATION: MCa1-20F K8A/C10,16Abu variant
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid

<400> SEQUENCE: 89

Gly Asp Cys Leu Pro His Leu Ala Leu Xaa Lys Glu Asn Lys Asp Xaa
1               5                   10                  15
Cys Ser Lys Lys
            20

<210> SEQ ID NO 90
<211> LENGTH: 20
<212> TYPE: PRT
<213> ORGANISM: artificial sequence
<220> FEATURE:
<223> OTHER INFORMATION: MCa1-20F D15A/C10,16Abu variant
```

```
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid

<400> SEQUENCE: 90

Gly Asp Cys Leu Pro His Leu Lys Leu Xaa Lys Glu Asn Lys Ala Xaa
1               5                   10                  15

Cys Ser Lys Lys
            20

<210> SEQ ID NO 91
<211> LENGTH: 20
<212> TYPE: PRT
<213> ORGANISM: artificial sequence
<220> FEATURE:
<223> OTHER INFORMATION: MCa1-20F E12A/C10,16Abu variant
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid

<400> SEQUENCE: 91

Gly Asp Cys Leu Pro His Leu Lys Leu Xaa Lys Ala Asn Lys Asp Xaa
1               5                   10                  15

Cys Ser Lys Lys
            20

<210> SEQ ID NO 92
<211> LENGTH: 16
<212> TYPE: PRT
<213> ORGANISM: artificial sequence
<220> FEATURE:
<223> OTHER INFORMATION: MCa1-20delta12-15 C10,16Abu variant
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (12)..(12)
<223> OTHER INFORMATION: 2-amino butyric acid

<400> SEQUENCE: 92

Gly Asp Cys Leu Pro His Leu Lys Leu Xaa Lys Xaa Cys Ser Lys Lys
1               5                   10                  15

<210> SEQ ID NO 93
<211> LENGTH: 16
<212> TYPE: PRT
<213> ORGANISM: artificial sequence
<220> FEATURE:
<223> OTHER INFORMATION: MCa1-20delta12-15 D2A/C10,16Abu variant
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (12)..(12)
<223> OTHER INFORMATION: 2-amino butyric acid

<400> SEQUENCE: 93
```

Gly Ala Cys Leu Pro His Leu Lys Leu Xaa Lys Xaa Cys Ser Lys Lys
1               5                   10                  15

<210> SEQ ID NO 94
<211> LENGTH: 16
<212> TYPE: PRT
<213> ORGANISM: artificial sequence
<220> FEATURE:
<223> OTHER INFORMATION: MCa1-20delta12-15 H6A/C10,16Abu variant
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (12)..(12)
<223> OTHER INFORMATION: 2-amino butyric acid

<400> SEQUENCE: 94

Gly Asp Cys Leu Pro Ala Leu Lys Leu Xaa Lys Xaa Cys Ser Lys Lys
1               5                   10                  15

<210> SEQ ID NO 95
<211> LENGTH: 16
<212> TYPE: PRT
<213> ORGANISM: artificial sequence
<220> FEATURE:
<223> OTHER INFORMATION: MCa1-20delta12-15 K8A/C10,16Abu variant
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (12)..(12)
<223> OTHER INFORMATION: 2-amino butyric acid

<400> SEQUENCE: 95

Gly Asp Cys Leu Pro His Leu Ala Leu Xaa Lys Xaa Cys Ser Lys Lys
1               5                   10                  15

<210> SEQ ID NO 96
<211> LENGTH: 19
<212> TYPE: PRT
<213> ORGANISM: artificial sequence
<220> FEATURE:
<223> OTHER INFORMATION: MCa1-20delta12 C10,16Abu variant
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (15)..(15)
<223> OTHER INFORMATION: 2-amino butyric acid

<400> SEQUENCE: 96

Gly Asp Cys Leu Pro His Leu Lys Leu Xaa Lys Asn Lys Asp Xaa Cys
1               5                   10                  15

Ser Lys Lys

<210> SEQ ID NO 97
<211> LENGTH: 19
<212> TYPE: PRT
<213> ORGANISM: artificial sequence
<220> FEATURE:
<223> OTHER INFORMATION: MCa1-20delta12 D2A/C10,16Abu variant
<220> FEATURE:
<221> NAME/KEY: VARIANT
<222> LOCATION: (10)..(10)

<223> OTHER INFORMATION: 2-amino butyric acid
<220> FEATURE:
<221> NAME/KEY: VARIANT
<222> LOCATION: (15)..(15)
<223> OTHER INFORMATION: 2-amino butyric acid

<400> SEQUENCE: 97

Gly Ala Cys Leu Pro His Leu Lys Leu Xaa Lys Asn Lys Asp Xaa Cys
1               5                   10                  15

Ser Lys Lys

<210> SEQ ID NO 98
<211> LENGTH: 19
<212> TYPE: PRT
<213> ORGANISM: artificial sequence
<220> FEATURE:
<223> OTHER INFORMATION: MCa1-20delta12 H6A/C10,16Abu variant
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (15)..(15)
<223> OTHER INFORMATION: 2-amino butyric acid

<400> SEQUENCE: 98

Gly Asp Cys Leu Pro Ala Leu Lys Leu Xaa Lys Asn Lys Asp Xaa Cys
1               5                   10                  15

Ser Lys Lys

<210> SEQ ID NO 99
<211> LENGTH: 19
<212> TYPE: PRT
<213> ORGANISM: artificial sequence
<220> FEATURE:
<223> OTHER INFORMATION: MCa1-20delta12 K8A/C10,16Abu variant
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (15)..(15)
<223> OTHER INFORMATION: 2-amino butyric acid

<400> SEQUENCE: 99

Gly Asp Cys Leu Pro His Leu Ala Leu Xaa Lys Asn Lys Asp Xaa Cys
1               5                   10                  15

Ser Lys Lys

<210> SEQ ID NO 100
<211> LENGTH: 19
<212> TYPE: PRT
<213> ORGANISM: artificial sequence
<220> FEATURE:
<223> OTHER INFORMATION: MCa1-20delta12 D15A/C10,16Abu variant
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (15)..(15)
<223> OTHER INFORMATION: 2-amino butyric acid

<400> SEQUENCE: 100

Gly Asp Cys Leu Pro His Leu Lys Leu Xaa Lys Asn Lys Ala Xaa Cys
1               5                   10                  15

Ser Lys Lys

<210> SEQ ID NO 101
<211> LENGTH: 19
<212> TYPE: PRT
<213> ORGANISM: artificial sequence
<220> FEATURE:
<223> OTHER INFORMATION: MCa1-20delta15 C10,16Abu variant
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (15)..(15)
<223> OTHER INFORMATION: 2-amino butyric acid

<400> SEQUENCE: 101

Gly Asp Cys Leu Pro His Leu Lys Leu Xaa Lys Glu Asn Lys Xaa Cys
1               5                   10                  15

Ser Lys Lys

<210> SEQ ID NO 102
<211> LENGTH: 19
<212> TYPE: PRT
<213> ORGANISM: artificial sequence
<220> FEATURE:
<223> OTHER INFORMATION: MCa1-20delta15 D2A/C10,16Abu variant
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (15)..(15)
<223> OTHER INFORMATION: 2-amino butyric acid

<400> SEQUENCE: 102

Gly Ala Cys Leu Pro His Leu Lys Leu Xaa Lys Glu Asn Lys Xaa Cys
1               5                   10                  15

Ser Lys Lys

<210> SEQ ID NO 103
<211> LENGTH: 19
<212> TYPE: PRT
<213> ORGANISM: artificial sequence
<220> FEATURE:
<223> OTHER INFORMATION: MCa1-20delta15 H6A/C10,16Abu variant
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (15)..(15)
<223> OTHER INFORMATION: 2-amino butyric acid

<400> SEQUENCE: 103

Gly Asp Cys Leu Pro Ala Leu Lys Leu Xaa Lys Glu Asn Lys Xaa Cys
1               5                   10                  15

Ser Lys Lys

<210> SEQ ID NO 104
<211> LENGTH: 19
<212> TYPE: PRT
<213> ORGANISM: artificial sequence
<220> FEATURE:
<223> OTHER INFORMATION: MCa1-20delta15 K8A/C10,16Abu variant

```
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (15)..(15)
<223> OTHER INFORMATION: 2-amino butyric acid

<400> SEQUENCE: 104

Gly Asp Cys Leu Pro His Leu Ala Leu Xaa Lys Glu Asn Lys Xaa Cys
1               5                   10                  15

Ser Lys Lys

<210> SEQ ID NO 105
<211> LENGTH: 19
<212> TYPE: PRT
<213> ORGANISM: artificial sequence
<220> FEATURE:
<223> OTHER INFORMATION: MCa1-20delta15 E12A/C10,16Abu variant
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (15)..(15)
<223> OTHER INFORMATION: 2-amino butyric acid

<400> SEQUENCE: 105

Gly Asp Cys Leu Pro His Leu Lys Leu Xaa Lys Ala Asn Lys Xaa Cys
1               5                   10                  15

Ser Lys Lys

<210> SEQ ID NO 106
<211> LENGTH: 20
<212> TYPE: PRT
<213> ORGANISM: artificial sequence
<220> FEATURE:
<223> OTHER INFORMATION: MCa6-25

<400> SEQUENCE: 106

His Leu Lys Leu Cys Lys Glu Asn Lys Asp Cys Cys Ser Lys Lys Cys
1               5                   10                  15

Lys Arg Arg Gly
            20

<210> SEQ ID NO 107
<211> LENGTH: 16
<212> TYPE: PRT
<213> ORGANISM: artificial sequence
<220> FEATURE:
<223> OTHER INFORMATION: MCa18-33

<400> SEQUENCE: 107

Ser Lys Lys Cys Lys Arg Arg Gly Thr Asn Ile Glu Lys Arg Cys Arg
1               5                   10                  15

<210> SEQ ID NO 108
<211> LENGTH: 8
<212> TYPE: PRT
<213> ORGANISM: artificial sequence
<220> FEATURE:
<223> OTHER INFORMATION: MCa18-25

<400> SEQUENCE: 108

Ser Lys Lys Cys Lys Arg Arg Gly
1               5
```

```
1               5

<210> SEQ ID NO 109
<211> LENGTH: 12
<212> TYPE: PRT
<213> ORGANISM: artificial sequence
<220> FEATURE:
<223> OTHER INFORMATION: MCa6-17

<400> SEQUENCE: 109

His Leu Lys Leu Cys Lys Glu Asn Lys Asp Cys Cys
1               5                   10

<210> SEQ ID NO 110
<211> LENGTH: 8
<212> TYPE: PRT
<213> ORGANISM: artificial sequence
<220> FEATURE:
<223> OTHER INFORMATION: MCa26-33

<400> SEQUENCE: 110

Thr Asn Ile Glu Lys Arg Cys Arg
1               5

<210> SEQ ID NO 111
<211> LENGTH: 7
<212> TYPE: PRT
<213> ORGANISM: artificial sequence
<220> FEATURE:
<223> OTHER INFORMATION: IpTxa18-25

<400> SEQUENCE: 111

Gly Lys Lys Cys Lys Arg Arg
1               5

<210> SEQ ID NO 112
<211> LENGTH: 12
<212> TYPE: PRT
<213> ORGANISM: artificial sequence
<220> FEATURE:
<223> OTHER INFORMATION: IpTxa6-17

<400> SEQUENCE: 112

His Leu Lys Arg Cys Lys Ala Asp Asn Asp Cys Cys
1               5                   10

<210> SEQ ID NO 113
<211> LENGTH: 12
<212> TYPE: PRT
<213> ORGANISM: artificial sequence
<220> FEATURE:
<223> OTHER INFORMATION: Opi6-17

<400> SEQUENCE: 113

His Leu Lys Arg Cys Lys Glu Asn Asn Asp Cys Cys
1               5                   10

<210> SEQ ID NO 114
<211> LENGTH: 12
<212> TYPE: PRT
<213> ORGANISM: artificial sequence
<220> FEATURE:
<223> OTHER INFORMATION: Hemi6-17

<400> SEQUENCE: 114

His Leu Lys Leu Cys Lys Ala Asp Lys Asp Cys Cys
1               5                   10
```

<210> SEQ ID NO 115
<211> LENGTH: 12
<212> TYPE: PRT
<213> ORGANISM: artificial sequence
<220> FEATURE:
<223> OTHER INFORMATION: Hadru8-19

<400> SEQUENCE: 115

His Leu Gln Arg Cys Arg Glu Asn Lys Asp Cys Cys
1               5                   10

<210> SEQ ID NO 116
<211> LENGTH: 8
<212> TYPE: PRT
<213> ORGANISM: artificial sequence
<220> FEATURE:
<223> OTHER INFORMATION: IpTxa26-33

<400> SEQUENCE: 116

Thr Asn Ala Glu Lys Arg Cys Arg
1               5

<210> SEQ ID NO 117
<211> LENGTH: 8
<212> TYPE: PRT
<213> ORGANISM: artificial sequence
<220> FEATURE:
<223> OTHER INFORMATION: Opi1-Hemi-Hadru26-33

<400> SEQUENCE: 117

Thr Asn Pro Glu Lys Arg Cys Arg
1               5

<210> SEQ ID NO 118
<211> LENGTH: 8
<212> TYPE: PRT
<213> ORGANISM: artificial sequence
<220> FEATURE:
<223> OTHER INFORMATION: Opi2 26-33

<400> SEQUENCE: 118

Ala Asn Pro Glu Lys Arg Cys Arg
1               5

<210> SEQ ID NO 119
<211> LENGTH: 12
<212> TYPE: PRT
<213> ORGANISM: artificial sequence
<220> FEATURE:
<223> OTHER INFORMATION: MCa14-25

<400> SEQUENCE: 119

Lys Asp Cys Cys Ser Lys Lys Cys Lys Arg Arg Gly
1               5                   10

<210> SEQ ID NO 120
<211> LENGTH: 16
<212> TYPE: PRT
<213> ORGANISM: artificial sequence
<220> FEATURE:
<223> OTHER INFORMATION: MCa18-33 C21,32Abu variant
<220> FEATURE:
<221> NAME/KEY: VARIANT
<222> LOCATION: (4)..(4)
<223> OTHER INFORMATION: 2-amino butyric acid
<220> FEATURE:
<221> NAME/KEY: VARIANT

```
<222> LOCATION: (15)..(15)
<223> OTHER INFORMATION: 2-amino butyric acid

<400> SEQUENCE: 120

Ser Lys Lys Xaa Lys Arg Arg Gly Thr Asn Ile Glu Lys Arg Xaa Arg
1               5                   10                  15

<210> SEQ ID NO 121
<211> LENGTH: 12
<212> TYPE: PRT
<213> ORGANISM: artificial sequence
<220> FEATURE:
<223> OTHER INFORMATION: MCa18-33delta26-29 C21,32Abu variant
<220> FEATURE:
<221> NAME/KEY: VARIANT
<222> LOCATION: (4)..(4)
<223> OTHER INFORMATION: 2-amino butyric acid
<220> FEATURE:
<221> NAME/KEY: VARIANT
<222> LOCATION: (11)..(11)
<223> OTHER INFORMATION: 2-amino butyric acid

<400> SEQUENCE: 121

Ser Lys Lys Xaa Lys Arg Arg Gly Lys Arg Xaa Arg
1               5                   10

<210> SEQ ID NO 122
<211> LENGTH: 20
<212> TYPE: PRT
<213> ORGANISM: artificial sequence
<220> FEATURE:
<223> OTHER INFORMATION: MCa6-25 C10,16,17,21Abu variant
<220> FEATURE:
<221> NAME/KEY: VARIANT
<222> LOCATION: (5)..(5)
<223> OTHER INFORMATION: 2-amino butyric acid
<220> FEATURE:
<221> NAME/KEY: VARIANT
<222> LOCATION: (11)..(11)
<223> OTHER INFORMATION: 2-amino butyric acid
<220> FEATURE:
<221> NAME/KEY: VARIANT
<222> LOCATION: (12)..(12)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid

<400> SEQUENCE: 122

His Leu Lys Leu Xaa Lys Glu Asn Lys Asp Xaa Xaa Ser Lys Lys Xaa
1               5                   10                  15

Lys Arg Arg Gly
            20

<210> SEQ ID NO 123
<211> LENGTH: 20
<212> TYPE: PRT
<213> ORGANISM: artificial sequence
<220> FEATURE:
<223> OTHER INFORMATION: MCa6-25 H6A/C10,16,17,21Abu variant
<220> FEATURE:
<221> NAME/KEY: VARIANT
<222> LOCATION: (5)..(5)
<223> OTHER INFORMATION: 2-amino butyric acid
<220> FEATURE:
<221> NAME/KEY: VARIANT
<222> LOCATION: (11)..(11)
<223> OTHER INFORMATION: 2-amino butyric acid
<220> FEATURE:
<221> NAME/KEY: VARIANT
<222> LOCATION: (12)..(12)
```

<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid

<400> SEQUENCE: 123

Ala Leu Lys Leu Xaa Lys Glu Asn Lys Asp Xaa Xaa Ser Lys Lys Xaa
1               5                   10                  15

Lys Arg Arg Gly
            20

<210> SEQ ID NO 124
<211> LENGTH: 20
<212> TYPE: PRT
<213> ORGANISM: artificial sequence
<220> FEATURE:
<223> OTHER INFORMATION: MCa6-25 K8A/C10,16,17,21Abu variant
<220> FEATURE:
<221> NAME/KEY: VARIANT
<222> LOCATION: (5)..(5)
<223> OTHER INFORMATION: 2-amino butyric acid
<220> FEATURE:
<221> NAME/KEY: VARIANT
<222> LOCATION: (11)..(11)
<223> OTHER INFORMATION: 2-amino butyric acid
<220> FEATURE:
<221> NAME/KEY: VARIANT
<222> LOCATION: (12)..(12)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid

<400> SEQUENCE: 124

His Leu Ala Leu Xaa Lys Glu Asn Lys Asp Xaa Xaa Ser Lys Lys Xaa
1               5                   10                  15

Lys Arg Arg Gly
            20

<210> SEQ ID NO 125
<211> LENGTH: 20
<212> TYPE: PRT
<213> ORGANISM: artificial sequence
<220> FEATURE:
<223> OTHER INFORMATION: MCa6-25 E12A/C10,16,17,21Abu variant
<220> FEATURE:
<221> NAME/KEY: VARIANT
<222> LOCATION: (5)..(5)
<223> OTHER INFORMATION: 2-amino butyric acid
<220> FEATURE:
<221> NAME/KEY: VARIANT
<222> LOCATION: (11)..(11)
<223> OTHER INFORMATION: 2-amino butyric acid
<220> FEATURE:
<221> NAME/KEY: VARIANT
<222> LOCATION: (12)..(12)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid

<400> SEQUENCE: 125

His Leu Lys Leu Xaa Lys Ala Asn Lys Asp Xaa Xaa Ser Lys Lys Xaa
1               5                   10                  15

Lys Arg Arg Gly
            20

```
<210> SEQ ID NO 126
<211> LENGTH: 20
<212> TYPE: PRT
<213> ORGANISM: artificial sequence
<220> FEATURE:
<223> OTHER INFORMATION: MCa6-25 D15A C10,16,17,21Abu variant
<220> FEATURE:
<221> NAME/KEY: VARIANT
<222> LOCATION: (5)..(5)
<223> OTHER INFORMATION: 2-amino butyric acid
<220> FEATURE:
<221> NAME/KEY: VARIANT
<222> LOCATION: (11)..(11)
<223> OTHER INFORMATION: 2-amino butyric acid
<220> FEATURE:
<221> NAME/KEY: VARIANT
<222> LOCATION: (12)..(12)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid

<400> SEQUENCE: 126

His Leu Lys Leu Xaa Lys Glu Asn Lys Ala Xaa Xaa Ser Lys Lys Xaa
1               5                   10                  15

Lys Arg Arg Gly
            20

<210> SEQ ID NO 127
<211> LENGTH: 20
<212> TYPE: PRT
<213> ORGANISM: artificial sequence
<220> FEATURE:
<223> OTHER INFORMATION: MCa6-25F C16,17Abu variant
<220> FEATURE:
<221> NAME/KEY: VARIANT
<222> LOCATION: (11)..(11)
<223> OTHER INFORMATION: 2-amino butyric acid
<220> FEATURE:
<221> NAME/KEY: VARIANT
<222> LOCATION: (12)..(12)
<223> OTHER INFORMATION: 2-amino butyric acid

<400> SEQUENCE: 127

His Leu Lys Leu Cys Lys Glu Asn Lys Asp Xaa Xaa Ser Lys Lys Cys
1               5                   10                  15

Lys Arg Arg Gly
            20

<210> SEQ ID NO 128
<211> LENGTH: 20
<212> TYPE: PRT
<213> ORGANISM: artificial sequence
<220> FEATURE:
<223> OTHER INFORMATION: MCa6-25F H6A/C16,17Abu variant
<220> FEATURE:
<221> NAME/KEY: VARIANT
<222> LOCATION: (11)..(11)
<223> OTHER INFORMATION: 2-amino butyric acid
<220> FEATURE:
<221> NAME/KEY: VARIANT
<222> LOCATION: (12)..(12)
<223> OTHER INFORMATION: 2-amino butyric acid

<400> SEQUENCE: 128

Ala Leu Lys Leu Cys Lys Glu Asn Lys Asp Xaa Xaa Ser Lys Lys Cys
1               5                   10                  15

Lys Arg Arg Gly
            20
```

<210> SEQ ID NO 129
<211> LENGTH: 20
<212> TYPE: PRT
<213> ORGANISM: artificial sequence
<220> FEATURE:
<223> OTHER INFORMATION: MCa6-25F K8A/C16,17Abu variant
<220> FEATURE:
<221> NAME/KEY: VARIANT
<222> LOCATION: (11)..(11)
<223> OTHER INFORMATION: 2-amino butyric acid
<220> FEATURE:
<221> NAME/KEY: VARIANT
<222> LOCATION: (12)..(12)
<223> OTHER INFORMATION: 2-amino butyric acid

<400> SEQUENCE: 129

His Leu Ala Leu Cys Lys Glu Asn Lys Asp Xaa Xaa Ser Lys Lys Cys
1               5                   10                  15

Lys Arg Arg Gly
            20

<210> SEQ ID NO 130
<211> LENGTH: 20
<212> TYPE: PRT
<213> ORGANISM: artificial sequence
<220> FEATURE:
<223> OTHER INFORMATION: MCa6-25F E12A/C16,17Abu variant
<220> FEATURE:
<221> NAME/KEY: VARIANT
<222> LOCATION: (11)..(11)
<223> OTHER INFORMATION: 2-amino butyric acid
<220> FEATURE:
<221> NAME/KEY: VARIANT
<222> LOCATION: (12)..(12)
<223> OTHER INFORMATION: 2-amino butyric acid

<400> SEQUENCE: 130

His Leu Lys Leu Cys Lys Ala Asn Lys Asp Xaa Xaa Ser Lys Lys Cys
1               5                   10                  15

Lys Arg Arg Gly
            20

<210> SEQ ID NO 131
<211> LENGTH: 20
<212> TYPE: PRT
<213> ORGANISM: artificial sequence
<220> FEATURE:
<223> OTHER INFORMATION: MCa6-25F D15A/C16,17Abu variant
<220> FEATURE:
<221> NAME/KEY: VARIANT
<222> LOCATION: (11)..(11)
<223> OTHER INFORMATION: 2-amino butyric acid
<220> FEATURE:
<221> NAME/KEY: VARIANT
<222> LOCATION: (12)..(12)
<223> OTHER INFORMATION: 2-amino butyric acid

<400> SEQUENCE: 131

His Leu Lys Leu Cys Lys Glu Asn Lys Ala Xaa Xaa Ser Lys Lys Cys
1               5                   10                  15

Lys Arg Arg Gly
            20

<210> SEQ ID NO 132
<211> LENGTH: 12
<212> TYPE: PRT
<213> ORGANISM: artificial sequence
<220> FEATURE:
<223> OTHER INFORMATION: MCa14-25 C16,17,21Abu

```
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (4)..(4)
<223> OTHER INFORMATION: 2-amino butyric acid
<220> FEATURE:
<221> NAME/KEY: VARIANT
<222> LOCATION: (8)..(8)
<223> OTHER INFORMATION: 2-amino butyric acid

<400> SEQUENCE: 132

Lys Asp Xaa Xaa Ser Lys Lys Xaa Lys Arg Arg Gly
1               5                   10

<210> SEQ ID NO 133
<211> LENGTH: 12
<212> TYPE: PRT
<213> ORGANISM: artificial sequence
<220> FEATURE:
<223> OTHER INFORMATION: MCa14-25 D15A/C16,17,21Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (4)..(4)
<223> OTHER INFORMATION: 2-amino butyric acid
<220> FEATURE:
<221> NAME/KEY: VARIANT
<222> LOCATION: (8)..(8)
<223> OTHER INFORMATION: 2-amino butyric acid

<400> SEQUENCE: 133

Lys Ala Xaa Xaa Ser Lys Lys Xaa Lys Arg Arg Gly
1               5                   10

<210> SEQ ID NO 134
<211> LENGTH: 21
<212> TYPE: PRT
<213> ORGANISM: artificial sequence
<220> FEATURE:
<223> OTHER INFORMATION: MCa1-20-C,C3,10,16,17Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid
<220> FEATURE:
<221> NAME/KEY: VARIANT
<222> LOCATION: (17)..(17)
<223> OTHER INFORMATION: 2-amino butyric acid

<400> SEQUENCE: 134

Gly Asp Xaa Leu Pro His Leu Lys Leu Xaa Lys Glu Asn Lys Asp Xaa
1               5                   10                  15

Xaa Ser Lys Lys Cys
            20

<210> SEQ ID NO 135
<211> LENGTH: 16
<212> TYPE: PRT
```

```
<213> ORGANISM: artificial sequence
<220> FEATURE:
<223> OTHER INFORMATION: MCa1-15-C,C3,10Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid

<400> SEQUENCE: 135

Gly Asp Xaa Leu Pro His Leu Lys Leu Xaa Lys Glu Asn Lys Asp Cys
1               5                   10                  15

<210> SEQ ID NO 136
<211> LENGTH: 10
<212> TYPE: PRT
<213> ORGANISM: artificial sequence
<220> FEATURE:
<223> OTHER INFORMATION: MCa1-9-C, C3Abu variant
<220> FEATURE:
<221> NAME/KEY: VARIANT
<222> LOCATION: (3)..(3)
<223> OTHER INFORMATION: 2-amino butyric acid

<400> SEQUENCE: 136

Gly Asp Xaa Leu Pro His Leu Lys Leu Cys
1               5                   10

<210> SEQ ID NO 137
<211> LENGTH: 17
<212> TYPE: PRT
<213> ORGANISM: artificial sequence
<220> FEATURE:
<223> OTHER INFORMATION: MCa18-33-C,C21,32Abu variant
<220> FEATURE:
<221> NAME/KEY: VARIANT
<222> LOCATION: (4)..(4)
<223> OTHER INFORMATION: 2-amino butyric acid
<220> FEATURE:
<221> NAME/KEY: VARIANT
<222> LOCATION: (15)..(15)
<223> OTHER INFORMATION: 2-amino butyric acid

<400> SEQUENCE: 137

Ser Lys Lys Xaa Lys Arg Arg Gly Thr Asn Ile Glu Lys Arg Xaa Arg
1               5                   10                  15

Cys

<210> SEQ ID NO 138
<211> LENGTH: 21
<212> TYPE: PRT
<213> ORGANISM: artificial sequence
<220> FEATURE:
<223> OTHER INFORMATION: MCa6-25-C,C10,16,17,21Abu variant
<220> FEATURE:
<221> NAME/KEY: VARIANT
<222> LOCATION: (5)..(5)
<223> OTHER INFORMATION: 2-amino butyric acid
<220> FEATURE:
<221> NAME/KEY: VARIANT
<222> LOCATION: (11)..(11)
<223> OTHER INFORMATION: 2-amino butyric acid
<220> FEATURE:
<221> NAME/KEY: VARIANT
<222> LOCATION: (12)..(12)
<223> OTHER INFORMATION: 2-amino butyric acid
<220> FEATURE:
<221> NAME/KEY: VARIANT
<222> LOCATION: (16)..(16)
```

<223> OTHER INFORMATION: 2-amino butyric acid

<400> SEQUENCE: 138

His Leu Lys Leu Xaa Lys Glu Asn Lys Asp Xaa Xaa Ser Lys Lys Xaa
1               5                   10                  15

Lys Arg Arg Gly Cys
            20

<210> SEQ ID NO 139
<211> LENGTH: 13
<212> TYPE: PRT
<213> ORGANISM: artificial sequence
<220> FEATURE:
<223> OTHER INFORMATION: MCa14-25-C,C16,17,21Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (4)..(4)
<223> OTHER INFORMATION: 2-amino butyric acid
<220> FEATURE:
<221> NAME/KEY: VARIANT
<222> LOCATION: (8)..(8)
<223> OTHER INFORMATION: 2-amino butyric acid

<400> SEQUENCE: 139

Lys Asp Xaa Xaa Ser Lys Lys Xaa Lys Arg Arg Gly Cys
1               5                   10

<210> SEQ ID NO 140
<211> LENGTH: 34
<212> TYPE: PRT
<213> ORGANISM: artificial sequence
<220> FEATURE:
<223> OTHER INFORMATION: MCa1-33-C,C3,10,16,17,21,32Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (16)..(16)
<223> OTHER INFORMATION: 2-amino butyric acid
<220> FEATURE:
<221> NAME/KEY: VARIANT
<222> LOCATION: (17)..(17)
<223> OTHER INFORMATION: 2-amino butyric acid
<220> FEATURE:
<221> NAME/KEY: VARIANT
<222> LOCATION: (21)..(21)
<223> OTHER INFORMATION: 2-amino butyric acid
<220> FEATURE:
<221> NAME/KEY: VARIANT
<222> LOCATION: (32)..(32)
<223> OTHER INFORMATION: 2-amino butyric acid

<400> SEQUENCE: 140

Gly Asp Xaa Leu Pro His Leu Lys Leu Xaa Lys Glu Asn Lys Asp Xaa
1               5                   10                  15

Xaa Ser Lys Lys Xaa Lys Arg Arg Gly Thr Asn Ile Glu Lys Arg Xaa
                20                  25                  30

Arg Cys

<210> SEQ ID NO 141

```
<211> LENGTH: 27
<212> TYPE: PRT
<213> ORGANISM: artificial sequence
<220> FEATURE:
<223> OTHER INFORMATION: MCa8-33-C,C10,16,17,21,32Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
<222> LOCATION: (9)..(9)
<223> OTHER INFORMATION: 2-amino butyric acid
<220> FEATURE:
<221> NAME/KEY: VARIANT
<222> LOCATION: (10)..(10)
<223> OTHER INFORMATION: 2-amino butyric acid
<220> FEATURE:
<221> NAME/KEY: VARIANT
<222> LOCATION: (14)..(14)
<223> OTHER INFORMATION: 2-amino butyric acid
<220> FEATURE:
<221> NAME/KEY: VARIANT
<222> LOCATION: (25)..(25)
<223> OTHER INFORMATION: 2-amino butyric acid

<400> SEQUENCE: 141

Lys Leu Xaa Lys Glu Asn Lys Asp Xaa Xaa Ser Lys Lys Xaa Lys Arg
1               5                   10                  15

Arg Gly Thr Asn Ile Glu Lys Arg Xaa Arg Cys
            20                  25

<210> SEQ ID NO 142
<211> LENGTH: 24
<212> TYPE: PRT
<213> ORGANISM: artificial sequence
<220> FEATURE:
<223> OTHER INFORMATION: MCa11-33-C,C16,17,21,32Abu variant
<220> FEATURE:
<221> NAME/KEY: VARIANT
<222> LOCATION: (6)..(6)
<223> OTHER INFORMATION: 2-amino butyric acid
<220> FEATURE:
<221> NAME/KEY: VARIANT
<222> LOCATION: (7)..(7)
<223> OTHER INFORMATION: 2-amino butyric acid
<220> FEATURE:
<221> NAME/KEY: VARIANT
<222> LOCATION: (11)..(11)
<223> OTHER INFORMATION: 2-amino butyric acid
<220> FEATURE:
<221> NAME/KEY: VARIANT
<222> LOCATION: (22)..(22)
<223> OTHER INFORMATION: 2-amino butyric acid

<400> SEQUENCE: 142

Lys Glu Asn Lys Asp Xaa Xaa Ser Lys Lys Xaa Lys Arg Arg Gly Thr
1               5                   10                  15

Asn Ile Glu Lys Arg Xaa Arg Cys
            20

<210> SEQ ID NO 143
<211> LENGTH: 21
<212> TYPE: PRT
<213> ORGANISM: artificial sequence
<220> FEATURE:
<223> OTHER INFORMATION: MCa14-33-C,C16,17,21,32Abu variant
<220> FEATURE:
<221> NAME/KEY: VARIANT
<222> LOCATION: (3)..(3)
<223> OTHER INFORMATION: 2-amino butyric acid
<220> FEATURE:
<221> NAME/KEY: VARIANT
```

-continued

```
<222> LOCATION: (4)..(4)
<223> OTHER INFORMATION: 2-amino butyric acid
<220> FEATURE:
<221> NAME/KEY: VARIANT
<222> LOCATION: (8)..(8)
<223> OTHER INFORMATION: 2-amino butyric acid
<220> FEATURE:
<221> NAME/KEY: misc_feature
<222> LOCATION: (19)..(19)
<223> OTHER INFORMATION: Xaa can be any naturally occurring amino acid

<400> SEQUENCE: 143

Lys Asp Xaa Xaa Ser Lys Lys Xaa Lys Arg Arg Gly Thr Asn Ile Glu
1               5                   10                  15

Lys Arg Xaa Arg Cys
            20

<210> SEQ ID NO 144
<211> LENGTH: 15
<212> TYPE: PRT
<213> ORGANISM: artificial sequence
<220> FEATURE:
<223> OTHER INFORMATION: MCa20-33-C,C21,32Abu variant
<220> FEATURE:
<221> NAME/KEY: VARIANT
<222> LOCATION: (2)..(2)
<223> OTHER INFORMATION: 2-amino butyric acid
<220> FEATURE:
<221> NAME/KEY: VARIANT
<222> LOCATION: (13)..(13)
<223> OTHER INFORMATION: 2-amino butyric acid

<400> SEQUENCE: 144

Lys Xaa Lys Arg Arg Gly Thr Asn Ile Glu Lys Arg Xaa Arg Cys
1               5                   10                  15

<210> SEQ ID NO 145
<211> LENGTH: 13
<212> TYPE: PRT
<213> ORGANISM: artificial sequence
<220> FEATURE:
<223> OTHER INFORMATION: MCa22-33-C,C32Abu variant
<220> FEATURE:
<221> NAME/KEY: VARIANT
<222> LOCATION: (11)..(11)
<223> OTHER INFORMATION: 2-amino butyric acid

<400> SEQUENCE: 145

Lys Arg Arg Gly Thr Asn Ile Glu Lys Arg Xaa Arg Cys
1               5                   10

<210> SEQ ID NO 146
<211> LENGTH: 10
<212> TYPE: PRT
<213> ORGANISM: artificial sequence
<220> FEATURE:
<223> OTHER INFORMATION: MCa25-33-C,C32Abu variant
<220> FEATURE:
<221> NAME/KEY: VARIANT
<222> LOCATION: (8)..(8)
<223> OTHER INFORMATION: 2-amino butyric acid

<400> SEQUENCE: 146

Gly Thr Asn Ile Glu Lys Arg Xaa Arg Cys
1               5                   10

<210> SEQ ID NO 147
<211> LENGTH: 10
<212> TYPE: PRT
<213> ORGANISM: artificial sequence
```

```
<220> FEATURE:
<223> OTHER INFORMATION: MCa1-9-C,C3A variant

<400> SEQUENCE: 147

Gly Asp Ala Leu Pro His Leu Lys Leu Cys
1               5                   10

<210> SEQ ID NO 148
<211> LENGTH: 9
<212> TYPE: PRT
<213> ORGANISM: artificial sequence
<220> FEATURE:
<223> OTHER INFORMATION: Imp1-9,C3Abu variant
<220> FEATURE:
<221> NAME/KEY: VARIANT
<222> LOCATION: (3)..(3)
<223> OTHER INFORMATION: 2-amino butyric acid

<400> SEQUENCE: 148

Gly Asp Xaa Leu Pro His Leu Lys Arg
1               5

<210> SEQ ID NO 149
<211> LENGTH: 10
<212> TYPE: PRT
<213> ORGANISM: artificial sequence
<220> FEATURE:
<223> OTHER INFORMATION: Imp1-9-C,C3Abu variant
<220> FEATURE:
<221> NAME/KEY: VARIANT
<222> LOCATION: (3)..(3)
<223> OTHER INFORMATION: 2-amino butyric acid

<400> SEQUENCE: 149

Gly Asp Xaa Leu Pro His Leu Lys Arg Cys
1               5                   10

<210> SEQ ID NO 150
<211> LENGTH: 11
<212> TYPE: PRT
<213> ORGANISM: artificial sequence
<220> FEATURE:
<223> OTHER INFORMATION: Had1-11,C5Abu variant
<220> FEATURE:
<221> NAME/KEY: VARIANT
<222> LOCATION: (5)..(5)
<223> OTHER INFORMATION: 2-amino butyric acid

<400> SEQUENCE: 150

Ser Glu Lys Asp Xaa Ile Lys His Leu Gln Arg
1               5                   10

<210> SEQ ID NO 151
<211> LENGTH: 12
<212> TYPE: PRT
<213> ORGANISM: artificial sequence
<220> FEATURE:
<223> OTHER INFORMATION: Had1-11-C,C5Abu variant
<220> FEATURE:
<221> NAME/KEY: VARIANT
<222> LOCATION: (5)..(5)
<223> OTHER INFORMATION: 2-amino butyric acid

<400> SEQUENCE: 151

Ser Glu Lys Asp Xaa Ile Lys His Leu Gln Arg Cys
1               5                   10

<210> SEQ ID NO 152
<211> LENGTH: 9
```

```
<212> TYPE: PRT
<213> ORGANISM: artificial sequence
<220> FEATURE:
<223> OTHER INFORMATION: Had3-11,C5Abu variant
<220> FEATURE:
<221> NAME/KEY: VARIANT
<222> LOCATION: (3)..(3)
<223> OTHER INFORMATION: 2-amino butyric acid

<400> SEQUENCE: 152

Lys Asp Xaa Ile Lys His Leu Gln Arg
1               5

<210> SEQ ID NO 153
<211> LENGTH: 10
<212> TYPE: PRT
<213> ORGANISM: artificial sequence
<220> FEATURE:
<223> OTHER INFORMATION: Had3-11-C,C5Abu variant
<220> FEATURE:
<221> NAME/KEY: VARIANT
<222> LOCATION: (3)..(3)
<223> OTHER INFORMATION: 2-amino butyric acid

<400> SEQUENCE: 153

Lys Asp Xaa Ile Lys His Leu Gln Arg Cys
1               5                   10

<210> SEQ ID NO 154
<211> LENGTH: 9
<212> TYPE: PRT
<213> ORGANISM: artificial sequence
<220> FEATURE:
<223> OTHER INFORMATION: MCa1-9, C3W variant

<400> SEQUENCE: 154

Gly Asp Trp Leu Pro His Leu Lys Leu
1               5

<210> SEQ ID NO 155
<211> LENGTH: 10
<212> TYPE: PRT
<213> ORGANISM: artificial sequence
<220> FEATURE:
<223> OTHER INFORMATION: MCa1-9-C,C3W variant

<400> SEQUENCE: 155

Gly Asp Trp Leu Pro His Leu Lys Leu Cys
1               5                   10

<210> SEQ ID NO 156
<211> LENGTH: 10
<212> TYPE: PRT
<213> ORGANISM: artificial sequence
<220> FEATURE:
<223> OTHER INFORMATION: MCa1-9-C,D2A,C3Abu variant
<220> FEATURE:
<221> NAME/KEY: VARIANT
<222> LOCATION: (3)..(3)
<223> OTHER INFORMATION: 2-amino butyric acid

<400> SEQUENCE: 156

Gly Ala Xaa Leu Pro His Leu Lys Leu Cys
1               5                   10

<210> SEQ ID NO 157
<211> LENGTH: 8
<212> TYPE: PRT
<213> ORGANISM: artificial sequence
```

```
<220> FEATURE:
<223> OTHER INFORMATION: MCa3-9-C,C3Abu variant
<220> FEATURE:
<221> NAME/KEY: VARIANT
<222> LOCATION: (1)..(1)
<223> OTHER INFORMATION: 2-amino butyric acid

<400> SEQUENCE: 157

Xaa Leu Pro His Leu Lys Leu Cys
1               5

<210> SEQ ID NO 158
<211> LENGTH: 9
<212> TYPE: PRT
<213> ORGANISM: artificial sequence
<220> FEATURE:
<223> OTHER INFORMATION: MCa1-9,C3Abu,H6W variant
<220> FEATURE:
<221> NAME/KEY: VARIANT
<222> LOCATION: (3)..(3)
<223> OTHER INFORMATION: 2-amino butyric acid

<400> SEQUENCE: 158

Gly Asp Xaa Leu Pro Trp Leu Lys Leu
1               5

<210> SEQ ID NO 159
<211> LENGTH: 10
<212> TYPE: PRT
<213> ORGANISM: artificial sequence
<220> FEATURE:
<223> OTHER INFORMATION: MCa1-9-C,C3Abu,H6W variant
<220> FEATURE:
<221> NAME/KEY: VARIANT
<222> LOCATION: (3)..(3)
<223> OTHER INFORMATION: 2-amino butyric acid

<400> SEQUENCE: 159

Gly Asp Xaa Leu Pro Trp Leu Lys Leu Cys
1               5                   10

<210> SEQ ID NO 160
<211> LENGTH: 9
<212> TYPE: PRT
<213> ORGANISM: artificial sequence
<220> FEATURE:
<223> OTHER INFORMATION: MCa1-9,C3Abu,L4W variant
<220> FEATURE:
<221> NAME/KEY: VARIANT
<222> LOCATION: (3)..(3)
<223> OTHER INFORMATION: 2-amino butyric acid

<400> SEQUENCE: 160

Gly Asp Xaa Trp Pro His Leu Lys Leu
1               5

<210> SEQ ID NO 161
<211> LENGTH: 10
<212> TYPE: PRT
<213> ORGANISM: artificial sequence
<220> FEATURE:
<223> OTHER INFORMATION: MCa1-9-C,C3Abu,L4W variant
<220> FEATURE:
<221> NAME/KEY: VARIANT
<222> LOCATION: (3)..(3)
<223> OTHER INFORMATION: 2-amino butyric acid

<400> SEQUENCE: 161

Gly Asp Xaa Trp Pro His Leu Lys Leu Cys
1               5                   10
```

<210> SEQ ID NO 162
<211> LENGTH: 9
<212> TYPE: PRT
<213> ORGANISM: artificial sequence
<220> FEATURE:
<223> OTHER INFORMATION: MCa1-9,C3Abu,L7F variant
<220> FEATURE:
<221> NAME/KEY: VARIANT
<222> LOCATION: (3)..(3)
<223> OTHER INFORMATION: 2-amino butyric acid

<400> SEQUENCE: 162

Gly Asp Xaa Leu Pro His Phe Lys Leu
1               5

<210> SEQ ID NO 163
<211> LENGTH: 10
<212> TYPE: PRT
<213> ORGANISM: artificial sequence
<220> FEATURE:
<223> OTHER INFORMATION: MCa1-9-C,C3Abu,L7F variant
<220> FEATURE:
<221> NAME/KEY: VARIANT
<222> LOCATION: (3)..(3)
<223> OTHER INFORMATION: 2-amino butyric acid

<400> SEQUENCE: 163

Gly Asp Xaa Leu Pro His Phe Lys Leu Cys
1               5                   10

<210> SEQ ID NO 164
<211> LENGTH: 9
<212> TYPE: PRT
<213> ORGANISM: artificial sequence
<220> FEATURE:
<223> OTHER INFORMATION: MCa1-9,C3Abu,L9M variant
<220> FEATURE:
<221> NAME/KEY: VARIANT
<222> LOCATION: (3)..(3)
<223> OTHER INFORMATION: 2-amino butyric acid

<400> SEQUENCE: 164

Gly Asp Xaa Leu Pro His Leu Lys Met
1               5

<210> SEQ ID NO 165
<211> LENGTH: 10
<212> TYPE: PRT
<213> ORGANISM: artificial sequence
<220> FEATURE:
<223> OTHER INFORMATION: MCa1-9-C,C3Abu,L9M variant
<220> FEATURE:
<221> NAME/KEY: VARIANT
<222> LOCATION: (3)..(3)
<223> OTHER INFORMATION: 2-amino butyric acid

<400> SEQUENCE: 165

Gly Asp Xaa Leu Pro His Leu Lys Met Cys
1               5                   10

<210> SEQ ID NO 166
<211> LENGTH: 9
<212> TYPE: PRT
<213> ORGANISM: artificial sequence
<220> FEATURE:
<223> OTHER INFORMATION: MCa1-9,C3Q variant

<400> SEQUENCE: 166

```
Gly Asp Gln Leu Pro His Leu Lys Leu
1               5

<210> SEQ ID NO 167
<211> LENGTH: 10
<212> TYPE: PRT
<213> ORGANISM: artificial sequence
<220> FEATURE:
<223> OTHER INFORMATION: MCa1-9-C,C3Q variant

<400> SEQUENCE: 167

Gly Asp Gln Leu Pro His Leu Lys Leu Cys
1               5                   10

<210> SEQ ID NO 168
<211> LENGTH: 9
<212> TYPE: PRT
<213> ORGANISM: artificial sequence
<220> FEATURE:
<223> OTHER INFORMATION: MCa1-9,C3Abu,L9N variant
<220> FEATURE:
<221> NAME/KEY: VARIANT
<222> LOCATION: (3)..(3)
<223> OTHER INFORMATION: 2-amino butyric acid

<400> SEQUENCE: 168

Gly Asp Xaa Leu Pro His Leu Lys Asn
1               5

<210> SEQ ID NO 169
<211> LENGTH: 10
<212> TYPE: PRT
<213> ORGANISM: artificial sequence
<220> FEATURE:
<223> OTHER INFORMATION: MCa1-9-C,C3Abu,L9N variant
<220> FEATURE:
<221> NAME/KEY: VARIANT
<222> LOCATION: (3)..(3)
<223> OTHER INFORMATION: 2-amino butyric acid

<400> SEQUENCE: 169

Gly Asp Xaa Leu Pro His Leu Lys Asn Cys
1               5                   10

<210> SEQ ID NO 170
<211> LENGTH: 9
<212> TYPE: PRT
<213> ORGANISM: artificial sequence
<220> FEATURE:
<223> OTHER INFORMATION: MCa1-9,C3Abu,P5R,K8I variant
<220> FEATURE:
<221> NAME/KEY: VARIANT
<222> LOCATION: (3)..(3)
<223> OTHER INFORMATION: 2-amino butyric acid

<400> SEQUENCE: 170

Gly Asp Xaa Leu Arg His Leu Ile Leu
1               5

<210> SEQ ID NO 171
<211> LENGTH: 10
<212> TYPE: PRT
<213> ORGANISM: artificial sequence
<220> FEATURE:
<223> OTHER INFORMATION: MCa1-9-C,C3Abu,P5R,K8I variant
<220> FEATURE:
<221> NAME/KEY: VARIANT
<222> LOCATION: (3)..(3)
<223> OTHER INFORMATION: 2-amino butyric acid
```

```
<400> SEQUENCE: 171

Gly Asp Xaa Leu Arg His Leu Ile Leu Cys
1               5                   10

<210> SEQ ID NO 172
<211> LENGTH: 11
<212> TYPE: PRT
<213> ORGANISM: artificial sequence
<220> FEATURE:
<223> OTHER INFORMATION: Tat-C

<400> SEQUENCE: 172

Gly Arg Lys Lys Arg Arg Gln Arg Arg Cys
1               5                   10

<210> SEQ ID NO 173
<211> LENGTH: 4
<212> TYPE: PRT
<213> ORGANISM: artificial sequence
<220> FEATURE:
<223> OTHER INFORMATION: synthetic peptide

<400> SEQUENCE: 173

Ser Glu Lys Asp
1
```